US008226965B2

(12) United States Patent
Baker, Jr. et al.

(10) Patent No.: US 8,226,965 B2
(45) Date of Patent: Jul. 24, 2012

(54) METHODS OF TREATING FUNGAL, YEAST AND MOLD INFECTIONS

(75) Inventors: James R. Baker, Jr., Ann Arbor, MI (US); Mary R. Flack, Ann Arbor, MI (US); Susan Marie Ciotti, Ann Arbor, MI (US); Joyce A. Sutcliffe, West Newton, MA (US)

(73) Assignee: NanoBio Corporation, Ann Arbor, MI (US)

( * ) Notice: Subject to any disclaimer, the term of this patent is extended or adjusted under 35 U.S.C. 154(b) by 347 days.

(21) Appl. No.: 12/430,700

(22) Filed: Apr. 27, 2009

(65) Prior Publication Data

US 2009/0269380 A1     Oct. 29, 2009

Related U.S. Application Data

(60) Provisional application No. 61/048,075, filed on Apr. 25, 2008, provisional application No. 61/129,962, filed on Aug. 1, 2008, provisional application No. 61/115,879, filed on Nov. 18, 2008.

(51) Int. Cl.
*A01N 25/00* (2006.01)
*A61L 15/16* (2006.01)
*A61K 9/00* (2006.01)
*A61K 36/48* (2006.01)

(52) U.S. Cl. ........ 424/405; 424/447; 424/400; 424/757; 977/906

(58) Field of Classification Search .................. None
See application file for complete search history.

(56) References Cited

U.S. PATENT DOCUMENTS

| | | | |
|---|---|---|---|
| 4,895,452 | A | 1/1990 | Yiornas et al. |
| 5,103,497 | A | 4/1992 | Hicks |
| 6,015,832 | A | 1/2000 | Baker, Jr. et al. |
| 6,506,803 | B1 | 1/2003 | Baker, Jr. et al. |
| 6,559,189 | B2 | 5/2003 | Baker, Jr. et al. |
| 6,635,676 | B2 | 10/2003 | Baker, Jr. et al. |
| 7,314,624 | B2 | 1/2008 | Baker et al. |
| 2003/0022941 | A1 * | 1/2003 | Taylor et al. .................. 514/642 |
| 2004/0043041 | A1 | 3/2004 | Baker, Jr. et al. |
| 2005/0208083 | A1 | 9/2005 | Annis |
| 2006/0251684 | A1 * | 11/2006 | Annis et al. .................. 424/400 |
| 2007/0036831 | A1 * | 2/2007 | Baker .......................... 424/400 |
| 2007/0054834 | A1 | 3/2007 | Baker |
| 2007/0116709 | A1 | 5/2007 | O'Hagan et al. |

FOREIGN PATENT DOCUMENTS

| | | |
|---|---|---|
| EP | 1 156 781 B1 | 11/2001 |
| WO | WO 00/50006 | 8/2000 |
| WO | WO 03/000243 A1 | 1/2003 |
| WO | WO 2005/027872 A2 | 3/2005 |
| WO | WO 2005/030172 A1 | 4/2005 |

OTHER PUBLICATIONS

Abi-Said et al., "The epidemiology of hematogenous candidiasis caused by different *Candida* species," *Clin. Infect. Dis.*, 24:1122-1128 (1997).

Aisner et al, "*Torulopsis glabrata* infections in patients with cancer: Increasing incidence and relationship to colonization," *Am. J. Med.*, 61:23-28 (1976).

Arikan et al., "Primary cutaneous aspergillosis in human immunodeficiency virus-infected patients: Two cases and review," *Clin. Infect. Dis.*, 27:641-643 (1998).

Barchiesi et al., "Emergence of oropharyngeal candidiasis caused by non-albicans species of *Candida* in HIV-infected patients (letter)," *Eur. J. Epidemiol.*, 9:455-456 (1993).

Byrd et al., "*Paecilomyces variotii* penumonia in a patient with diabetes mellitus," *J. Diabetes Complic.*, 6:150-153 (1992).

Cohen-Abbo et al., "Multifocal osteomyelitis caused by *Paecilomyces varioti* in a patient with chronic granulomatous disease," *Infection*, 23:55-7 (1995).

Denning, D. W., "Invasive aspergillosis," *Clin. Infect. Dis.*, 26:781-803 (1998).

Dhindsa et al., "Chronic supparative otitis media caused by *Paecilomyces variotii*," *J. Med. Vet. Mycol.*, 33:59-61 (1995).

Fletcher et al., "Onychomycosis caused by infection with *Paecilomyces lilanicus*," *Br. J. Dermatol.*, 139:1133-1135 (1998).

Franz TJ, "The finite dose technique as a valid in vitro model for the study of percutaneous absorption in man," *Skin: Drug Application and Evaluation of Environmental Hazards, Current Problems in Dermatology*, vol. 7, pp. 58-68, Simon et al. (Eds) (Basel, Switzerland, S. Karger, 1978).

Franz, TJ, "Percutaneous absorption: on the relevance of in vitro data," *J. Invest. Dermatol.*, 64:190-195 (1975).

Gefter, W. B., "The spectrum of pulmonary aspergillosis," *Journal of Thoracic Imaging*, 7:56-74 (1992).

Groll et al., "Uncommon opportunistic fungi: new nosocomial threats," *Clin. Microbiol. Infect.*, 7 Suppl. 2:8-24 (2001).

Gucalp et al., "*Paecilomyces sinusitis* in an immunocompromised adult patient: Case report and review," *Clin. Infect. Dis.*, 23:391-393 (1996).

Gumbo et al., "Aspergillus valve endocarditis in patients without prior cardiac surgery," *Medicine* (Baltimore), 79:261-268 (2000).

Gupta et al., "Combined distal and lateral subungual and white superficial onychomycosis in the toenails," *J. Am. Acad. Dermatol.*, 41:938-44 (1999).

Jade et al., "*Paecilomyces lilacinus* cellulitis in an immunocompromised patient," *Arch. Dermatol.*, 122:1169-70 (1986).

Katz et al., "Ocular aspergillosis isolated in the anterior chamber," *Ophthalmology*, 100:1815-1818 (1993).

Leem et al., "The Possible Mechanism of Action of Ciclopirox Olamine in the Yeast *Saccharomyces cerevisiae*," *Mol. Cells.*, 15(1):55-61 (2003).

Louie et al., "Endogenous endophthalmitis due to Fusarium: case report and review," *Clin. Infect. Dis.*, 18:585-8 (1994).

Malani et al., "Changing epidemiology of rare mould infections: implications for therapy," *Drugs*, 67:1803-1812 (2007).

(Continued)

*Primary Examiner* — Chris R Tate
*Assistant Examiner* — Russell Fiebig
(74) *Attorney, Agent, or Firm* — Foley & Lardner LLP

(57) ABSTRACT

The present invention relates to methods for treating and completely curing fungal, yeast, and/or mold infections in human subjects comprising topically administering to a human subject in need thereof an antifungal nanoemulsion composition.

31 Claims, 26 Drawing Sheets

OTHER PUBLICATIONS

Mayayo et al., "Experimental pathogenicity of four opportunist *Fusarium* species in a murine model," *J. Med. Microbiol.*, 48:363-366 (1999).

Meyers, (Meyers, Surfactant Science and Technology, VCH Publishers Inc., New York, pp. 231-245 (1992).

Orth et al., "Outbreak of invasive mycoses caused by *Paecilomyces lilacinus* from a contaminated skin lotion," *Ann. Intern. Med.*, 125:799-806 (1996).

Pettit et al., "Fungal endophthalmitis following intraocular lens implantation. A surgical epidemic," *Arch. Ophthalmol.*, 98:1025-1039 (1980).

Rinaldi et al., "*Paecilomyces variotii* peritonitis in an infant on automated peritoneal dialysis," *Pediat. Nephrol.*, 14:365-366 (2000).

Rolston, K. V., "The spectrum of pulmonary infections in cancer patients," *Curr. Opin. Oncol.*, 13:218-223 (2001).

Romano et al., "Skin and nail infections due to *Fusarium oxysporum* in Tuscany, Italy," *Mycoses*, 41:433-437 (1998).

Safdar, A., "Progressive cutaneous hyalohyphomycosis due to *Paecilomyces lilacinus*: Rapid response to treatment with caspofungin and Itraconazole," *Clin. Infect. Dis.*, 34:1415-1417 (2002).

Sampathkumar et al., "Fusarium infection after solid-organ transplantation," *Clin. Infect. Dis.*, 32:1237-1240 (2001).

Tanure et al., "Spectrum of fungal keratitis at Wills Eye Hospital, Philadelphia, Pennsylvania," *Cornea*, 19:307-12 (2000).

Tosti et al., "Onychomycosis caused by Nondermatophytic molds: Clinical features and response to treatment of 59 cases," *J. Am. Acad. Dermatol.*, 42:217-224 (2000).

Vartivarian et al., "Emerging fungal pathogens in immunocompromised patients: classification, diagnosis, and management," *Clin. Infect. Dis.* 17:S487-91 (1993).

Venditti et al., "Invasive *Fusarium solani* infections in patients with acute leukemia," *Rev. Infect. Dis.*, 10:653-660 (1988).

Wadhwani et al., "Fungi from otitis media of agricultural field workers," *Mycopathologia*, 88:155-9 (1984).

Williamson et al., "Successful treatment of *Paecilomyces varioti* infection in a patient with chronic granulomatous disease and a review of *Paecilomyces* species infections," *Clin. Infect. Dis.*, 14:1023-1026 (1992).

Yildiran et al., "*Fusarium fungaemia* in severely neutropenic patients," *Mycoses*, 41:467-469 (1998).

International Preliminary Report on Patentability cited in related International Patent Application No. PCT/US2009/041811, issued Oct. 26, 2010.

International Search Report for related International Patent Application No. PCT/US2009/041811 completed Sep. 9, 2009.

Written Opinion of the International Searching Authority for related International Patent Application No. PCT/US2009/041811 completed Sep. 9, 2009.

Fothergill, "Antifungal Activity of NB-002, A Topical Nanoemulsion, Against Rare Fungal Pathogens of Onychomycosis," *Journ. of the Amer. Acad. of Derm.*, vol. 60, No. 3, p. AB117 (2009).

Jones, "Safety, Tolerance, and Pharmacokinetics of Topical Nanoemulsion (NB-002) for the Treatment of Onychomycosis," *Journ. of the Amer. Acad. of Derm.*, vol. 58, No. 2, p. AB83 (2008).

Arif et al., "Techniques for investigation of an apparent outbreak of infections with *Candida glabrata*," *J. Clin. Microbiol.*, vol. 34, No. 9, pp. 2205-2209 (1996).

Nir-Paz et al., "Deep Infection by Trichophyton Rubrum in an Immunocompromised Patient," *J. Clin. Microbiol.*, vol. 41, No. 11, pp. 5298-5301 (2003).

Rockhill et al., "*Paecilomyces lilacinus* as the cause of chronic maxillary sinusitis," *J. Clin. Microbiol.*, vol. 11, No. 6, pp. 737-739 (1980).

Haldane et al., "Prosthetic valvular endocarditis due to the fungus *Paecilomyces*," *Can. Med. Assoc. J.*, vol. 111, pp. 963-968 (1974).

Tan et al., "*Paecilomyces lilacinus* catheter-related fungemia in an immunocompromised pediatric patient," *J. Clin. Microbiol.*, vol. 30, No. 9, pp. 2479-2483 (1992).

Ghannoum, et. al. "Interlaboratory Study of Quality Control Isolates for a Broth Microdilution Method (Modified CLSI M38-A) for Testing Susceptibilities of Dermatophytes to Antifungals," J. Clin. Microbiol., vol. 44, No. 12, pp. 4353-4356 (2006).

\* cited by examiner

Figure 1: Nanoemulsion Delivery into Skin

Skin cross section under fluorescence
With Nanoemulsion

Without Nanoemulsion

Skin Cross-section

Figure 2: Nanoemulsion Delivery into Skin

With Nanoemulsion

Skin cross section under fluorescence
Without Nanoemulsion

Skin Cross-section

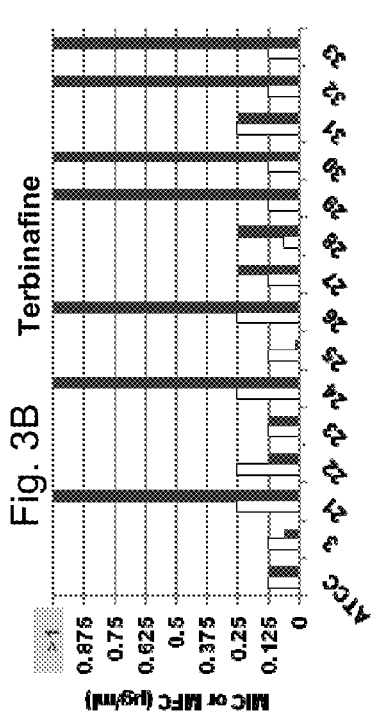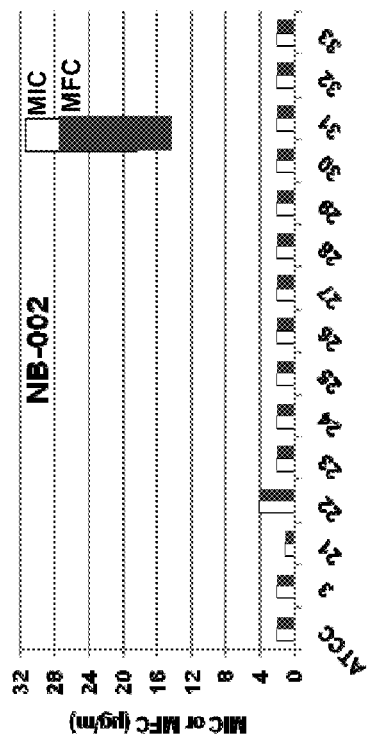
Figure 3. Nanoemulsions are Consistently Fungicidal to Isolates of *T. rubrum*
Note: Y axis represents highest concentration tested

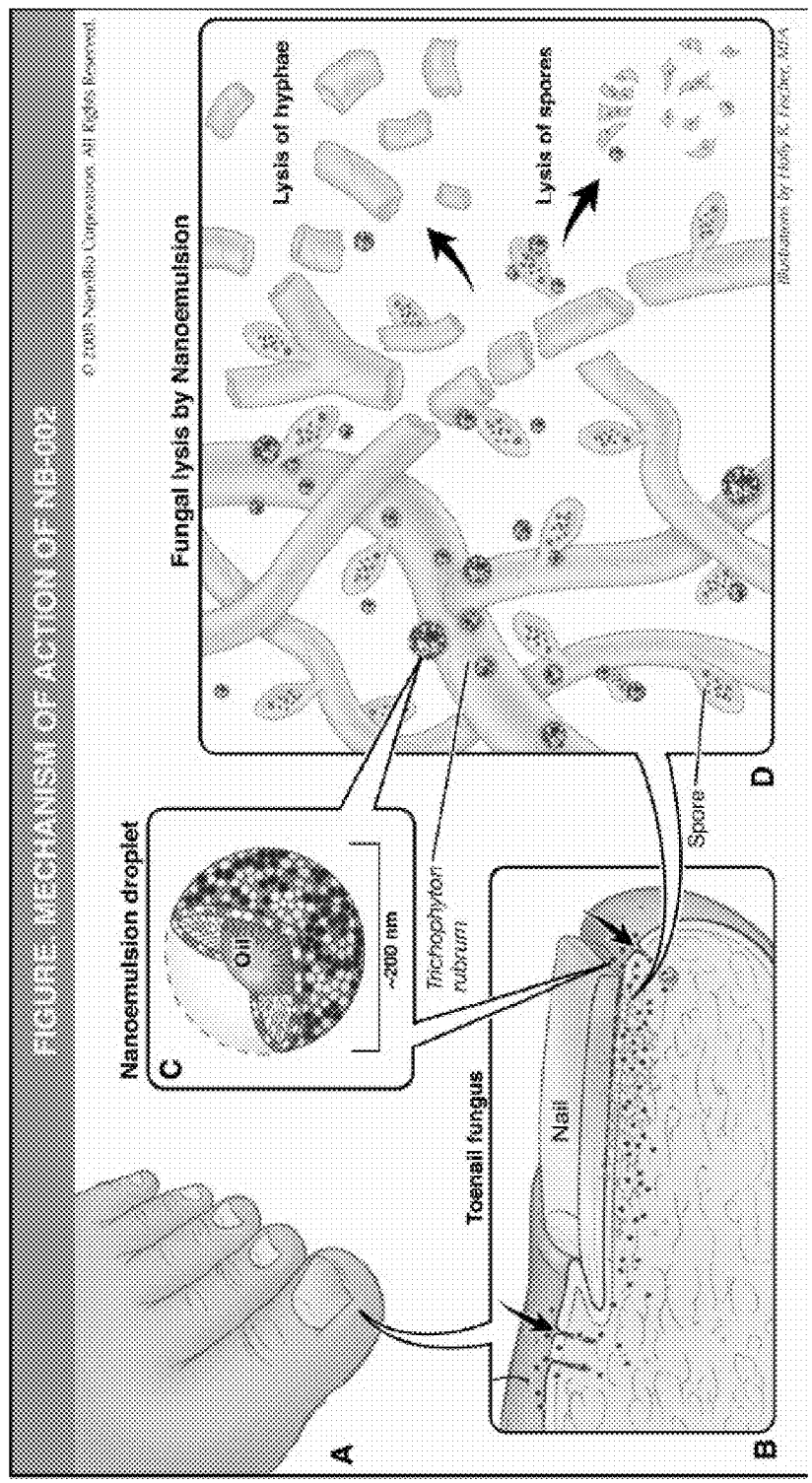
Figure 4: Mechanism of Action

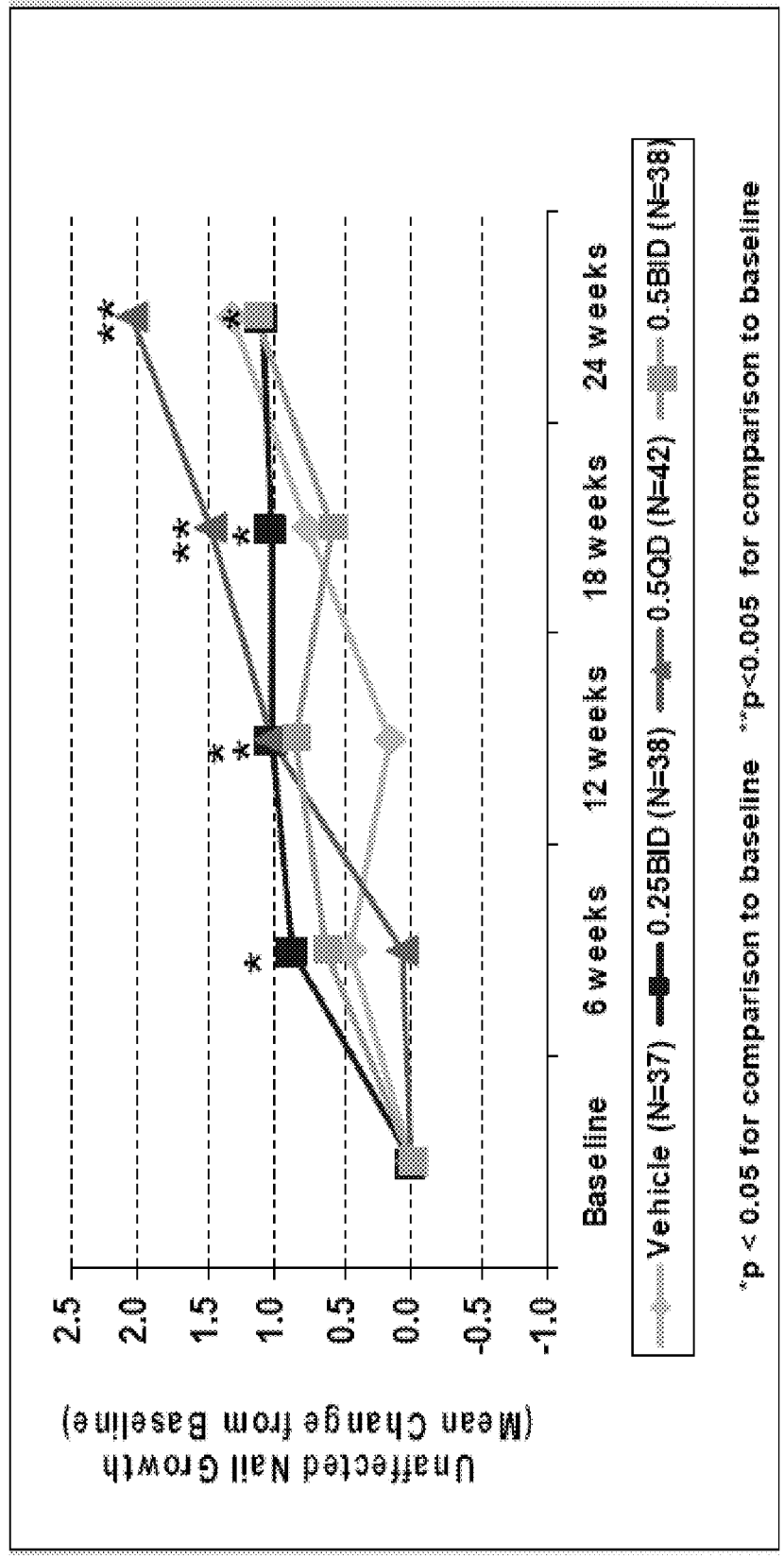
Figure 5: Change from Baseline in Unaffected Linear Nail Growth (Investigator Assessment)

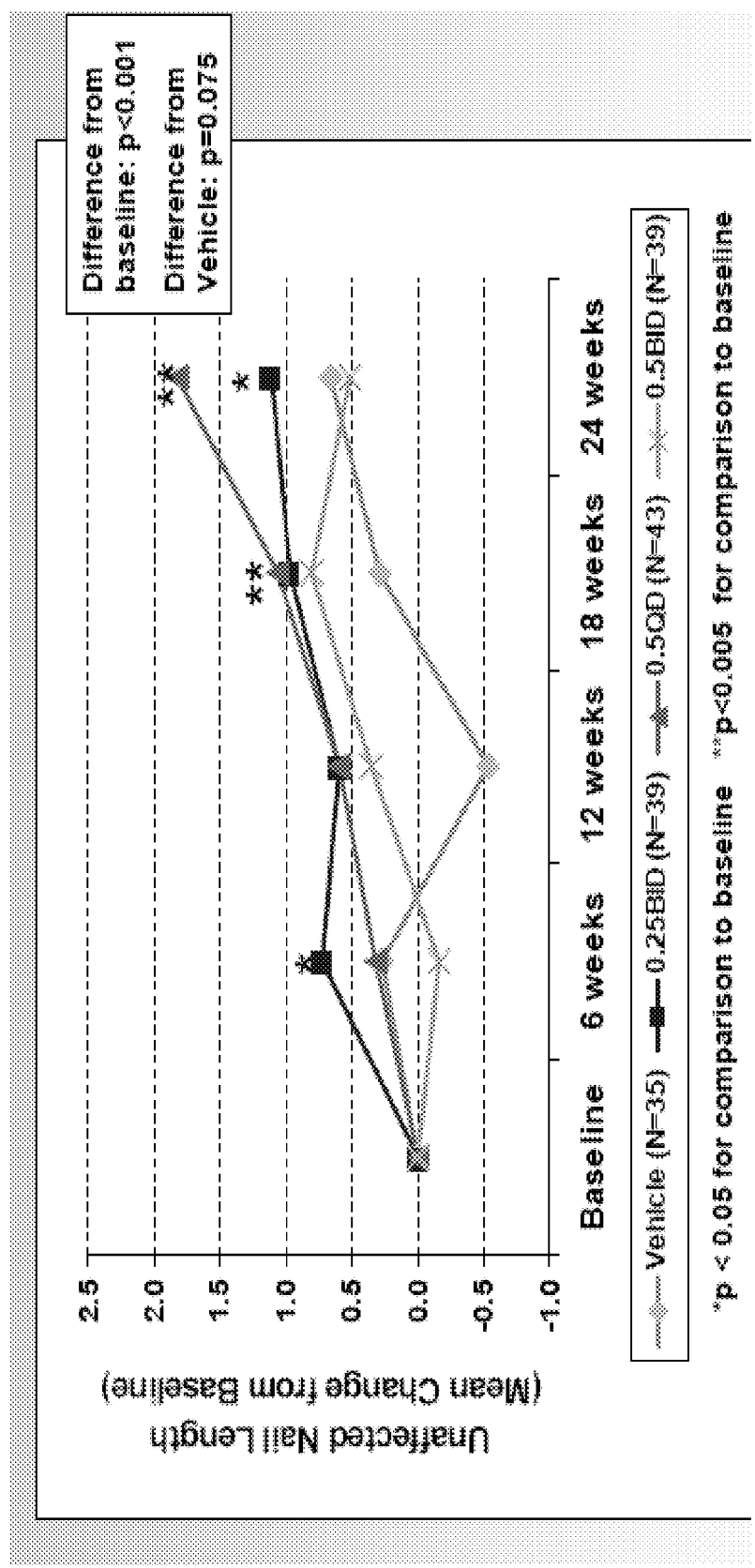
Figure 6: Change from Baseline in Unaffected Linear Nail Growth (Planimetric Assessment)

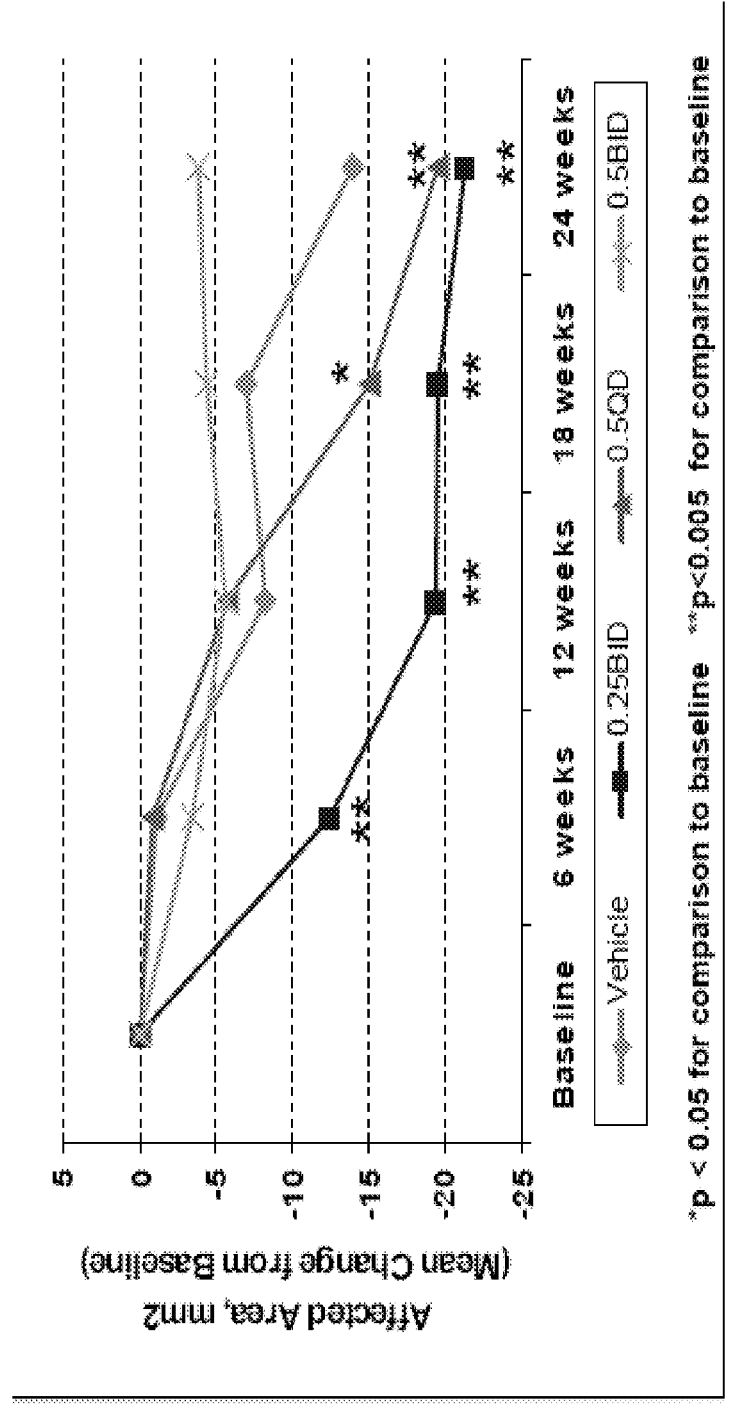
Figure 7: Interim Analysis of the Decrease in Affected Area (Planimetric Assessment)

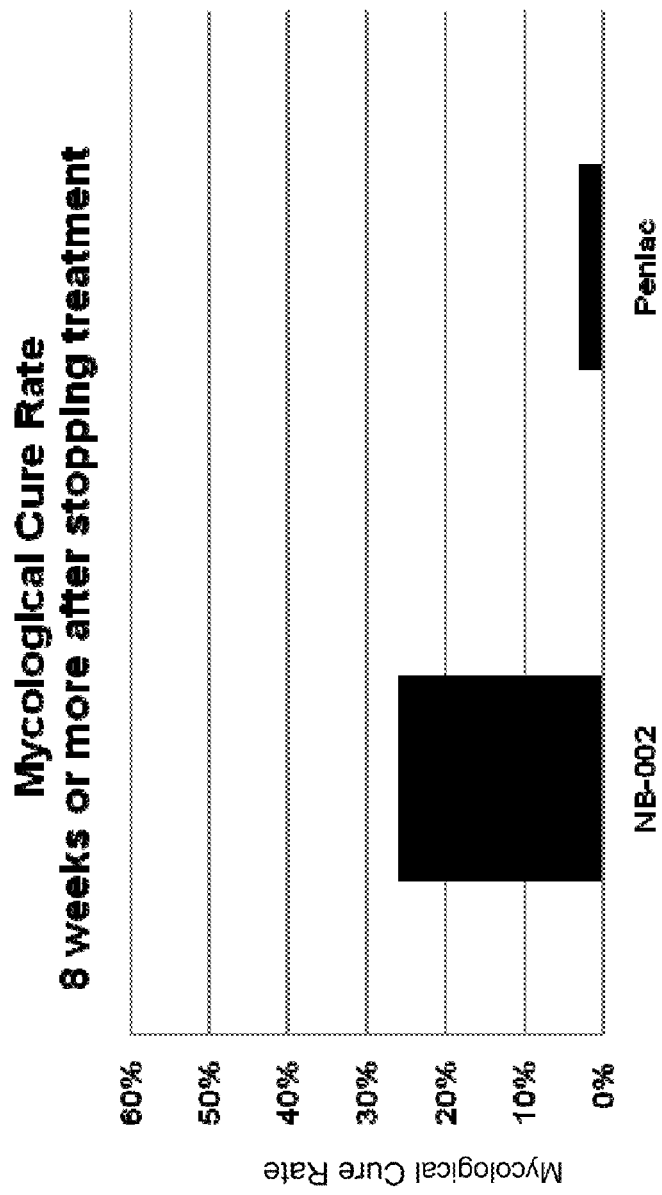
Figure 8: Comparison of Mycological Cure Rates for a Nanoemulsion ("NB-002") and Penlac Figure 9: Antifungal Activity of a Nanoemulsion (NB-002) Against Rare Fungal Pathogens

| Fungal Species | Isolate Number | MIC (μg/ml) | | | | |
| --- | --- | --- | --- | --- | --- | --- |
| | | Amphotericin B | Itraconazole | Terbinafine | Ciclopirox | NB-002 |
| Aspergillus sydowii | 07-3357 | 1 | 0.06 | 0.25 | 2 | 1 |
| Aspergillus terreus | 07-3047 | 4 | 0.5 | 0.25 | 1 | 1 |
| Aspergillus terreus | 07-1055 | 2 | 1 | 0.03 | 0.5 | 0.5 |
| Aspergillus niger | 07-585 | 1 | 1 | 0.03 | 1 | 1 |
| Aspergillus terreus | 06-4447 | 4 | 0.25 | 0.25 | 1 | 1 |
| Paecilomyces lilacinus | 08-505 | >16 | 2 | 0.25 | 16 | 8 |
| Paecilomyces lilacinus | 06-2728 | >16 | 1 | 0.5 | 8 | 4 |
| Paecilomyces lilacinus | 06-1287 | >16 | >8 | 0.5 | 8 | 2 |
| Paecilomyces lilacinus | 06-813 | >16 | 4 | 0.25 | 8 | 2 |
| Fusarium oxysporum | 06-3885 | 4 | >8 | >2 | 16 | 2 |
| Fusarium oxysporum | 06-1822 | 4 | >8 | >2 | 2 | 1 |
| Fusarium oxysporum | 06-1659 | >16 | >8 | >2 | 1 | 1 |
| Fusarium oxysporum | 05-3159 | 4 | >8 | >2 | 2 | 1 |
| Fusarium solani | 06-4076 | >16 | >8 | >2 | 16 | 0.5 |
| Fusarium solani | 06-3757 | 8 | >8 | >2 | 16 | 2 |
| Fusarium solani | 06-3305 | 16 | >8 | >2 | 16 | 2 |
| Fusarium solani | 06-3187 | 16 | >8 | >2 | 16 | 2 |
| Fusarium solani | 06-2748 | >16 | >8 | >2 | 16 | 1 |
| Fusarium semitectum | 06-3700 | 4 | 2 | 2 | 4 | 2 |
| Acremonium sp. | 07-3739 | >16 | >8 | 0.125 | 1 | 0.5 |
| Acremonium sp. | 06-3779 | 0.5 | >8 | 0.5 | 0.5 | 0.5 |
| Acremonium sp. | 06-1454 | 0.5 | >8 | 0.5 | 2 | 2 |
| Acremonium sp. | 06-528 | >16 | >8 | 1 | 0.5 | 1 |
| Chaetomium spp. | 06-434 | 0.5 | 0.5 | 2 | 0.25 | 0.25 |
| Chaetomium spp. | 07-1348 | 4 | 1 | 1 | 0.25 | 0.25 |
| Chaetomium spp. | 07-3907 | 2 | 0.5 | 1 | 0.5 | 0.25 |
| Phoma spp. | 07-3526 | 2 | 0.06 | 0.03 | 0.5 | 0.5 |
| Phoma spp. | 08-273 | 1 | 0.125 | 0.03 | 1 | 0.5 |
| Phoma spp. | 08-357 | 0.5 | 0.5 | 0.03 | 1 | 1 |

Figure 9. Continued

| Fungal Species | Isolate Number | Amphotericin B | Itraconazole | MIC (µg/ml) Terbinafine | Ciclopirox | NB-002 |
|---|---|---|---|---|---|---|
| Scopulariopsis spp. | 07-1812 | >16 | >8 | 1 | 1 | 1 |
| Scopulariopsis spp. | 06-619 | >16 | 4 | 1 | 2 | 1 |
| Scopulariopsis spp. | 06-481 | >16 | >8 | 1 | 1 | 1 |
| Scopulariopsis spp. | 07-3733 | >16 | >8 | >2 | 1 | 0.5 |
| Scopulariopsis spp. | 07-1404 | >16 | >8 | 1 | 0.5 | 0.5 |
| Scedosporium spp. | 08-554 | >16 | 4 | >2 | 8 | 1 |
| Scedosporium spp. | 08-521 | >16 | >8 | >2 | 2 | 0.5 |
| Scedosporium spp. | 08-262 | >16 | >8 | >2 | 2 | 1 |
| Scedosporium spp. | 08-81 | >16 | 4 | >2 | 0.5 | 0.5 |
| Scedosporium spp. | 08-151 | >16 | 4 | >2 | 1 | 0.25 |
| Scytalidium spp. | 07-3544 | 0.5 | >8 | 0.125 | 1 | 2 |
| Scytalidium spp. | 07-1362 | 0.5 | >8 | 1 | 0.5 | 1 |
| Scytalidium spp. | 07-845 | 1 | >8 | 1 | 0.5 | 1 |
| Scytalidium spp. | 06-4141 | 0.5 | >8 | 0.5 | 0.5 | 2 |
| Scytalidium spp. | 06-3588 | 1 | 4 | 0.5 | 0.5 | 1 |
| Scytalidium spp. | 06-1401 | 1 | >8 | 1 | 0.5 | 1 |
| Scytalidium spp. | 05-3338 | 0.5 | >8 | 1 | 0.5 | 1 |
| Scytalidium spp. | 05-2360 | 1 | >8 | 0.25 | 0.5 | 1 |
| Scytalidium spp. | 05-1145 | 1 | >8 | 0.5 | 0.5 | 1 |
| Scytalidium sp. | 05-401 | 1 | >8 | 0.5 | 0.5 | 1 |
| Scytalidium spp. | 07-3544 | 0.5 | >8 | 0.125 | 1 | 2 |
| Alternaria spp. | 07-3517 | 1 | 0.25 | 1 | 0.5 | 0.5 |
| Alternaria spp. | 07-2362 | 1 | 0.5 | 1 | 0.25 | 0.06 |
| Alternaria spp. | 07-795 | 1 | 0.25 | 2 | 0.25 | 0.06 |
| Epicoccum nigrum | R-3425 | 1 | 0.5 | 0.03 | 0.125 | 0.06 |
| Epicoccum nigrum | R-3590 | 0.25 | 0.25 | 0.03 | 2 | 1 |
| Epicoccum nigrum | 07-3518 | 0.5 | 0.25 | 0.06 | 2 | 1 |
| Curvularia spp. | 07-3740 | 0.125 | 0.125 | 1 | 1 | 0.5 |
| Curvularia spp. | 08-172 | 0.5 | 0.25 | 0.03 | 0.5 | 0.5 |
| Curvularia spp. | 08-959 | 1 | 0.125 | 0.06 | 0.5 | 0.5 |
| Trichophyton verrucosum | 03-3371 | 0.25 | 0.06 | <=0.004 | <=0.06 | <=0.03 |
| Trichophyton verrucosum | 04-2894 | 0.25 | 0.125 | 0.015 | 0.125 | 0.06 |
| Trichophyton verrucosum | 04-3299 | 0.125 | 0.125 | <=0.004 | 0.125 | 0.06 |
| Trichophyton soudanense | 07-1382 | 0.125 | 0.125 | <=0.004 | 0.125 | 0.06 |
| Trichophyton soudanense | 07-1614 | 0.25 | 0.25 | <=0.004 | 0.25 | 0.06 |
| Trichophyton soudanense | 07-2963 | 0.25 | 0.125 | <=0.004 | 0.125 | 0.06 |

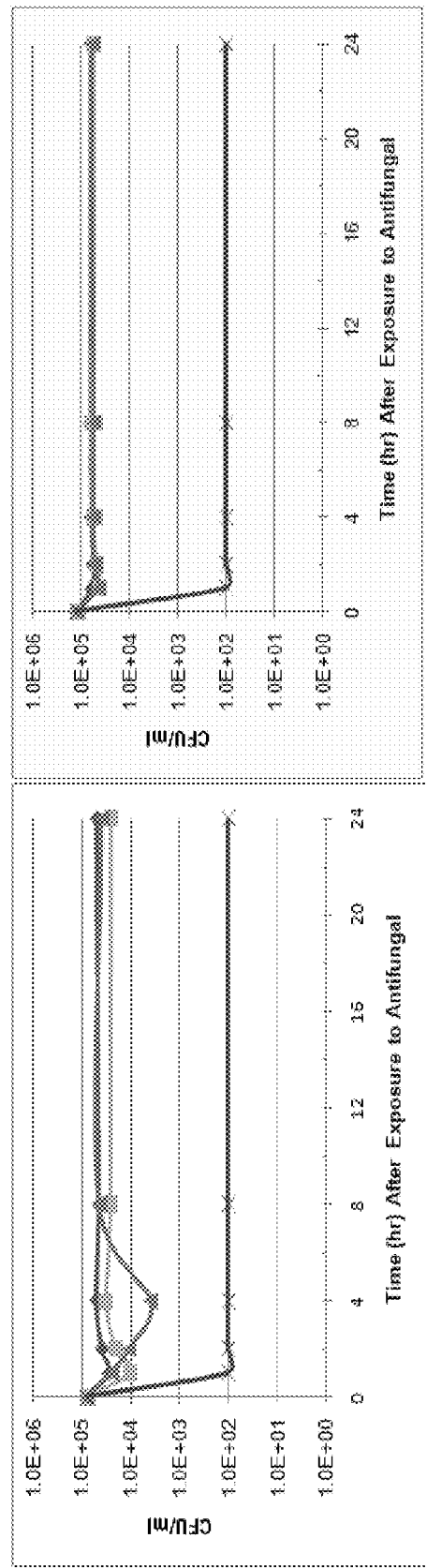
Figure 10. Impact of Nanoemulsions on the Viability of *T. rubrum*
Itraconazole (♦); terbinafine (■); cicl

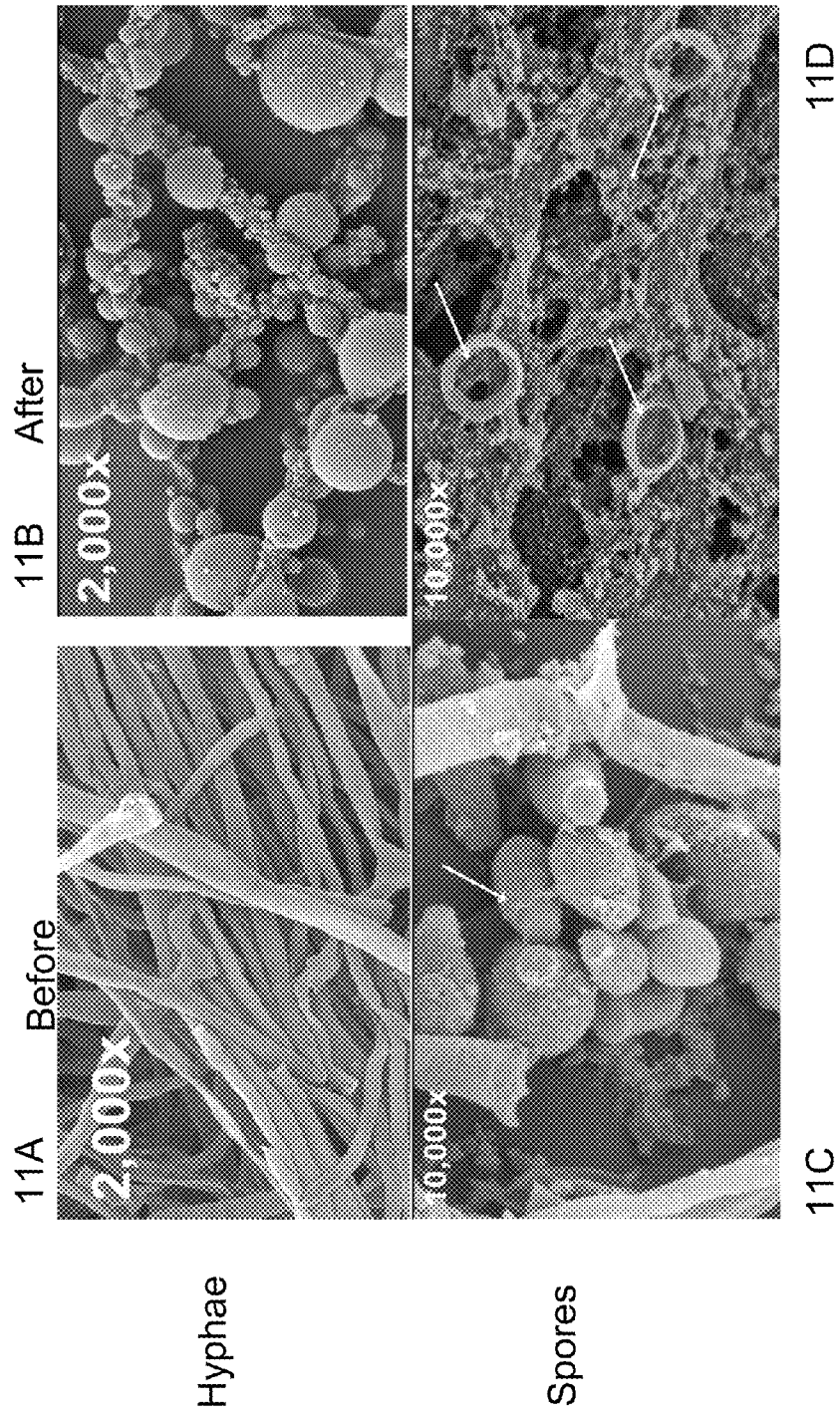
Figure 11. Nanoemulsions are Fungicidal Against *T. rubrum* Hyphae and Microconidial Spores Scanning electron microsocopy of NBD030 hyphae treated with a Nanoemulsion (NB-002) (~50x MIC) for 1 hour at room temperature (11,000x magnification)

Figure 13: Nanoemulsion Delivery into Human Cadaver Skin at 24 Hours

Epidermal Delivery

Dermal Delivery

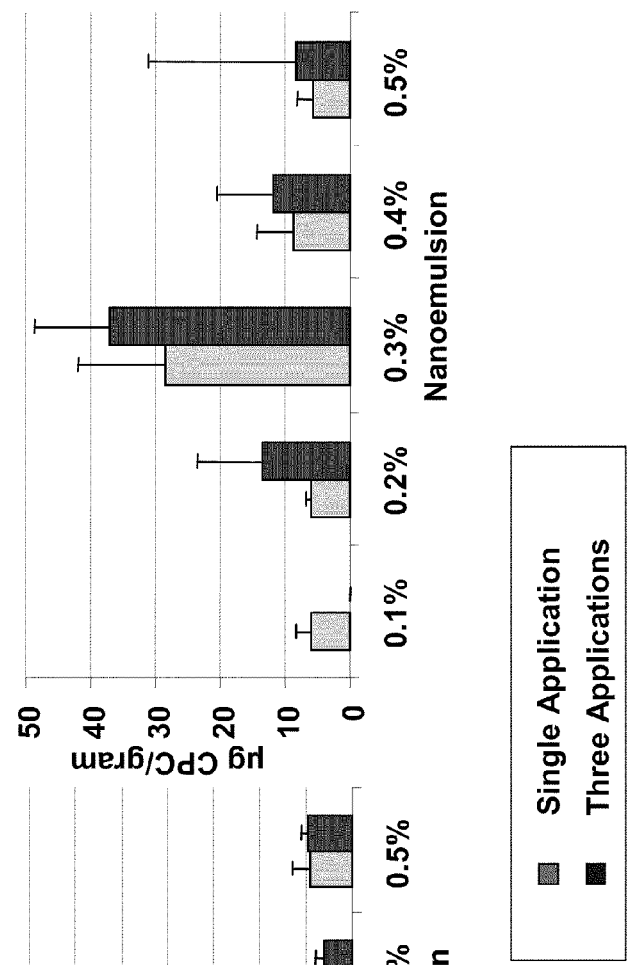
Figure 14: Effect of Nanoemulsion Dose on Delivery Into Pig Skin at 24 Hours
Fig. 14A Epidermal Delivery
Fig. 14B Dermal Delivery

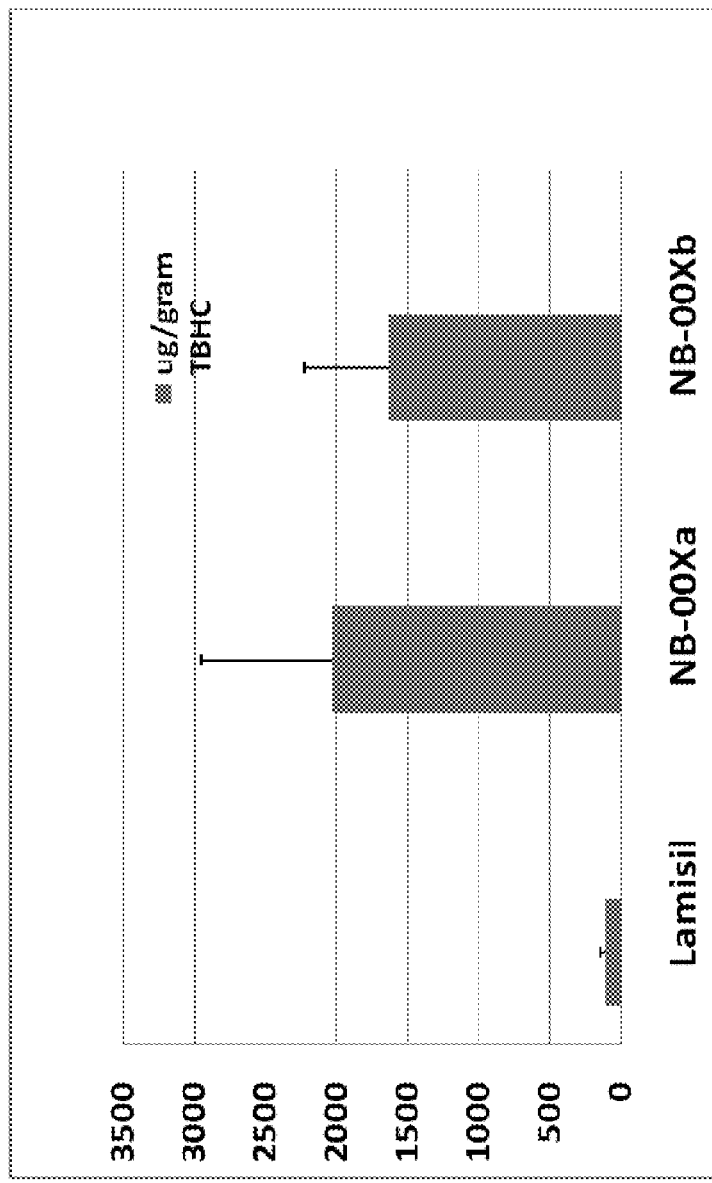
Figure 15. Levels of terbinafine hydrochloride in pig skin Epidermis (dorsal skin) at 24 hours after dosing (0 and 8 hours) with Lamisil® and two different nanoemulsion formulations.

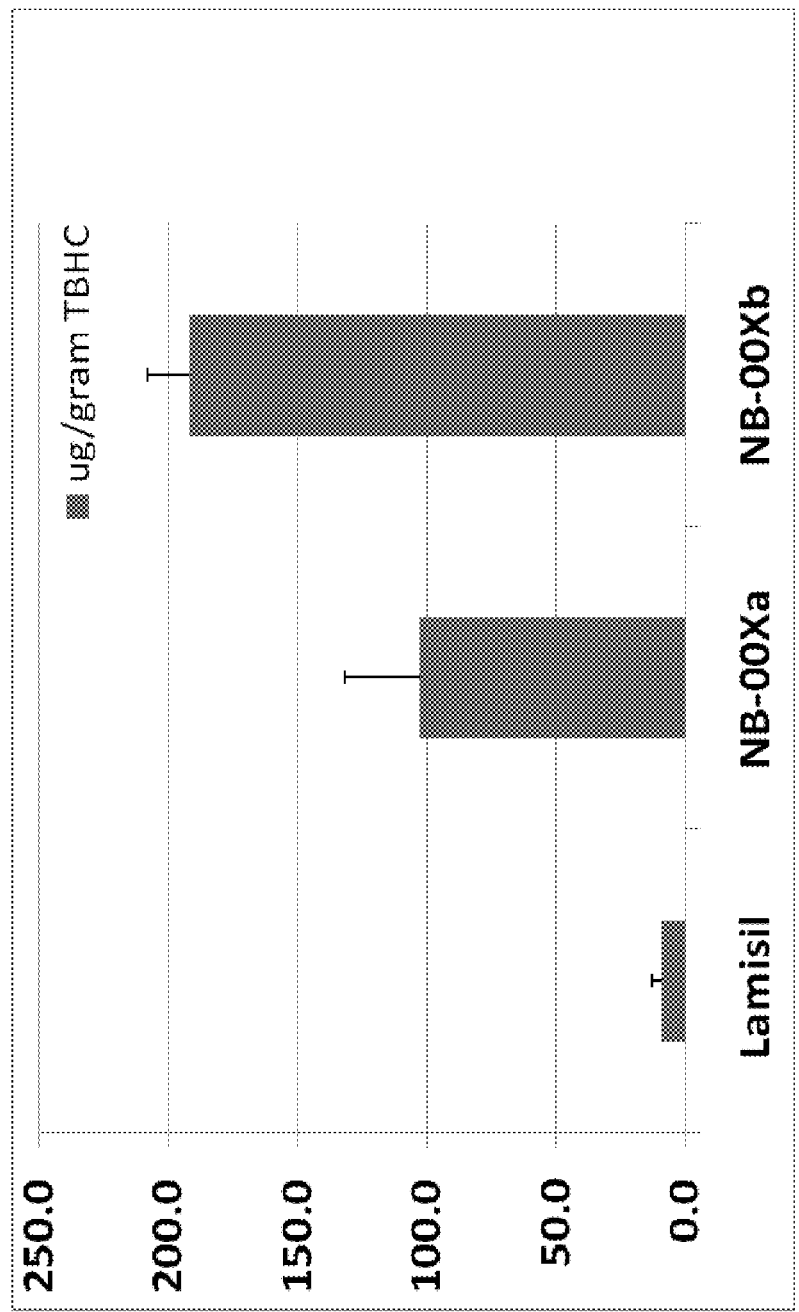
Figure 16. Levels of terbinafine hydrochloride in pig skin dermis (dorsal skin) at 24 hours after BID dosing (0 and 8 hours) with Lamisil® and two different nanoemulsion formulations.

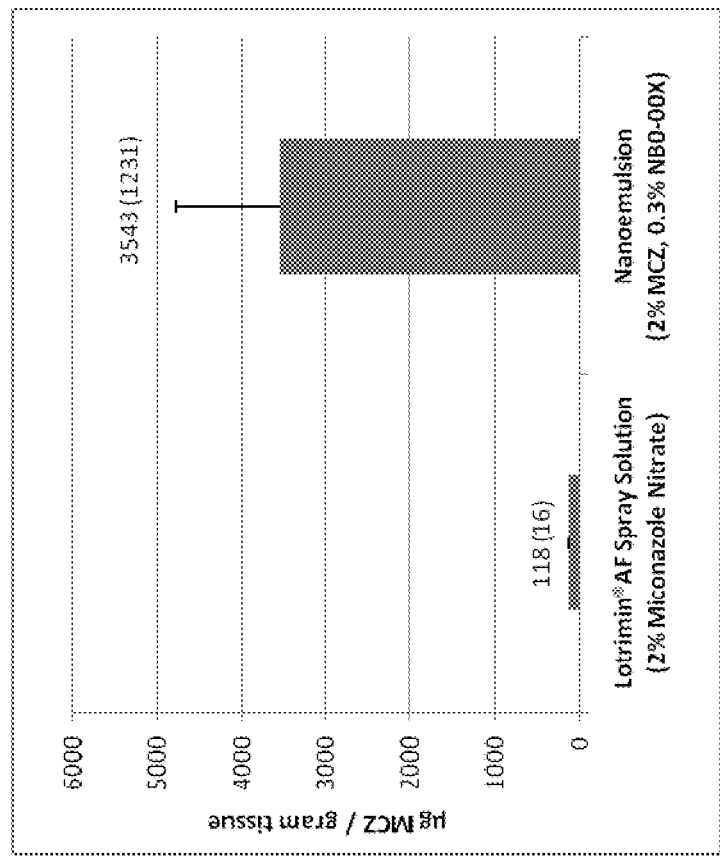
Figure 17. Levels of Miconazole in swine skin epidermis at 24 hours after topical application (BID).

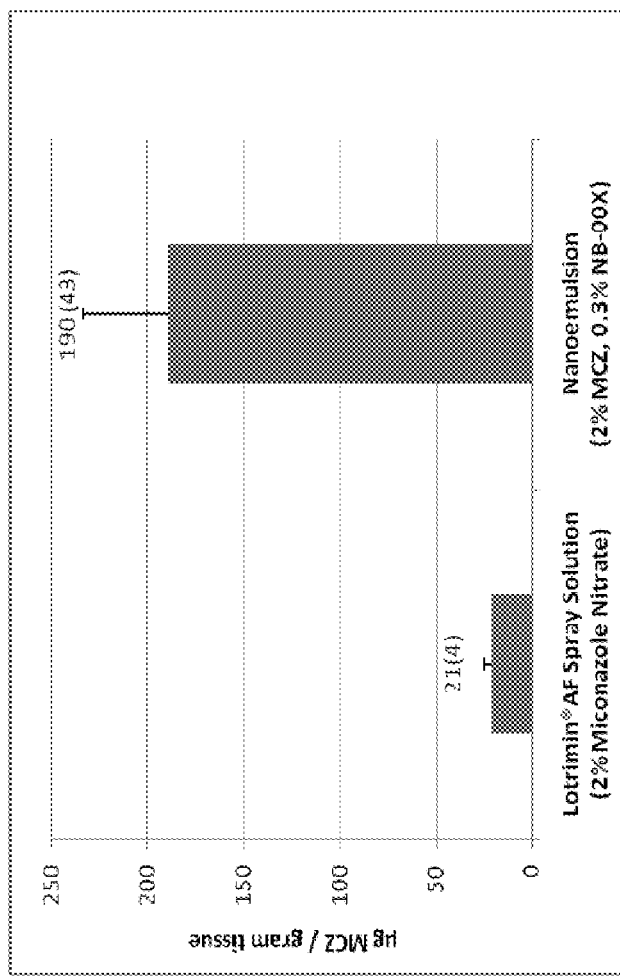
Figure 18. Levels of Miconazole in swine skin dermis at 24 hours after topical application (BID).

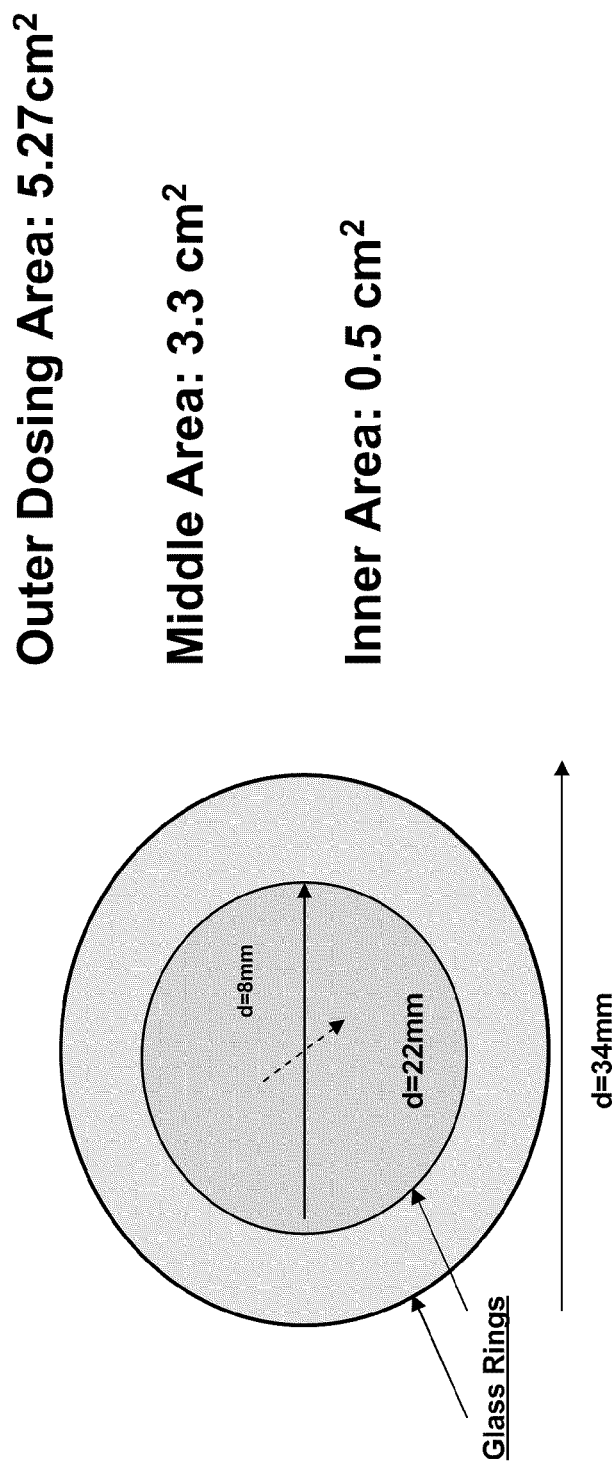
Figure 19: Drug Delivery: Lateral Diffusion Studies

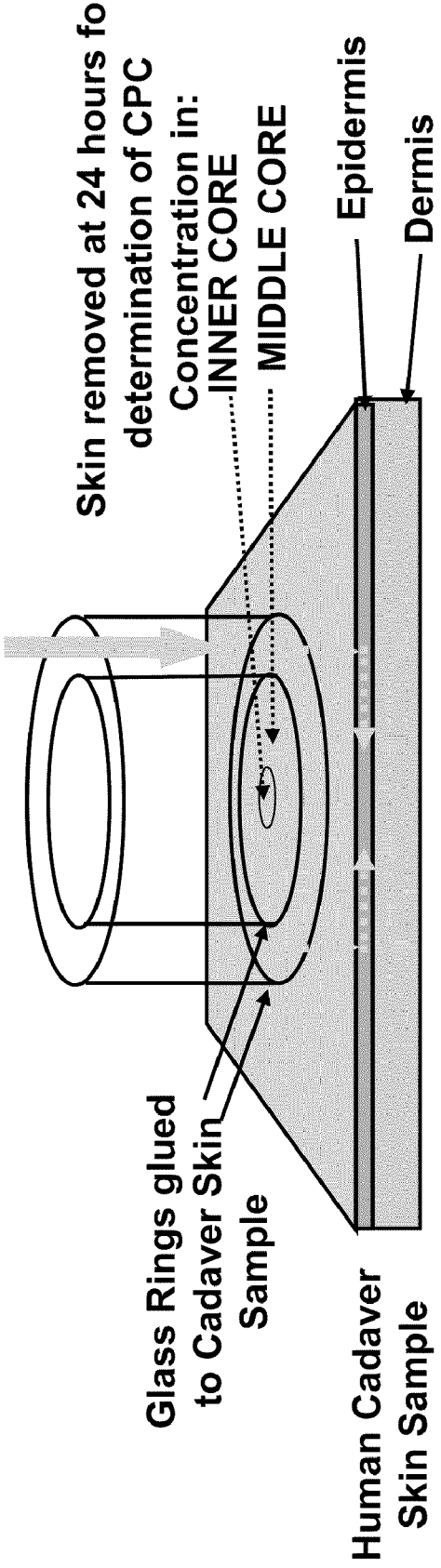
Figure 20: Lateral Diffusion Study in Human Cadaver Skin

Figure 21: Lateral Diffusion into Human Cadaver Epidermis Skin at 24 Hours
Fig. 21B  0.5% Nanoemulsion
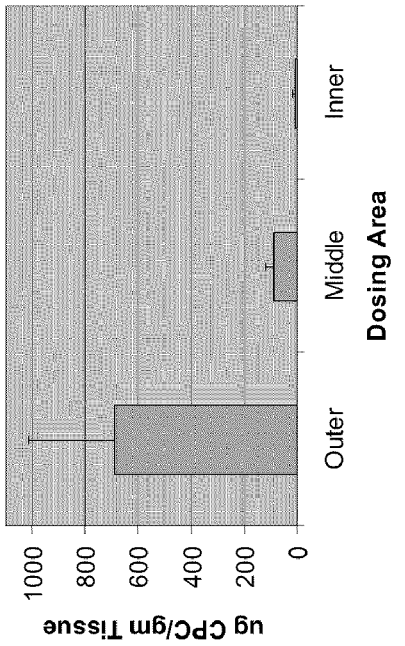
Fig. 21A  0.5% Micellar CPC
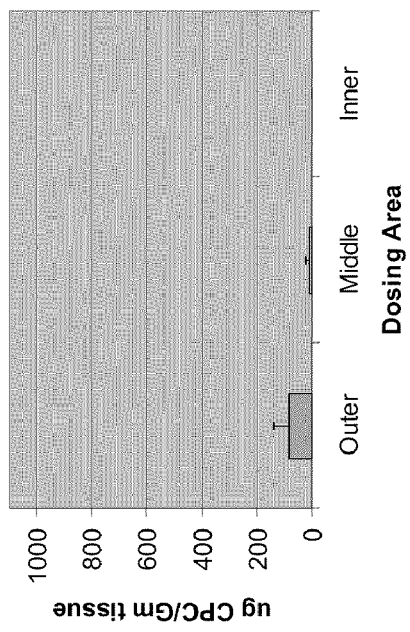

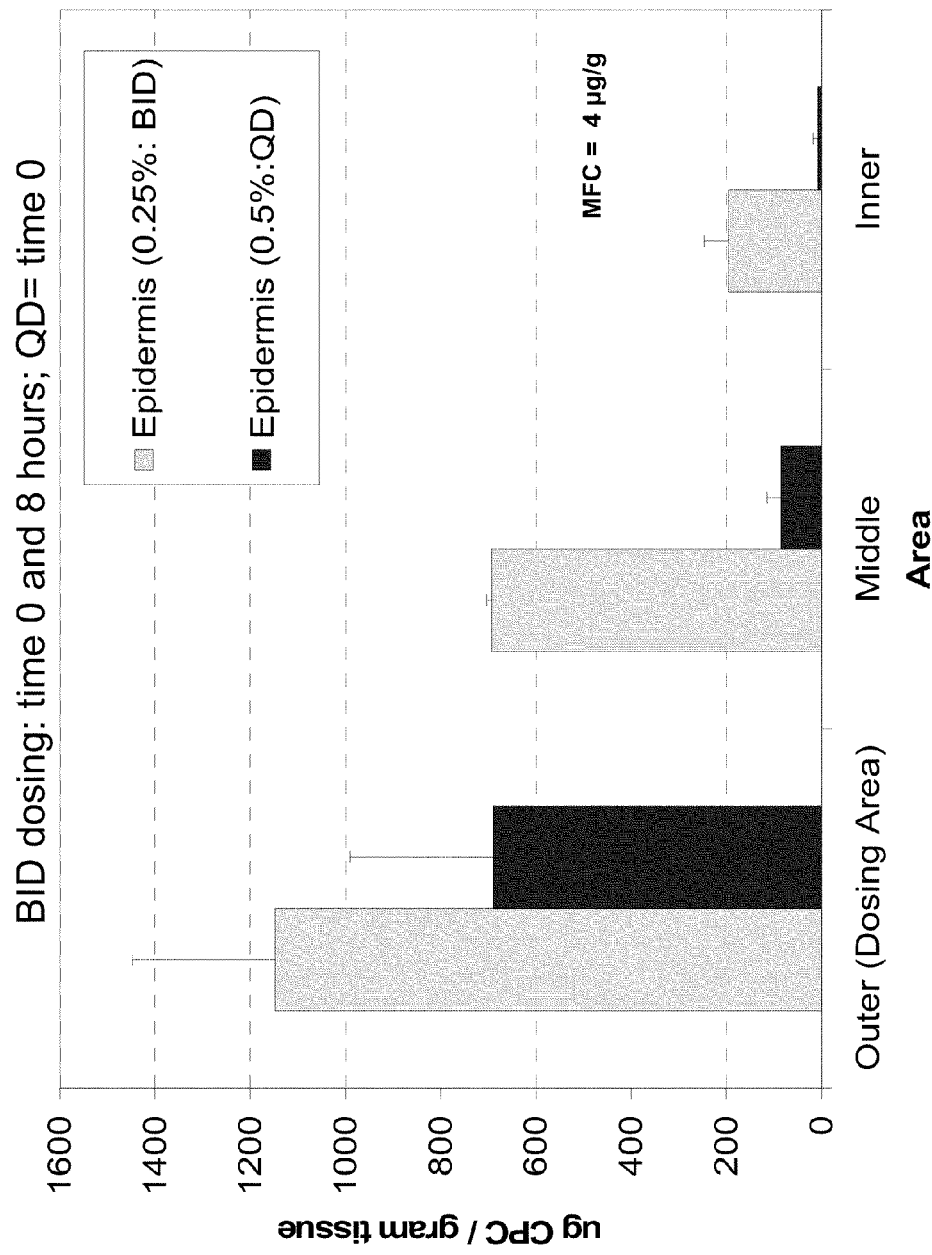
Figure 22: Transport of Nanoemulsion Within Epidermal Tissue

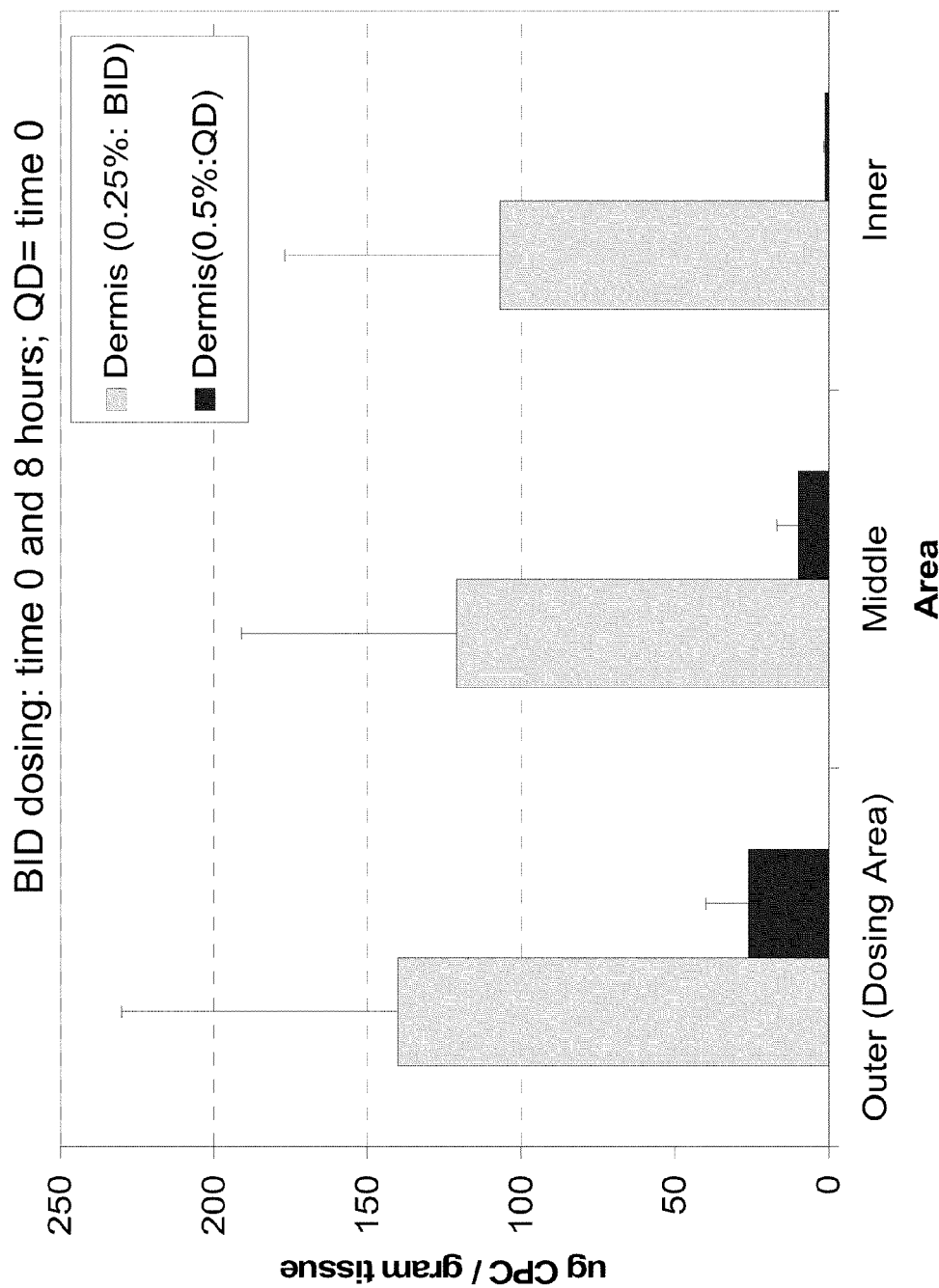
Figure 23: Transport of Nanoemulsion Within Dermal Tissue

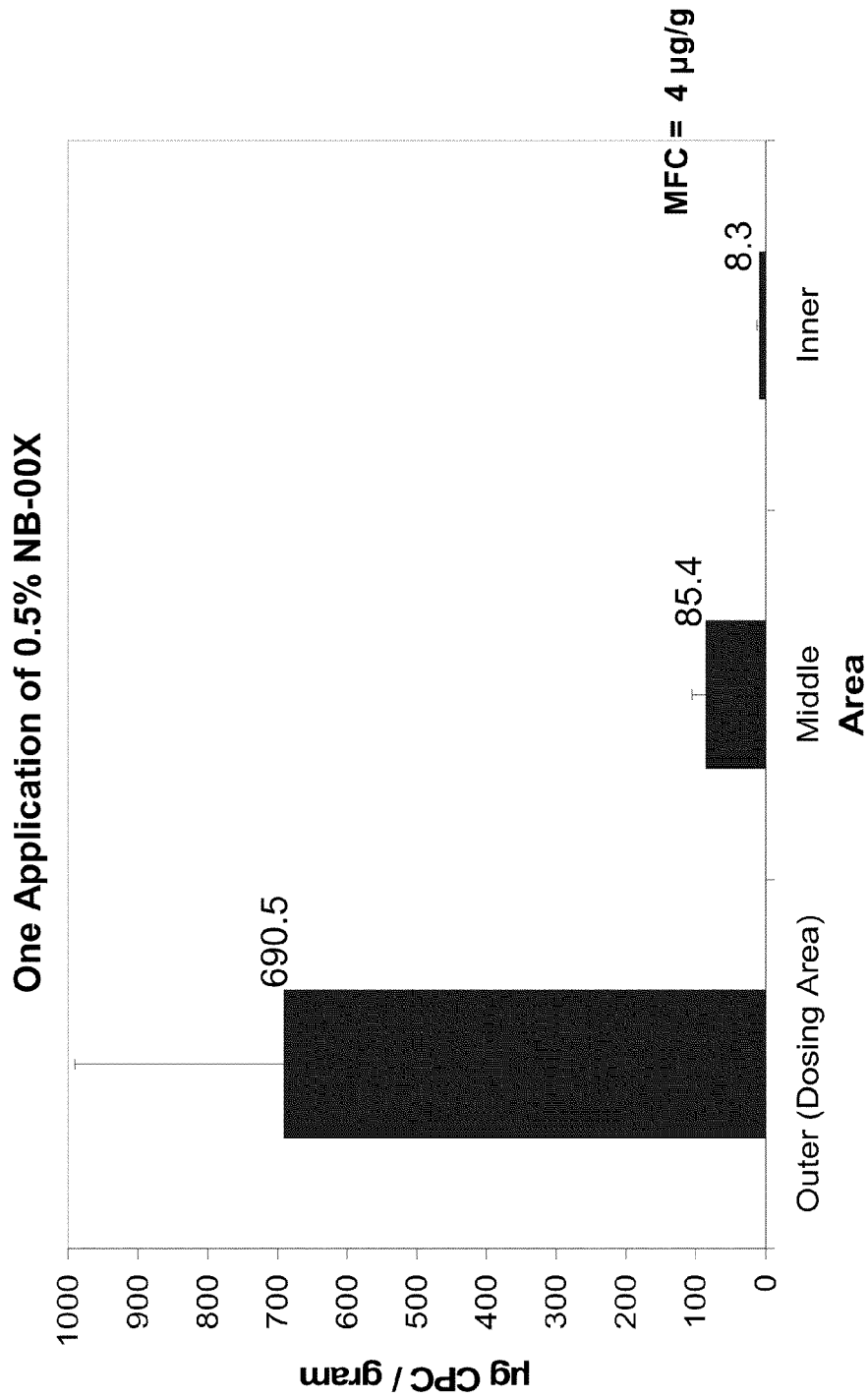
Figure 24: Nanoemulsion (CPC) within Epidermis 24 hours Post-application

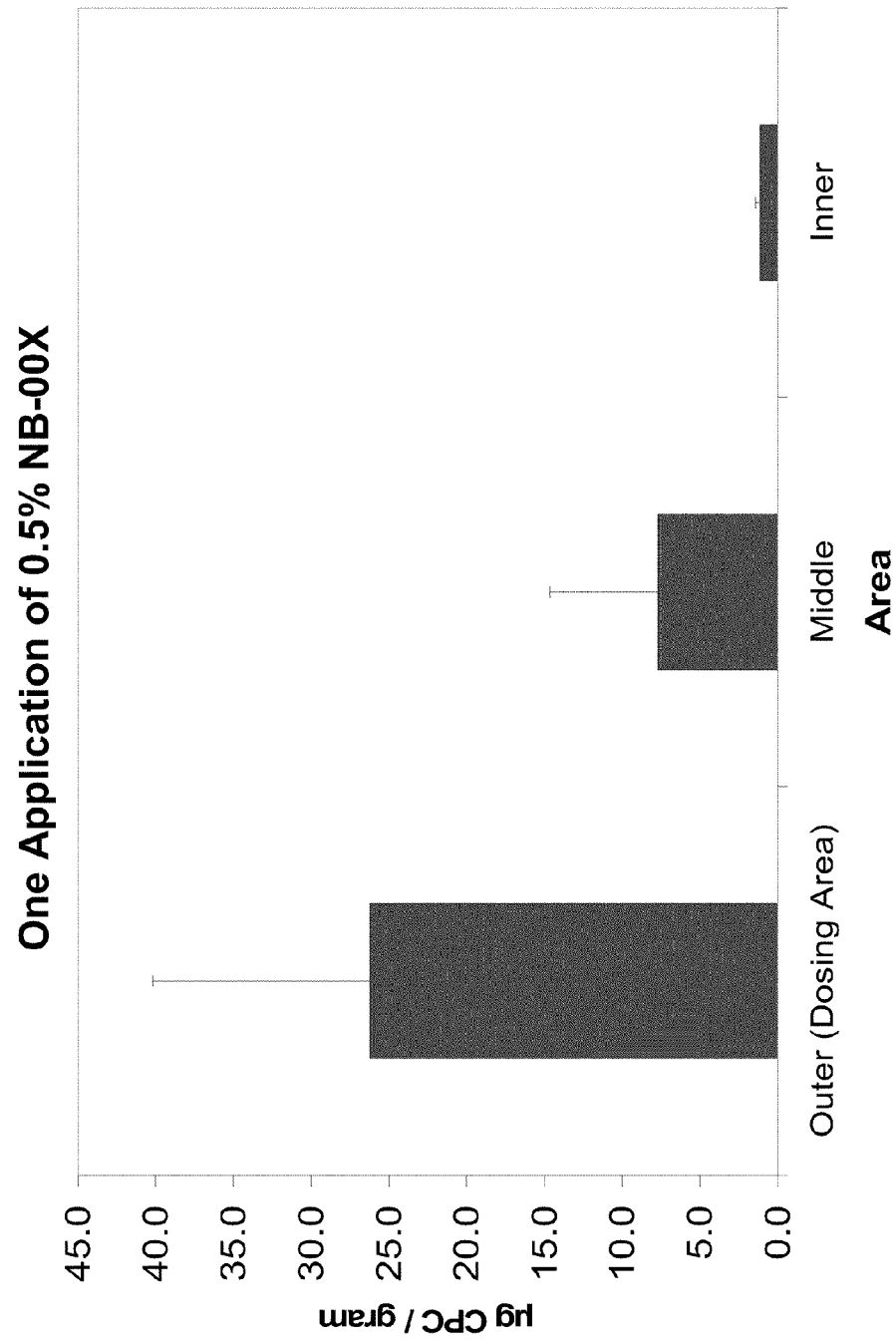
Figure 25: Nanoemulsion (CPC) within Dermis 24 hours Post-application

METHODS OF TREATING FUNGAL, YEAST AND MOLD INFECTIONS

CROSS-REFERENCE TO RELATED APPLICATIONS

This application claims priority of U.S. Provisional Patent Application No. 61/048,075, filed on Apr. 25, 2008; U.S. Provisional Patent Application No. 61/129,962, filed on Aug. 1, 2008; and U.S. Provisional Patent Application No. 61/115,879, filed on Nov. 18, 2008. The contents of these applications are incorporated herein by reference in their entirety.

FIELD OF INVENTION

The present invention relates to methods for treating, killing, and/or inhibiting the growth of fungal, yeast, and mold pathogens in human subjects comprising topically administering to a human subject in need thereof a nanoemulsion composition having antifungal, anti-yeast, and/or anti-mold properties. The present invention also relates to methods for treating, preventing, and/or completely curing fungal, yeast, and/or mold infections in human subjects comprising topically administering to a human subject in need thereof a nanoemulsion composition having antifungal, anti-yeast, and/or anti-mold properties.

BACKGROUND OF THE INVENTION

A. Fungal/Yeast/Mold Infections

Fungi cause a wide variety of diseases in humans. While some fungi cause infections limited to the outermost layers of the skin and hair (superficial mycoses), other fungi cause cutaneous mycoses by penetrating to the keratinized layers of the skin, hair and nails and triggering pathologic changes in the host. Subcutaneous mycoses cause infections in the dermis, subcutaneous tissues, muscle and fascia and are often chronic. Systemic mycoses originate primarily in the lung and may cause secondary infections in other organ systems in the body. Patients with immune system deficiencies are often prone to opportunistic mycoses.

Dermatophytes, including *Trichophyton rubrum* and *Trichophyton mentagrophytes*, are responsible for fungal infections of the skin or Dermatophytoses (dermatophytose). *Tinea pedis* is a skin infection that most often manifests between the toes, causing scaling, flaking and itching of the affected skin. Blisters and cracked skin may also occur, leading to exposed raw tissue, erythema, pain, swelling and inflammation. A second type of *tinea pedis* is called the moccasin *tinea pedis* and is characterized by chronic plantar erythema with slight scaling to diffuse hyperkeratosis that can be asymptomatic or pruritic. Other types include inflammatory/vesicular and ulcerative *tinea pedis*. The infection can be spread to other areas of the body, and manifest itself in the form of annular scaly plaques with raised edges, pustules, and vesicles in the trunk and arms and legs (*Tinea corporis*), scaly rash in the palms and finger webs (*Tinea manuum*), erythematous lesions in the groin and pubic region (*Tinea cruris*), erythema, scaling, and pustules in the beard and neck area (*Tinea barbae* or *Tinea faciale*), or round, bald, scaly patches in the scalp (*Tinea capitis*). *Tinea versicolor*, also called pityriasis versicolor, is a common fungal infection of the skin that interferes with the normal pigmentation of the skin, resulting in small, discolored patches. *Tinea unguium* is another term for dermatophyte infections of the nail. Secondary bacterial infections may develop from the fungal infection.

*Tinea* is very common, especially among children, and may be spread by skin-to-skin contact, as well as via contact with contaminated items such as hairbrushes or through the use of the same toilet seat as an infected individual. *Tinea* spreads readily, as those infected are contagious even before they show symptoms of the disease. Participants in contact sports such as wrestling have a risk of contracting the fungal infection through skin-to-skin contact.

*Tinea* is mildly contagious. *Tinea* is also a common infection in domestic animals, especially farm animals, dogs and cats and even small pets like hamsters or guinea pigs. Humans can contract *tinea* (also commonly referred to as "ringworm") from these animals as humans are in close contact with them. *Tinea* can also be caught from other humans, both by direct contact and by prolonged contact with flakes of shed skin (from sharing clothes or from house dust, for instance).

The best known sign of *tinea* in people is the appearance of one or more red raised itchy patches with defined edges, not unlike the herald rash of *Pityriasis rosea*. These patches are often lighter in the center, taking on the appearance of a ring with hyperpigmentation around the circumference caused by an increase in melanin. If the infected area involves the scalp or beard area, then bald patches may become evident. The affected area may become itchy for periods of time.

Sometimes a *tinea* infection may cause skin lesions in a part of the body that is remote from the actual infection. Such lesions are called "dermatophytids". The lesions themselves are fungus-free, and normally disappear upon treatment of the actual infection. The most common example is an eruption in the hands resulting from a fungus infection of the feet. Dermatophytids are essentially a generalized allergic reaction to the fungus.

Thus, fungi and yeast such as *Microsporum* species, *Trichophyton* species, *Epidermophyton* species, and *Candida* species can cause persistent and difficult to treat infections.

Examples of *Microsporum* species include *M. canis* and *M. gypseum*. *Microsporum* is one of the several fungal genera that cause dermatophytosis. Dermatophytosis is a general term used to define the infection in hair, skin or nails due to any dermatophyte species. Similar to other dermatophytes, *Microsporum* has the ability to degrade keratin and thus can reside on skin and its appendages and remains noninvasive. Notably, *Microsporum* spp. mostly infect the hair and skin. *Microsporum canis* is the principal cause of ringworm in dogs and cats and a zoophilic fungal species causing sporadic dermatophytosis in humans, especially *tinea capitis* in children with cats and dogs.

Skin infection by a *Trichophyton* species occurs mainly on the back of the neck, scalp or beard. Symptoms of a *Trichophyton* species infection include inflamed scalp lesions, inflamed neck lesions, inflamed beard lesions, scarring, and permanent hair loss. Examples of *Trichophyton* species include *T. rubrum*, *T. tonsurans* and *T. mentagrophytes*.

*Trichophyton tonsurans* is an anthropophilic endothrix species of fungi that causes epidemic dermatophytosis in Europe, South America, and the U.S. It infects some animals and requires thiamine for growth. It is the most common cause of *tinea capitis* in the U.S., forming black dots where hair breaks off at the skin surface. *Trichophyton rubrum* is a fungus that is the most common cause of *tinea pedis* ("athlete's foot"), *tinea cruris*, and *tinea* (ringworm). *Trichophyton rubrum* is the most common of the dermatophytes causing fingernail fungus infections. While most fungal skin infections are irritating and difficult to treat, there are reports of fungal infections resulting in death. Specifically, a *Trichophyton mentagrophytes* skin infection migrated to the lymph nodes, testes, vertebrae and CNS. Treatment with griseofulvin, amphotericin B, clotrimazole, and transfer factor failed, eventually resulting in death of the subject (Hironaga et al., *J. Clin. Microbiol.*, 2003; 5298-5301.) *Trichophyton mentagrophytes* is the second most common source of fungal nail infections from the dermatophyte group.

The genus *Epidermophyton* contains two species; *Epidermophyton floccosum* and *Epidermophyton stockdaleae*. *E. stockdaleae* is known to be nonpathogenic, leaving *E. floccosum* as the only species causing infections in humans. *E. floccosum* is one of the common causes of dermatophytosis in otherwise healthy individuals. It infects skin (*tinea corporis, tinea cruris, tinea pedis*) and nails (onychomycosis). The infection is restricted to the nonliving cornified layers of epidermis since the fungus lacks the ability to penetrate the viable tissues of the immunocompetent host. Disseminated infections due to any of the dermatophytes are very unlikely due to the restriction of the infection to keratinized tissues. However, invasive *E. floccosum* infection has been reported in an immunocompromised patient with Behcet's syndrome. As with all forms of dermatophytosis, *Epidermophyton floccosum* infections are communicable and usually transmitted by contact, particularly in common showers and gym facilities.

Examples of *Candida* species include *C. albicans, C. parapsiliosis,* and *C. krusei*. Patients with chronic mucocutaneous candidiasis may develop candidal infection of the nails. *Candida* species may invade nails previously damaged by infection or trauma and cause infection in the periungual area and underneath the nailbed. The nailfold becomes erythematous, swollen and tender with an occasional discharge. The disease causes loss of the cuticle, nail dystrophy, and onycholysis with discoloration around the lateral nailfold. In all forms of onychomycosis, the nail becomes variously disfigured and distorted.

A specific example of a fungal infection caused by the fungi and yeasts discussed above is onychomycosis (nail infection). Fungal infections affecting the nails or scalp are very difficult to treat due to fungal infection in follicle roots or under the nail itself.

Onychomycosis is a chronic, persistent fungal, yeast, and/or mold infection of the nail bed which causes thickening and discoloration of the nail, sometimes accompanied by pain and disability. This fungal infection affects 25% of adults, and the incidence rises with age, such that the prevalence in adults over 50 years of age is 40%. According to a study reported in *Podiatry Today*, over 35 million people in the United States have onychomycosis, and up to 50% of those affected by the disease do not receive treatment.

Onychomycosis has significant effects on a patient's social, occupational and emotional functioning. Feeling of embarrassment may preclude patients from interacting in a social or working environment where they are unwilling to show their hands or feet. Moreover, immunocompromised hosts affected by onychomycosis are especially at risk of developing secondary bacterial infections.

Onychomycosis (nail infection) may be caused by a dermatophyte, yeast, or nondermatophyte mold. Onychomycosis is caused primarily by the dermatophytes including *Trichophyton* spp., *Epidermophyton* spp., and *Microsporum* spp. In particular, onychomycosis may be caused by the dermatophytes *Trichophyton rubrum* (90%), *Trichophyton mentagrophytes, Epidermophyton floccosum, Microsporum audouinii, Microsporum canis, Microsporum gypseum, Trichophyton verrucosum, Trichophyton violaceum, Trichophyton schoenleinii, Trichophyton tonsurans*, and molds, such as *Acremonium* spp., *Aspergillus* spp., *Fusarium* spp., *Scopulariopsis brevicaulis, Alternia* spp., *Paecilomyces lilacinus, Epiccocum nigrum, Phoma* spp., *Chaetomium* spp., *Curvularia* spp., *Scedosporium* spp., *Onychocola canadensis* and *Scytalidium* dimidiatum. *Candida* spp. cause 51-70% of fingernail infections.

Distal subungual onychomycosis (DSO), the most common form of onychomycosis, may develop in the toenails, fingernails or both. The infection begins with the invasion of the hyponychium, where the nail separates from the nail bed, and causes the separation of the nail plate from the nail bed (onycholysis) and thickening of subungueal area. When superinfection with bacteria and/or molds occurs, the nail plate turns yellowish brown.

Proximal subungual onychomycosis (PSO) is very frequent in AIDS patients. The fungus invades the proximal nail fold and penetrates into the newly forming nail plate that is underneath. The distal nail remains normal until late in the disease. The infection causes thickening of the skin (subungual hyperkeratosis), whitening of the nail (leukonychia), proximal onycholysis, and destruction of the nail unit.

White superficial onychomycosis (WSO) is a less common form of onychomycosis that begins at the superficial layer of the nail plate and progressively invades deeper layers. Total dystrophic onychomycosis is the final stage in all types of onychomycosis.

In addition, *Candida* species, and *Candida albicans* in particular, play an etiologic role in the development of chronic paronychia, a common infection of the soft tissue around the fingernail or toenail, where bacteria may act as co-pathogens. Swollen, erythematous and tender nail folds without fluctuance are characteristic of chronic paronychia. Eventually, the nail plates become thickened and discolored, with pronounced transverse ridges and the cuticles and nail folds may separate from the nail plate, forming a space for the invasion of various microorganisms.

Onychomycosis has long been one of the most difficult fungal infections to treat. The length of time it takes the nail to grow, the impenetrability of the nail plate, and location of the infection between the nail bed and plate are major factors interfering with the eradication of fungal agents affecting these tissues. Thus, eradication of symptoms is very slow and may take a whole year or even longer. Topical antifungals have low efficacy because of their antifungal spectrum may be limited to dermatophytes and because of restricted penetration of the antifungal agent across the nail. Systemic treatment with antifungal agents has shown relapse rates of 40% or higher, and have significant risks, including hepatic and/or cardiac toxicity, and adverse drug interactions. Thus, there is a significant need for alternative, and more effective, methods of treating fungal, yeast, and/or mold infections such as onychomycosis.

B. Conventional Treatment Options for Fungal, Yeast, and Mold Infections

Conventional treatment for fungal, yeast, and mold infections include topical and oral drugs. Orally administered drugs are generally more effective than topically applied drugs, but because they act systemically rather than locally, the side effects of orally administered drugs can be much more severe.

Examples of orally administered antifungal drugs include, but are not limited to, griseofulvin, imidazoles (bifonazole, clomidazole, clotrimazole, econazole, fenticonazole, ketoconazole, isoconazole, miconazole, oxiconazole, sertaconazole, sulconazole, tioconazole), triazole (fluconazole, itraconazole, posaconazole, voriconazole), terbinafine, and benzimidazole (thiabendazole). A detailed description of a few of these drugs is provided.

Griseofulvin (Fulvicin-U/F®, Grifulvin V®, and Gris-PEG®) is an orally administered drug used to treat *tinea* in both animals and people, including skin infections such as *tinea cruris, tinea pedis*, and *tinea*; and fungal infections of the scalp, fingernails, and toenails (onycchomycosis).

Griseofulvin comes as a tablet, capsule, and liquid to take by mouth. It is usually taken once a day or can be taken two to four times a day. Although symptoms may get better in a few days, the drug must be taken for 2 to 4 weeks for skin infections, 4 to 6 weeks for hair and scalp infections, 4 to 8 weeks for foot infections, 3 to 4 months for fingernail infections, and at least 6 months for toenail infections. Examples of griseofulvin side effects include hives, skin rashes, confusion, dizziness and/or faintness, diarrhea, thirst, fatigue, headache, impairment of performance of routine activities, inability to fall or stay asleep, nausea and/or upset stomach, oral thrush (yeast infection of the mouth), upper abdominal pain, vomiting, swelling, itching, tingling in the hands or feet, loss of taste sensation, and sensitivity to alcohol. In addition, griseofulvin may possibly a teratogen inducing mutations and can reduce the effectiveness of oral contraceptives.

Terbinafine hydrochloride (Lamisil®, Terbisil®, Zabel®) is a synthetic allylamine antifungal. It is highly lipophilic in nature and tends to accumulate in skin, nails, and fatty tissues. Terbinafine is mainly effective on the dermatophytes group of fungi. As a 1% cream or powder it is used for superficial skin infections such as *Tinea cruris, Tinea pedis* and other types of *tinea* (ringworm). Oral 250 mg tablets are often prescribed for the treatment of onychomycosis of the toenail or fingernail due to the dermatophyte *Tinea unguium*. Fungal nail infections can be located deep under the nail in the matrix to which topically applied treatments are unable to penetrate in sufficient amounts. Terbinafine tablets to take by mouth are usually taken once a day for 6 weeks for fingernail fungus and once a day for 12 weeks for toenail fungus. The tablets may cause hepatoxicity, so patients are warned of this and may be monitored with liver function tests. In addition, terbinafine hydrochloride may induce or exacerbate Subacute Cutaneous Lupus Erythematosus. Itraconazole capsules can be used to treat fungal infections of the fingernails and/or toenails. Itraconazole oral solution is used to treat yeast infections of the mouth and throat and suspected fungal infections in patients with fever and certain other signs of infection. Itraconazole is in a class of antifungals called azoles. It works by inhibiting ergosterol biosynthesis, an essential component of the fungal membrane.

Itraconazole comes as a capsule and a solution (liquid) to take by mouth. Itraconazole capsules are usually taken with a full meal one to three times a day for at least 3 months. When itraconazole capsules are used to treat fungal infections of the fingernails, they are usually taken twice a day for one week, not taken at all for three weeks, and then taken twice a day for an additional week. Itraconazole solution is usually taken on an empty stomach once or twice a day for 1 to 4 weeks or longer. If itraconazole is being taken to treat a nail infection, the nails will probably not look healthier until new nails grow. It can take up to 6-9 months to grow a new fingernail and up to 12-18 months to grow a new toenail.

Itraconazole has many serious side effects. For example, itraconazole can cause congestive heart failure (condition in which the heart cannot pump enough blood through the body). Other side effects include diarrhea or loose stools, constipation, gas, stomach pain, heartburn, sore or bleeding gums, sores in or around the mouth, headache, dizziness, sweating, muscle pain, decreased sexual desire or ability, nervousness, depression, runny nose and other cold symptoms, unusual dreams, excessive tiredness, loss of appetite, upset stomach, vomiting, yellowing of the skin or eyes, dark urine, pale stools, tingling or numbness of the hands or feet, fever, chills, or other signs of infection, frequent or painful urination, uncontrollably shaking hands, rash, hives, itching, and difficulty breathing or swallowing. In addition, one of the ingredients in itraconazole oral solution caused cancer in some types of laboratory animals. It is not known whether people who take itraconazole solution have an increased risk of developing cancer.

Ketoconazole (Nizoral®) comes as a tablet to take by mouth. It is usually taken once a day. Ketoconazole is used to treat fungal infections. Ketoconazole is most often used to treat fungal infections that can spread to different parts of the body through the bloodstream such as yeast infections of the mouth, skin, urinary tract, and blood, and certain fungal infections that begin on the skin or in the lungs and can spread through the body. Ketoconazole is also used to treat fungal infections of the skin or nails that cannot be treated with other medications. Ketoconazole is in a class of azole antifungals. It works by slowing the growth of fungi that cause infection.

Ketoconazole may cause liver damage. In addition, other side effects associated with ketoconazole include stomach pain, depression, rash, hives, itching, difficulty breathing or swallowing, and suicidal tendencies. In addition, a small number of patients who were taking high doses of ketoconazole for prostate cancer died soon after they began taking the medication. It is not known whether they died because of their disease or their treatment with ketoconazole or for other reasons.

Posaconazole (Noxafil®) comes as a suspension (liquid) to take by mouth. Each dose should be taken with a full meal or liquid nutritional supplement (which can be problematic as patient compliance with such instructions tends to be 60% or less). Posaconazole is also available in tablet form. An oral dose of 800 milligrams/day (in two or four divided doses) has been used for the treatment of various fungal infections. Oral and topical posaconazole has been used in the treatment of *Fusarium solani* keratitis and endophthalmitis at an initial oral dose of 200 milligrams four times daily in combination with hourly topical ocular application of posaconazole suspension (10 mg/0.1 milliliter) (Sponsel et al, 2002). When posaconazole is used to treat yeast infections of the mouth and throat, it is usually taken once or twice a day. Posaconazole is used to prevent serious fungal infections in people with a weakened ability to fight infection. Posaconazole is also used to treat yeast infections of the mouth and throat including yeast infections that could not be treated successfully with other medications. Posaconazole is in a class of antifungals called azoles and slows fungal growth by inhibiting ergosterol biosynthesis. Posaconazole may cause side effects, such as fever, headache, chills or shaking, dizziness, weakness, swelling of the hands, feet, ankles, or lower legs, diarrhea, vomiting, stomach pain, constipation, heartburn, weight loss, rash, itching, back or muscle pain, sores on the lips, mouth, or throat, difficulty falling asleep or staying asleep, anxiety, increased sweating, nosebleeds, coughing, unusual bruising or bleeding, extreme tiredness, lack of energy, loss of appetite, nausea, pain in the upper right part of the stomach, yellowing of the skin or eyes, flu-like symptoms, dark urine, pale stools, fast, pounding, or irregular heartbeat, sudden loss of consciousness, shortness of breath, and decreased urination.

Voriconazole (Vfend®) comes as a tablet and a suspension (liquid) to take by mouth. It is usually taken every 12 hours on an empty stomach, at least 1 hour before or 1 hour after a meal. Voriconazole is used to treat serious fungal infections such as invasive aspergillosis (a fungal infection that begins in the lungs and spreads through the bloodstream to other organs) and esophageal candidiasis (infection by a yeast-like fungus that may cause white patching in the mouth and throat). Voriconazole is in a class of antifungal medications called azoles and slows fungal growth by inhibiting ergosterol biosynthesis. Voriconazole may cause side effects, such as blurred or abnormal vision, difficulty seeing colors, sensitivity to bright light, diarrhea, vomiting, headache, dizziness, dry mouth, flushing, fever, chills or shaking, fast heartbeat, fast breathing, confusion, upset stomach, extreme tiredness, unusual bruising or bleeding, lack of energy, loss of appetite, pain in the upper right part of the stomach, yellowing of the skin or eyes, flu-like symptoms, hallucinations, chest pain, rash, hives, itching, difficulty breathing or swallowing, and swelling of the hands, feet, ankles, or lower legs.

Fluconazole comes as a tablet and a suspension (liquid) to take by mouth. It is usually taken once a day. Fluconazole is used to treat fungal infections, including yeast infections of the vagina, mouth, throat, esophagus, abdomen (area between the chest and waist), lungs, blood, and other organs. Fluconazole is in a class of antifungals called azoles and slows fungal growth by inhibiting ergosterol biosynthesis. Fluconazole may cause side effects, such as headache, dizziness, diarrhea, stomach pain, heartburn, change in ability to taste food, upset stomach, extreme tiredness, unusual bruising or bleeding, lack of energy, loss of appetite, pain in the upper right part of the stomach, yellowing of the skin or eyes, flu-like symptoms, dark urine, pale stools, seizures, rash, hives, itching, swelling of the face, throat, tongue, lips, eyes, hands, feet, ankles, or lower legs, and difficulty breathing or swallowing.

Topical antifungal drugs include ciclopirox, drugs containing miconazole (Daktarin, Micatin & Monistat), clotrimazole (Canesten, Hydrozole), butenafine (Lotrimin Ultra, Mentax), terbinafine (Lamisil), amorolfine (Curanail, Loceryl, Locetar, and Odenil), naftifine (Naftin) and tolnaftate (Tinactin). Others that may also be used to clear up fungal infections are ethylparaben, flucytosine, salicylic acid, selenium sulfide, and undecylenic acid. Several exemplary topical antifungal drugs are described below.

Ciclopirox olamine (also called Batrafen® Loprox®, Penlac® and Stieprox®) is a synthetic antifungal agent for topical dermatologic use that has a high affinity for trivalent metal cations. In a study conducted to further elucidate the mechanism of action of ciclopirox, several *Saccharomyces cerevisiae* mutants were screened and tested. Results from interpretation of the effects of both the drug treatment and mutation suggested that ciclopirox may exert its effect by several mechanisms, targeting multiple proteins that participate in various components of cellular metabolism, including DNA replication, DNA repair, and cellular transport (Leem et al., "The Possible Mechanism of Action of Ciclopirox Olamine in the Yeast *Saccharomyces cerevisiae*," *Mol. Cells.*, 15(1): 55-61 (2003)).

Ciclopirox comes as a solution to apply to nails and the skin immediately surrounding and under the nails. It is usually applied once a day. Ciclopirox is used to improve the condition of nails, but it may not completely cure nail fungus. Moreover, it may take 6 months or longer before there is any indication that the infected nails are improving. Ciclopirox should not be used with nail polish or other nail cosmetic products on nails treated with ciclopirox topical solution (which might be desirable by a patient). Moreover, ciclopirox topical solution may catch fire and therefore this medication should not be used near heat or an open flame, such as a cigarette. Side effects associated with ciclopirox include, but are not limited to, redness at the application site, irritation, itching, burning, blistering, swelling, or oozing at the application site, pain at the affected nail(s) or surrounding area, discoloration or change in shape of nail(s), and ingrown nail(s).

Ketoconazole cream (Nizoral®) is used to treat *tinea corporis* (ringworm; fungal skin infection that causes a red scaly rash on different parts of the body), *tinea cruris, tinea pedis, tinea versicolor* (fungal infection that causes brown or light colored spots on the chest, back, arms, legs, or neck), and yeast infections of the skin. Prescription ketoconazole shampoo is used to treat *tinea versicolor*. Ketoconazole is in a class of azole antifungal medications.

Ketoconazole may cause side effects, such as changes in hair texture, blisters on scalp, dry skin, itching, oily or dry hair or scalp, irritation, itching, or stinging at the application site, rash, hives, difficulty breathing or swallowing, and redness, tenderness, swelling, pain, or warmth at the application site.

C. Nanoemulsions

Prior teachings related to nanoemulsions are described in U.S. Pat. No. 6,015,832, which is directed to methods of inactivating a Gram-positive bacteria, a bacterial spore, or a Gram-negative bacteria. The methods comprise contacting the Gram-positive bacteria, bacterial spore, or Gram-negative bacteria with a bacteria-inactivating (or bacterial-spore inactivating) emulsion. U.S. Pat. No. 6,506,803 is directed to methods of killing or neutralizing microbial agents (e.g., bacteria, virus, spores, fungus, on or in humans using an emulsion. U.S. Pat. No. 6,559,189 is directed to methods for decontaminating a sample (human, animal, food, medical device, etc.) comprising contacting the sample with a nanoemulsion. The nanoemulsion, when contacted with bacterial, virus, fungi, protozoa, or spores, kills or disables the pathogens. The antimicrobial nanoemulsion generally comprises, in an aqueous medium, a quaternary ammonium compound, one of ethanol/glycerol/PEG, an oil, and a surfactant. U.S. Pat. No. 6,635,676 is directed to two different compositions and methods of decontaminating samples by treating a sample with either of the compositions. Composition 1 comprises an emulsion that is antimicrobial against bacteria, virus, fungi, protozoa, and/or spores. The emulsions comprise an oil and a quaternary ammonium compound. U.S. Pat. No. 7,314,624 is directed to methods of inducing an immune response to an immunogen comprising treating a subject via a mucosal surface with a combination of an immunogen and a nanoemulsion. The nanoemulsion comprises oil, ethanol, a surfactant, a quaternary ammonium compound, and distilled water. US-2005-0208083-A1 and US-2006-0251684-A1 are directed to nanoemulsions having droplets with preferred sizes. US-2007-0054834-A1 is directed to compositions comprising quaternary ammonium halides and methods of using the same to treat infectious conditions. The quaternary ammonium compound may be provided as part of an emulsion. Finally, US-2007-0036831-A1 is directed to nanoemulsions comprising an anti-inflammatory agent.

There is a need in the art for improved treatment options for patients affected by fungal infections, including fungal infections of the toenails, fingernails and the skin. Specifically, there is a need in the art for highly effective fungicidal agents that completely eradicate fungal infections of the toenails, fingernails and the skin. The present invention satisfies these needs.

SUMMARY OF THE INVENTION

The present invention provides methods and compositions for treating and/or preventing infection by a fungal, yeast, and/or mold agent in a human subject comprising administering topically or intradermally to the human subject a nanoemulsion, wherein the fungal or yeast agent is *Trichophyton* species, *Epidermophyton* species, *Candida* species, *Microsporum* species, *Aspergillus* species, *Paecilomyces* species, *Fusarium* species, *Acremonium* species, *Chaetomium* species, *Phoma* species, *Scopulariopsis* species, *Scytalidium* species, *Alternaria* species, *Epicoccum* species, *Curvularia* species, or any combination thereof. Methods and compositions for treating infection by any species of these genera is encompassed by the invention.

The nanoemulsion comprises droplets having an average diameter of less than about 1000 nm, and the nanoemulsion droplets comprise an aqueous phase, at least one oil, at least one surfactant, and at least one organic solvent.

The *Trichophyton* species can be, for example, *T. ajelloi, T. concentricum, T. equinum, T. erinacei, T. flavescens, T. gloriae, T. interdigitale, T. megnini, T. mentagrophytes, T. phaseoliforme, T. rubrum, T. schoenleini, T. simii, T. soudanense, T. terrestre, T. tonsurans, T. vanbreuseghemii, T. verrucosum, T. violaceum*, or *T. yaoundei*. The *Epidermophyton* species can be, for example, *E. floccosum* or *E. stockdaleae*. The *Candida* species can be, for example, *C. albicans, C. parapsiliosis, C. krusei, C. tropicalis, C. glabrata, C. parapsilosis, C. lusitaniae, C. kefyr, C. guilliermondii*, or *C. dubliniensis*. The *Microsporum* species can be, for example, *M. canis, M. gypseum, M. audouini, M. gallinae, M. ferrugineum, M. distortum, M. nanum, M. cookie*, or *M. vanbreuseghemii*. The *Epicoccum* species can be, for example, *E. nigrum*. The *Aspergillus* species can be, for example, *A. sydowii, A. terreus, A. niger, A. terreus, A. fumigatus, A. flavus, A. clavatus, A. glaucus* group, *A. nidulans, A. oryzae, A. terreus, A. ustus*, or *A. versicolor*. The *Paecilomyces* species can be, for example, *P. lilacinus* or *P. variotii*. The *Fusarium* species can be, for example, *F. oxysporum, F. solani*, or *F. semitectum*. The *Chaetomium* species can be, for example, *C. atrobrunneum, C. funicola, C. globosum*, or *C. strumarium*. The *Scopulariopsis* species can be, for example, *S. brevicaulis, S. candida, S. koningii, S. acremonium, S. flava, S. cinerea, S. trigonospora, S. brumptii, S. chartarum, S. fusca*, or *S. asperula*. The *Scytalidium* species can be, for example, *S. dimidiatum, S. hyalinum, S. infestans, S. japonicum*, or *S. lignicola*. The *Alternaria* species can be, for example, *A. alternate, A. chartarum, A. dianthicola, A. geophilia, A. infectoria, A. stemphyloides*, or *A. teunissima*. The *Curvularia* species can be, for example, *C. brachyspora, C. clavata, C. geniculata, C. lunata, C. pallescens, C. senegalensis*, or *C. verruculosa*.

Surprisingly, it was discovered that the topically applied nanoemulsions are as effective in treating, or better, than orally administered conventional antifungal treatments for infections caused by *Trichophyton* species, *Epidermophyton* species, *Candida* species, *Microsporum* species, *Aspergillus* species, *Paecilomyces* species, *Fusarium* species, *Acremonium* species, *Chaetomium* species, *Phoma* species, *Scopulariopsis* species, *Scytalidium* species, *Alternaria* species, *Epicoccum* species, and/or *Curvularia* species. This is significant, as a topically applied, and therefore local, site specific activity, is highly preferably over an orally administered, and therefore systemic activity. As noted in the background section, systemic antifungal drugs have many side effects, some very serious.

The patient to be treated may suffer from a fungal, yeast, and/or mold infection, such as a *tinea* infection, dermatophytoses, and/or dermatophytoma. In addition, the fungal or yeast infection may be *Tinea pedis, Tinea unguium, Tinea corporis, Tinea cruris, Tinea capitis, Tinea manuum, Tinea barbae, Tinea faciale, Tinea versicolor*, or fungal keratitis. In one aspect of the invention, the patient may be affected by onychomycosis.

The nanoemulsion comprises droplets having an average particle size of less than about 1000 nm, and the nanoemulsion comprises water, at least one oil, at least one surfactant, and at least one organic solvent. In one embodiment of the invention, the surfactant present in the nanoemulsion is a cationic surfactant. In another embodiment of the invention, the nanoemulsion further comprises a chelating agent. In one embodiment of the invention, nanoemulsions from the present invention, or those derived from the nanoemulsions of the present invention, are diluted. The diluted samples can then be tested to determine if they maintain the desired functionality, such as such as surfactant concentration, stability, particle size, and/or anti-infectious activity (e.g., antifungal activity).

In some embodiments, an additional active agent, such as an antifungal, antiyeast or antimold agent, is incorporated into the nanoemulsion to achieve improved absorption of the active agent. Preferably, the second active agent is an antifungal agent, such as terbinafine hydrochloride (TBHC) or miconazole. However, any suitable or desirable active agent useful in treating onychomycosis can be incorporated into the nanoemulsion to achieve anti-fungal activity in the skin and soft tissues.

Preferably, the nanoemulsions for topical or intradermal administration are in the form of any pharmaceutically acceptable dosage form, including but not limited to, ointments, creams, emulsions, lotions, gels, liquids, bioadhesive gels, sprays, shampoos, aerosols, pastes, foams, sunscreens, capsules, microcapsules, or in the form of an article or carrier, such as a bandage, insert, syringe-like applicator, pessary, powder, talc or other solid, shampoo, cleanser (leave on and wash off product), and agents that favor penetration within the epidermis, the dermis and keratin layers. The nanoemulsion is capable of effectively treating, preventing, and/or curing infection by *Trichophyton* species, *Epidermophyton* species, *Candida* species, *Microsporum* species, *Aspergillus* species, *Paecilomyces* species, *Fusarium* species, *Acremonium* species, *Chaetomium* species, *Phoma* species, *Scopulariopsis* species, *Scytalidium* species, *Alternaria* species, *Epicoccum* species, *Curvularia* species, or any combination thereof, without being systemically absorbed and without irritating the epithelium.

The nanoemulsion of the invention can be fungicidal or fungistatic (e.g., against every isolate of dermatophyte) and is effective against fungal conidia, hyphae, mycelia and spores.

In one embodiment of the invention, the nanoemulsions of the invention provide a mycological cure for the condition to be treated.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DESCRIPTION OF THE DRAWINGS

FIG. 1 shows nanoemulsion delivery into skin, including localization of nanoemulsion within hair follicles and sebaceous glands, with FIG. 1A showing a skin cross-section, with arrows identifying a sebaceous gland and hair follicles; FIG. 1B shows a skin cross section under fluorescence with fluorscein without nanoemulsion, and FIG. 1C shows a skin cross section under fluorescence with fluorscein plus nanoemulsion, with arrows identifying hair follicles and a sebaceous gland.

FIG. 2 shows nanoemulsion delivery into skin, including lateral diffusion of nanoemulsion from hair follicles and sebaceous glands into dermis and epidermis, with FIG. 2A showing a skin cross-section, with arrows identifying hair follicles; FIG. 2B shows a skin cross section under fluorescence with fluorscein without nanoemulsion, and FIG. 2C shows a skin cross section under fluorescence with fluorscein plus nanoemulsion, with arrows identifying hair follicles.

FIG. 3 graphically compares the fungicidal effect, expressed as minimum inhibitory concentration (MIC) and minimum fungicidal concentration (MFC) values, of the nanoemulsion of the invention to the effect of other fungistatic drugs currently used for the treatment of fungal infection, on fungi isolates of *Trichophyton rubrum*. (A) Nanoemulsion ("NB-002", comprising, in an aqueous medium, soybean oil, Tween 20® as a nonionic surfactant, ethanol, cetylpyridinium chloride (CPC) as a cationic surfactant, EDTA, and water); (B) Terbinafine; (T) Ciclopirox (C); (D) Itraconazole.

FIG. 4 illustrates the mechanism of action of the nanoemulsion of the invention as it relates to onychomycosis.

FIG. 5 graphically illustrates the progression in the linear growth of a new unaffected nail as assessed by trained investigators after treatment with (A) vehicle; (B) nanoemulsion comprising 0.25% cetylpyridinium chloride, given twice daily; (C) nanoemulsion comprising 0.5% cetylpyridinium chloride, given once daily; and (D) nanoemulsion comprising 0.5% cetylpyridinium chloride, given twice daily. The nanoemulsion treatment group shows clear progression in the growth of new, unaffected nail.

FIG. 6 graphically illustrates the progression in the linear growth of a new unaffected nail as assessed by planimetry after treatment with (A) vehicle; (B) nanoemulsion comprising 0.25% cetylpyridinium chloride, given twice daily; (C) nanoemulsion comprising 0.5% cetylpyridinium chloride, given once daily; and (D) nanoemulsion comprising 0.5% cetylpyridinium chloride given twice daily. The nanoemulsion treatment results in a clear progression in the growth of new, unaffected nail.

FIG. 7 graphically illustrates the progressive decrease in the area of affected nail by planimetric analysis after treatment with (A) vehicle; (B) nanoemulsion comprising 0.25% cetylpyridinium chloride, given twice daily; (C) nanoemulsion comprising 0.5% cetylpyridinium chloride, given once daily; and (D) nanoemulsion comprising 0.5% cetylpyridinium chloride, given twice daily. The nanoemulsion treatment produces a progressive decrease in the area of affected nail.

FIG. 8 compares the mycological cure rates obtained 8 weeks or more after stopping treatment with a nanoemulsion according to the invention as compared to treatment with Penlac®.

FIG. 9 shows a chart of antifungal activity of an exemplary nanoemulsion of the invention (NB-002) against rare onychomycosis fungal pathogens.

FIG. 10 shows the impact of a nanoemulsion according to the invention on the viability of *T. rubrum* over time (both hyphae and microconidial spores). The impact of nanoemulsions (4×MIC) and comparators (16×MIC) on the viability of *T. rubrum* NBD031 mycelia is shown on the left (10A) and on microconidia on the right (10B). The comparators tested were Itraconazole (diamond); terbinafine (square); ciclopirox (triangle); and the nanoemulsion (X). The lower limit of detection was 100 cfu.

FIG. 11 shows the fungicidal activity of an exemplary nanoemulsion of the invention (NB-002) against *Trichophyton rubrum, Trichophyton mentagrophytes*, and *Epidermophyton floccosum*, with FIG. 11A showing a scanning electron micrograph of *Trichophyton rubrum* NBDO30 mycelia (no treatment); FIG. 11B showing mycelia after 1 hour treatment at room temperature with 100 µg/ml of an exemplary nanoemulsion of the invention (NB-002) (50×MIC) (2,000× magnification); FIG. 11C a scanning electron micrograph of *Trichophyton rubrum* microconidia spores (arrows) without treatment; and FIG. 11D showing shows a scanning electron micrograph of *Trichophyton rubrum* microconidia spores (arrows) after treatment with an exemplary nanoemulsion of the invention (NB-002) (12.5 µg/ml≈6×MIC) for 1 hour at room temperature (5,000× magnification).

FIG. 12 shows a scanning electron micrograph of *Trichophyton rubrum* hyphae treated with an exemplary nanoemulsion of the invention (NB-002) (~50×MIC) for 1 hour at room temperature (11,000× magnification).

FIG. 13 shows nanoemulsion delivery into human cadaver skin at 24 hours. FIG. 13A shows a comparison of absorption into the epidermis for a nanoemulsion comprising 0.3% w/v cetylpyridinium chloride (CPC) and a control composition comprising 0.3% w/v aqueous cetylpyridinium chloride (CPC), following a single application onto human cadaver skin. FIG. 13B shows a comparison of absorption into the dermis for a nanoemulsion comprising 0.3% w/v cetylpyridinium chloride (CPC) and a control composition comprising 0.3% w/v aqueous cetylpyridinium chloride (CPC), following a single application onto human cadaver skin. In contrast to micellar CPC, the unique structure of the nanoemulsion droplet results in significant skin permeation.

FIG. 14 shows the effect of varying the concentration of a cationic surfactant present in a nanoemulsion according to the invention upon absorption into the epidermis and dermis of pig skin. FIG. 14A shows a comparison of absorption into the epidermis following a single application and three applications of nanoemulsions comprising 0.1%, 0.2%, 0.3%, 0.4%, or 0.5% w/v cetylpyridinium chloride (CPC). FIG. 14B shows a comparison of absorption into the dermis following a single application and three applications of nanoemulsions comprising 0.1%, 0.2%, 0.3%, 0.4%, or 0.5% w/v cetylpyridinium chloride (CPC).

FIG. 15 shows the absorption of a nanoemulsion comprising terbinafine hydrochloride (TBHC) into the epidermis of pig skin in comparison to the Lamisil® cream (Lamisil® is a non-nanoemulsion composition comprising TBHC), following two applications of the TBHC formulations, demonstrating significantly improved absorption of TBHC when the compound is incorporated into a nanoemulsion.

FIG. 16 shows the absorption of a nanoemulsion comprising terbinafine hydrochloride (TBHC) into the dermis of pig skin in comparison to the Lamisil® cream (Lamisil® is a non-nanoemulsion composition comprising TB), following two applications of the TB formulations, demonstrating significantly improved absorption of TBHC when the compound is incorporated into a nanoemulsion.

FIG. 17 shows levels of miconazole (MCZ) in swine skin epidermis at 24 hours after topical application (BID dosing) for MCZ incorporated into a nanoemulsion as compared to MCZ topically applied in a non-nanoemulsion formulation (Lotrimin® AF Spray Solution), demonstrating the significantly improved delivery of the MCZ into the epidermis when MCZ is incorporated into a nanoemulsion.

FIG. 18 shows levels of miconazole (MCZ) in swine skin dermis at 24 hours after topical application (BID dosing) for MCZ incorporated into a nanoemulsion as compared to MCZ topically applied in a non-nanoemulsion formulation (Lotrimin® AF Spray Solution), demonstrating the significantly improved delivery of the MCZ into the dermis when MCZ is incorporated into a nanoemulsion.

FIG. 19 illustrates the dimensions of a lateral diffusion study utilizing human cadaver skin described in Example 13, with two concentric glass rings defining an outer dosing area of 5.27 cm$^2$, a middle area of 3.3 cm$^2$, and an inner area of 0.5 cm$^2$.

FIG. 20 illustrates the design of a lateral diffusion study described in Example 13. With the design of the lateral diffusion study, the only route for CPC to be present inside the chamber is to permeate into the skin sample and move laterally through the tissue.

Figure 1C:
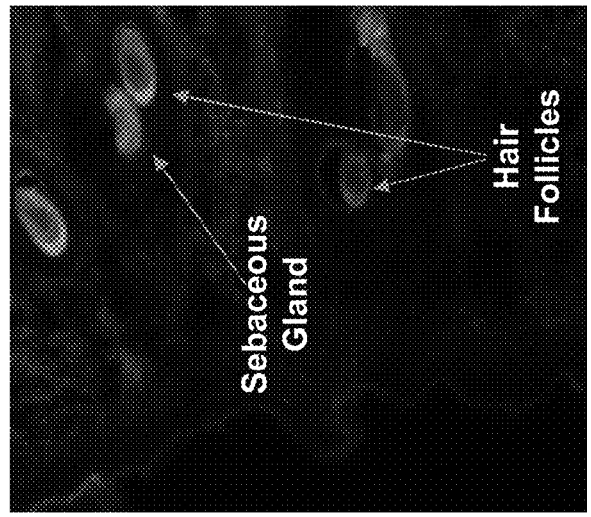

FIG. 21 graphically describes the results of a lateral diffusion study utilizing human cadaver skin and a nanoemulsion according to the invention comprising 0.5% w/v cetylpyridinium chloride (CPC) (FIG. 21B) as compared to a control composition comprising 0.5% w/v cetylpyridinium chloride (CPC) aqueous solution (FIG. 21A). The results of lateral diffusion over a 24 hour period are depicted, with minimal lateral diffusion into the middle region and no lateral diffusion shown in the inner region for the aqueous CPC solution composition. In contrast, lateral diffusion was clearly measured for the middle and inner regions when the 0.5% nanoemulsion was applied.

FIG. 22 graphically shows the results of the lateral diffusion study described in Example 13, wherein the transport of 0.5% nanoemulsion and 0.25% nanoemulsion within epidermal tissue is exhibited in all three regions: the outer dosing region and the middle and inner regions (measurement of CPC was used as a marker for delivery of the nanoemulsion). Twenty-four hours after an application of the nanoemulsion in the outer dosing region at time 0 and 8 hours, measurable amounts of nanoemulsion were detected in the outer, middle, and inner regions of the epidermis that exceeded the minimum fungicidal concentration (MFC$_{90}$) of 4 μg/g nanoemulsion.

FIG. 23 graphically shows the results of the lateral diffusion study described in Example 13, wherein the transport of 0.5% nanoemulsion and 0.25% nanoemulsion within dermal tissue is exhibited in all three regions: the outer dosing region and the middle and inner regions (measurement of CPC was used as a marker for delivery of the nanoemulsion). Twenty-four hours after an application of the nanoemulsion in the outer dosing region at time 0 and 8 hours, measurable amounts of nanoemulsion were detected in the outer, middle, and inner regions of the dermis that exceeded the minimum fungicidal concentration (MFC$_{90}$) of 4 μg/g nanoemulsion.

FIG. 24 graphically shows the lateral diffusion of the tested 0.5% nanoemulsion within the epidermis 24 hours after a single application in the outer dosing region, with measurable amounts of nanoemulsion detected in the outer, middle, and inner regions (measurement of CPC was used as a marker for delivery of the nanoemulsion).

FIG. 25 graphically shows the lateral diffusion of nanoemulsion within the dermis 24 hours after a single application in the outer dosing region, with measurable amounts of nanoemulsion detected in the outer, middle, and inner regions (measurement of CPC was used as a marker for delivery of the nanoemulsion).

DETAILED DESCRIPTION OF THE INVENTION

The present invention provides methods and compositions for treating, preventing, and/or curing infection by a fungal, yeast, and/or mold agent in a human subject comprising administering topically or intradermally to the human subject a nanoemulsion. The fungal, yeast, and/or mold agent can be any known fungal, yeast, and/or mold agent, including any such agents described herein. In exemplary methods and compositions, the agent is a *Trichophyton* species, *Epidermophyton* species, *Candida* species, *Microsporum* species, *Aspergillus* species, *Paecilomyces* species, *Fusarium* species, *Acremonium* species, *Chaetomium* species, *Phoma* species, *Scopulariopsis* species, *Scytalidium* species, *Alternaria* species, *Epicoccum* species, *Curvularia* species, or any combination thereof. The invention encompasses methods and compositions of treating infection caused by any species of these genera.

Examples of *Trichophyton* species include *T. ajelloi*, *T. concentricum*, *T. equinum*, *T. erinacei*, *T. flavescens*, *T. gloriae*, *T. interdigitale*, *T. megnini*, *T. mentagrophytes*, *T. phaseoliforme*, *T. rubrum*, *T. schoenleini*, *T. simii*, *T. soudanense*, *T. terrestre*, *T. tonsurans*, *T. vanbreuseghemii*, *T. verrucosum*, *T. violaceum*, and *T. yaoundei*.

Examples of *Epidermophyton* species include *E. floccosum* (obsolete synonyms of the obsolete species include *E. clypeiforme*, *E. clypeiforme*, *E. inguinale*, *E. plicarum*, *Acrothecium floccosum*, *Trichophyton cruris*, *Trichophyton floccosum*, *Trichophyton inguinale*, *Trichophyton intertriginis*, and *Trichothecium floccosum*) and *E. stockdaleae*.

Examples of *Candida* species include *C. albicans*, *C. parapsiliosis*, and *C. krusei*. *Candida* is a yeast and the most common cause of opportunistic mycoses worldwide. It is also a frequent colonizer of human skin and mucous membranes. The genus *Candida* includes around 154 species. Among these, six are most frequently isolated in human infections. While *C. albicans* is the most abundant and significant species, *C. tropicalis*, *C. glabrata*, *C. parapsilosis*, *C. krusei*, and *C. lusitaniae* are also isolated as causative agents of *Candida* infections. Other *Candida* species include *C. kefyr*, *C. guilliermondii*, and *C. dubliniensis*. Importantly, there has been a recent increase in infections due to non-albicans *Candida* spp., such as *C. glabrata* and *C. krusei* (Abi-Said et al., "The epidemiology of hematogenous candidiasis caused by different *Candida* species," *Clin. Infect. Dis.*, 24:1122-1128 (1977); Aisner et al, "*Torulopsis glabrata* infections in patients with cancer: Increasing incidence and relationship to colonization," *Am. J. Med.*, 61:23-28 (1976); Arif et al., "Techniques for investigation of an apparent outbreak of infections with *Candida glabrata*," *J Clin Microbiol.*, 34:2205-9 (1996)). Patients receiving fluconazole prophylaxis are particularly at risk of developing infections due to fluconazole-resistant *Candida krusei* and *Candida glabrata* strains. (Barchiesi et al., "Emergence of oropharyngeal candidiasis caused by non-albicans species of *Candida* in HIV-infected patients (letter)," *Eur. J. Epidemiol.*, 9:455-456 (1993). Nevertheless, the diversity of *Candida* spp. that are encountered in infections is expanding and the emergence of other species that were rarely in play in the past is now likely. Infections caused by *Candida* spp. are in general referred to as candidiasis. The clinical spectrum of candidiasis is extremely diverse. Almost any organ or system in the body can be affected. Candidiasis may be superficial and local or deep-seated and disseminated. Disseminated infections arise from hematogenous spread from the primarily infected locus. *Candida albicans* is the most pathogenic and most commonly encountered species among all. Its ability to adhere to host tissues, produce secretory aspartyl proteases and phospholipase enzymes, and transform from yeast to hyphal phase are the major determinants of its pathogenicity.

The genus *Microsporum* includes 17 conventional species. Among these, the most significant are: *M. audouini*, *M. galli-* nae, *M. ferrugineum, M. distortum, M. nanum, M. canis, M. gypseum, M. cookie,* and *M. vanbreuseghemii. Microsporum* is one of the three genera that cause dermatophytosis. Dermatophytosis is a general term used to define the infection in hair, skin or nails due to any dermatophyte species. Similar to other dermatophytes, *Microsporum* has the ability to degrade keratin and thus can reside on skin and its appandages and remains noninvasive. As well as the keratinase enzyme, proteinases and elastases of the fungus may act as virulence factors. Notably, *Microsporum* spp. mostly infect the hair and skin, except for *Microsporum persicolor* which does not infect hair. Nail infections are not as common. The pathogenesis of the infection depends on the natural reservoir of the species. *Geophilic* spp. are acquired via contact with soil. *Zoophilic* species are transmitted from the infected animal. Direct or indirect (via fomites) human-to-human transmission is of concern for anthropophilic species. Asymptomatic carriage may be observed. As well as the otherwise healthy hosts, immunocompromised patients are also infected.

The genus *Aspergillus* includes over 185 species. Around 20 species have so far been reported as causative agents of opportunistic infections in man. Among these, *A. fumigatus* is the most commonly isolated species, followed by *A. flavus* and *A. niger. A. clavatus, A. glaucus* group, *A. nidulans, A. oryzae, A. terreus, A. ustus,* and *A. versicolor* are among the other species less commonly isolated as opportunistic pathogens. Among all filamentous fungi, *Aspergillus* is in general the most commonly isolated one in invasive infections. It is the second most commonly recovered fungus in opportunistic mycoses following *Candida*. Almost any organ or system in the human body may be involved. Onychomycosis, sinusitis, cerebral aspergillosis, meningitis, endocarditis, myocarditis, pulmonary aspergillosis, osteomyelitis, otomycosis, endophthalmitis, cutaneous aspergillosis, hepatosplenic aspergillosis, as well as *Aspergillus fungemia,* and disseminated aspergillosis may develop. (Arikan et al., "Primary cutaneous aspergillosis in human immunodeficiency virus-infected patients: Two cases and review," *Clin. Infect. Dis.,* 27:641-643 (1998); Denning, D. W., "Invasive aspergillosis," *Clin. Infect. Dis.,* 26:781-803 (1998); Gefter, W. B., "The spectrum of pulmonary aspergillosis," *Journal of Thoracic Imaging,* 7:56-74 (1992); Gumbo et al., "*Aspergillus* valve endocarditis in patients without prior cardiac surgery," *Medicine,* 79:261-268 (2000); Gupta et al., "Combined distal and lateral subungual and white superficial onychomycosis in the toenails," *J. Am. Acad. Dermatol.,* 41:938-44 (1999); Katz et al., "Ocular aspergillosis isolated in the anterior chamber," *Opthalmology,* 100:1815-1818 (1993).) Nosocomial occurrence of aspergillosis due to catheters and other devices is also likely. Construction in hospital environments constitutes a major risk for development of aspergillosis particularly in neutropenic patients. *Aspergillus* spp. may also be local colonizers in previously developed lung cavities due to tuberculosis, sarcoidosis, bronchiectasis, pneumoconiosis, ankylosing spondylitis or neoplasms, presenting as a distinct clinical entity, called aspergilloma. Aspergilloma may also occur in kidneys.

The genus *Paecilomyces* contains several species. The most common are *P. lilacinus* and *P. variotii. Paecilomyces* species can cause various infections in humans. These infections are occasionally referred to as paecilomycosis. Corneal ulcer, keratitis, and endophthalmitis due to Paecilomyces may develop following extended wear contact lens use or ocular surgery. (Pettit et al., "Fungal endophthalmitis following intraocular lens implantation. A surgical epidemic," *Arch. Opthalmol.,* 98:1025-1039 (1980).) *Paecilomyces* is among the emerging causative agents of opportunistic mycoses in immunocompromised hosts. (Groll et al., "Uncommon opportunistic fungi: new nosocomial threats," *Clin. Microbiol. Infect.,* 7:8-24 (2001).) Direct cutaneous inoculation may lead to these infections. (Orth et al., "Outbreak of invasive mycoses caused by *Paecilomyces lilacinus* from a contaminated skin lotion," *Ann. Intern. Med.,* 125:799-806 (1996).) These infections may involve almost any organ or system of human body. Soft tissue (Williamson et al., "Successful treatment of *Paecilomyces varioti* infection in a patient with chronic granulomatous disease and a review of *Paecilomyces* species infections," *Clin. Infect. Dis.,* 14:1023-1026 (1992)), pulmonary (Byrd et al., "*Paecilomyces variotii* penumonia in a patient with diabetes mellitus," *J Diabetes Complic.,* 6:150-153 (1992)), and cutaneous infections (Orth et al.; Safdar, A., "Progressive cutaneous hyalohyphomycosis due to *Paecilomyces lilacinus*: Rapid response to treatment with caspofungin and Itraconazole," *Clin. Infect. Dis.,* 34:1415-1417 (2002)), cellulitis (Jade et al., "*Paecilomyces lilacinus* cellulitis in an immunocompromised patient," *Arch. Dermatol.,* 122:1169-70 (1986)), onychomycosis (Fletcher et al., "Onychomycosis caused by infection with *Paecilomyces lilanicus,*" *Br. J. Dermatol.,* 139:1133-1135 (1998)), sinusitis (Gucalp et al., "*Paecilomyces sinusitis* in an immunocompromised adult patient: Case report and review," *Clin. Infect. Dis.,* 23:391-393 (1996); Rockhill et al., "*Paecilomyces lilacinus* as the cause of chronic maxillary sinusitis," *J. Clin. Microbiol.,* 11:737-739 (1980)), otitis media (Dhindsa et al., "Chronic supparative otitis media caused by *Paecilomyces variotii,*" *J. Med. Vet. Mycol.,* 33:59-61 (1995)), endocarditis (Haldane et al., "Prosthetic valvular endocarditis due to the fungus Paecilomyces," *Can. Med. Assoc. J.,* 111:963-5, 968 (1974)), osteomyelitis (Cohen-Abbo et al., "Multifocal osteomyelitis caused by *Paecilomyces varioti* in a patient with chronic granulomatous disease," *Infection,* 23:55-7 (1995)), peritonitis (Rinaldi et al., "*Paecilomyces variotii* peritonitis in an infant on automated peritoneal dialysis," *Pediat. Nephrol.,* 14:365-366 (2000)), and catheter-related fungemia (Tan et al., "*Paecilomyces lilacinus* catheter-related fungemia in an immunocompromised pediatric patient," *J. Clin. Microbiol.,* 30:2479-2483 (1992)) have all been reported.

As well as being common plant pathogens, *Fusarium* spp. are causative agents of superficial and systemic infections in humans. Infections due to *Fusarium* spp. are collectively referred to as fusariosis. The most virulent *Fusarium* spp. is *Fusarium solani*(Mayayo et al., "Experimental pathogenicity of four opportunist *Fusarium* species in a murine model," *J. Med. Microbiol.,* 48:363-366 (1999).). Trauma is the major predisposing factor for development of cutaneous infections due to *Fusarium* strains. Disseminated opportunistic infections, on the other hand, develop in immunosuppressed hosts, particularly in neutropenic and transplant patients (Vartivarian et al., "Emerging fungal pathogens in immunocompromised patients: classification, diagnosis, and management," *Clin. Infect. Dis.* 17:S487-91 (1993); Venditti et al., "Invasive *Fusarium solani* infections in patients with acute leukemia," *Rev. Infect. Dis.,* 10:653-660 (1988)). *Fusarium* infections following solid organ transplantation tend to remain local and have a better outcome compared to those that develop in patients with hematological malignancies and bone marrow transplantation patients (Sampathkumar et al., "*Fusarium* infection after solid-organ transplantation," *Clin. Infect. Dis.,* 32:1237-1240 (2001)), Keratitis (Tanure et al., "Spectrum of fungal keratitis at Wills Eye Hospital, Philadelphia, Pa.," *Cornea,* 19:307-12 (2000)), endophthalmitis (Louie et al., "Endogenous endophthalmitis due to *Fusarium*: case report and review," *Clin. Infect. Dis.,* 18:585-8 (1994)), otitis media (Wadhwani et al., "Fungi from otitis media of agricultural field workers," *Mycopathologia*, 88:155-9 (1984)), onychomycosis (Romano et al., "Skin and nail infections due to *Fusarium oxysporum* in Tuscany, Italy," *Mycoses*, 41:433-437 (1998)), cutaneous infections (Romano et al.), particularly of burn wounds, mycetoma, sinusitis, pulmonary infections (Rolston, K. V. I., "The spectrum of pulmonary infections in cancer patients," *Curr. Opin. Oncol.*, 13:218-223 (2001)), endocarditis, peritonitis, central venous catheter infections, septic arthritis, disseminated infections, and fungemia (Yildiran et al., "*Fusarium fungaemia* in severely neutropenic patients," *Mycoses*, 41:467-469 (1998)) due to *Fusarium* spp. have been reported.

*Acremonium* is one of the causative agents of eumycotic white grain mycetoma. Rare cases of onychomycosis, keratitis, endophthalmitis, endocarditis, meningitis, peritonitis, and osteomyelitis due to *Acremonium* have also been reported. This fungus is known to cause opportunistic infections in immunocompromised patients, such as bone marrow transplant recipients. Infections of artificial implants due to *Acremonium* spp. are occasionally observed.

The genus *Chaetomium* contains several species. The most common ones are *C. atrobrunneum, C. funicola, C. globosum,* and *C. strumarium. Chaetomium* spp. are among the fungi causing infections wholly referred to as phaeohyphomycosis. Fatal deep mycoses due to *Chaetomium atrobrunneum* have been reported in an immunocompromised host. Brain abscess, peritonitis, cutaneous lesions, and onychomycosis may also develop due to *Chaetomium* spp.

The genus *Phoma* contains several species. Most of the strains isolated from human infections have not been identified to species level. *Phoma* species are among the rarely encountered causes of phaeohyphomycosis. The infection commonly develops after a trauma and immunosuppression is a major risk factor for its development. These infections may be cutaneous, subcutaneous, corneal, or (rarely) systemic.

The most common *Scopulariopsis* species is *S. brevicaulis*. Other non-pigmented species include *S. candida, S. koningii, S. acremonium,* and *S. flava*. Dematiaceous or phaeoid members include *S. cinerea, S. trigonospora, S. brumptii, S. chartarum, S. fusca,* and *S. asperula. Scopulariopsis* spp. may cause various infections in humans. It is among the fungi that cause onychomycosis especially of the toe nails. Skin lesions, mycetoma, invasive sinusitis, keratitis, endophthalmitis, pulmonary infections, endocarditis, brain abscess and disseminated infections due to *Scopulariopsis* spp. have been reported. Invasive *Scopulariopsis* infections are seen mainly in immunocompromised hosts, such as bone marrow transplant recipients. These infections are highly mortal.

*Scytalidium* species include *S. dimidiatum, S. hyalinum, S. infestans, S. japonicum,* and *S. lignicola. Scytalidium* species is an occasional agent of nail or skin infections. Some cases of subcutaneous or disseminated infection have also been noted.

The genus *Alternaria* currently contains around 50 species. Among these, *A. alternata* is the most common one isolated from human infections. While *A. chartarum, A. dianthicola, A. geophilia, A. infectoria, A. stemphyloides,* and *A. teunissima* are among the other *Alternaria* spp. isolated from infections, some *Alternaria* strains reported as causative agents remain unspecified. *Alternaria* spp. have emerged as opportunistic pathogens particularly in patients with immunosuppression, such as the bone marrow transplant patients. They are one of the causative agents of phaeohyphomycosis. Cases of onychomycosis, sinusitis, ulcerated cutaneous infections, and keratitis, as well as visceral infections and osteomyelitis due to *Alternaria* have been reported. In immunocompetent patients, *Alternaria* colonizes the paranasal sinuses, leading to chronic hypertrophic sinusitis. In immunocompromised patients the colonization may end up with development of invasive disease. It is among the causative agents of otitis media in agricultural field workers.

The genus *Curvularia* contains several species, including *C. brachyspora, C. clavata, C. geniculata, C. lunata, C. pallescens, C. senegalensis,* and *C. verruculosa. C. lunata* is the most prevalent cause of disease in humans and animals. *Curvularia* spp. are among the causative agents of phaeohyphomycosis. Wound infections, mycetoma, onychomycosis, keratitis, allergic sinusitis, cerebral abscess, cerebritis, pneumonia, allergic bronchopulmonary disease, endocarditis, dialysis-associated peritonitis, and disseminated infections may develop due to *Curvularia* spp. *Curvularia lunata* is the most commonly encountered species. Importantly, the infections may develop in patients with intact immune system. However, similar to several other fungal genera, *Curvularia* has recently emerged also as an opportunistic pathogen that infects immunocompromised hosts.

The fungal infections caused by these agents are extensive, and currently available treatments have significant limitations and/or limited success. For example, *Trichophyton rubrum* is a fungus that is the most common cause of *Tinea pedis* (athlete's foot), *Tinea cruris* (jock itch) and dermatophytosis (ringworm). Other common skin diseases caused by *T. rubrum* include, but are not limited to, *Tinea capitis* (fungal folliculitis of the scalp), *Tinea barbae* (fungal folliculitis of the beard), *Majocchi granuloma* (fungal folliculistis of the legs), and onychomycosis. Although *T. rubrum* is the most common of the dermatophyes causing fingernail fungus infections, there are others. *Trichophytum mentagrophytes* is the second most common source of fungal nail infections from the dermatophyte group.

*Tinea corporis* is a common infection more often seen in typically hot, humid climates. *T. rubrum* is the most common infectious agent in the world and is the source of 47% of *tinea corporis* cases. *Trichophyton tonsurans* is an anthropophilic fungus with a world wide distribution which causes inflammatory or chronic non-inflammatory finely scaling lesions of skin, nails and scalp. *T. tonsurans* is the most common dermatophyte to cause *tinea capitis*, and people with an anthropophilic *tinea capitis* infection are more likely to develop associated *tinea corporis*. Therefore, the prevalence of *tinea corporis* caused by T tonsurans is increasing. *Microsporum canis* is the third most common causative organism and associated with 14% of *tinea corporis* infections. See http://emedicine.medscape.com/article/1091473-overview.

There have been recent reports of fungal infections caused by nondermatophyte molds increasing in both non-immunocompromised and immunocompromised patients (Malani et al., "Changing epidemiology of rare mould infections: implications for therapy," *Drugs*, 67:1803-1812 (2007); Tosti et al., *J. Am. Acad. Dermatol.*, 42:217-224 (2000)). Such organisms include but are not limited to *Aspergillus* spp., *Fusarium spp, Scedosporium* spp., *Paecilomyces* spp., *Scopulariopsis* spp., *Scytalidium* spp., *Chaetomium* spp., *Alternaria* spp., *Acremonium* spp. and *Curvularia* spp.

The nanoemulsion comprises droplets having an average diameter of less than about 1000 nm, and the nanoemulsion droplets comprise an aqueous phase, at least one oil, at least one surfactant, and at least one organic solvent. The "topical" application can be to any superficial skin structure, hair, hair shaft, hair follicle, eye, or any combination thereof.

In some embodiments, the nanoemulsion that diffuses around the nail, under the nail, across the nail, or through an imperfection in the nail, comprises an additional active agent. Preferably, the second active agent is an anti-fungal agent.

The patient to be treated may suffer from a fungal, yeast, and/or mold infection, such as a *tinea* infection, dermatophytoses, and dermatophytoma. In addition, the fungal, yeast, and/or mold infection may be *Tinea pedis, Tinea unguium, Tinea corporis, Tinea cruris, Tinea capitis, Tinea manuum, Tinea barbae, Tinea faciale, Tinea versicolor*, or fungal keratitis. In one aspect of the invention, the patient may be affected by onychomycosis.

In one embodiment of the invention, the fungal infection to be treated, prevented, or cured is onychomycosis. In this aspect of the invention, the topical application is to an infected nail, the skin surrounding an infected nail, or a combination thereof, and following application the nanoemulsion diffuses around the nail, under the nail, across the nail, through an imperfection in the nail, or a combination thereof.

One of the problems with conventional drugs used for treating fungal/yeast/mold infections of the skin and/or nails, is that fungal nail infections are generally located deep under the nail plate and even into the nail matrix, and topically applied conventional treatments have extreme difficulty in penetrating—or are unable to penetrate—the nail in sufficient amounts to produce a therapeutically effective treatment. Orally administered drugs may address this problem present in topically applied therapies, but orally administered drugs act systemically and, therefore, may cause undesired toxicity, e.g., hepatotoxicity. Patients are warned of this and may be monitored with liver function tests. Systemic drugs may be limited in spectrum and do not cover all fungi, yeast, and molds that cause onychomycosis.

Surprisingly, it was discovered that the topically applied nanoemulsions are as effective in treating, or better, than orally administered conventional antifungal treatments for infections caused by *Trichophyton* species, *Epidermophyton* species, *Candida* species, *Microsporum* species, *Aspergillus* species, *Paecilomyces* species, *Fusarium* species, *Acremonium* species, *Chaetomium* species, *Phoma* species, *Scopulariopsis* species, *Scytalidium* species, *Alternaria* species, *Epicoccum* species, *Curvularia* species, or any combination thereof. This is significant, as a topically applied, and therefore local, site-specific activity, is highly preferred over an orally administered drug, and therefore systemic activity. As noted in the background section, systemic antifungal drugs have many side effects, some very serious.

Moreover, the nanoemulsions can be applied to and around a barrier covering an infection, such as a nail, and following application the nanoemulsion then migrates under (or laterally diffuses under) the barrier to effectively reach and eradicate the infection. This result is obtained without systemic absorption, as a measurable quantity of the nanoemulsion is not found within the plasma of a treated subject (determined by measuring if any surfactant or detergent, such as a cationic surfactant present in the nanoemulsion, is absorbed into the bloodstream).

The nanoemulsions of the invention comprise surfactants approved for human consumption and common food substances that are 'Generally Recognized as Safe' (GRAS) by the FDA. The components used in the preparation of the nanoemulsions are all listed on the FDA's list of inactive ingredients in approved drug products.

A graphical mechanism of action of the nanoemulsions of the invention is depicted in FIG. 4. The nanoemulsion droplets, having an average diameter of less than about 1000 nm, can be applied to the skin and tissue surrounding an infected nail. A toenail is depicted in FIG. 4. The nanoemulsion droplets migrate through the skin pores/superficial skin structures, proximal and lateral folds, and under the nail, to reach the site of fungal, yeast or mold infection. While the inventors are not wished to be bound by theory, it is thought that the nanoemulsion droplets lyse fungal hyphae, cells and spores, thereby "killing" the fungus, mold, or yeast.

Specifically, FIG. 3 graphically compares the fungicidal effect, expressed as minimum inhibitory concentration (MIC) and minimum fungicidal concentration (MFC) values, of a nanoemulsion of the invention to the effect of other fungistatic drugs currently used for the treatment of fungal infection, on fungi isolates of *Trichophyton rubrum*. (A) Nanoemulsion ("NB-002"); (B) terbinafine; (C) ciclopirox; and (D) itraconazole. When used to treat fungal infections, ciclopirox is topically applied, while terbinafine and itraconazole are orally administered drugs. Surprisingly, the comparison shows that the nanoemulsions of the invention are fungicidal against *Trichophyton rubrum*, while ciclopirox, terbinafine, and itraconazole are merely fungistatic against *Trichophyton rubrum*. This is true even though the nanoemulsion is topically applied, as compared to the oral and systemic action of terbinafine and itraconazole. For the nanoemulsion, the MIC and MFC (sometimes also referred to as "MLC") values are basically equivalent, which means that the mechanism of action is fungicidal (MFC:MIC ratio is less than or equal to four-fold). However, for drugs such as terbinafine, the MIC and MLC values can differ by greater than four fold, meaning that the drug is not always fungicidal. A fungicidal treatment is much more desirable than a fungistatic treatment, as a fungicidal may be much more effective in completely "curing" the infection, as well as preventing infection reoccurrence.

Figure 12:
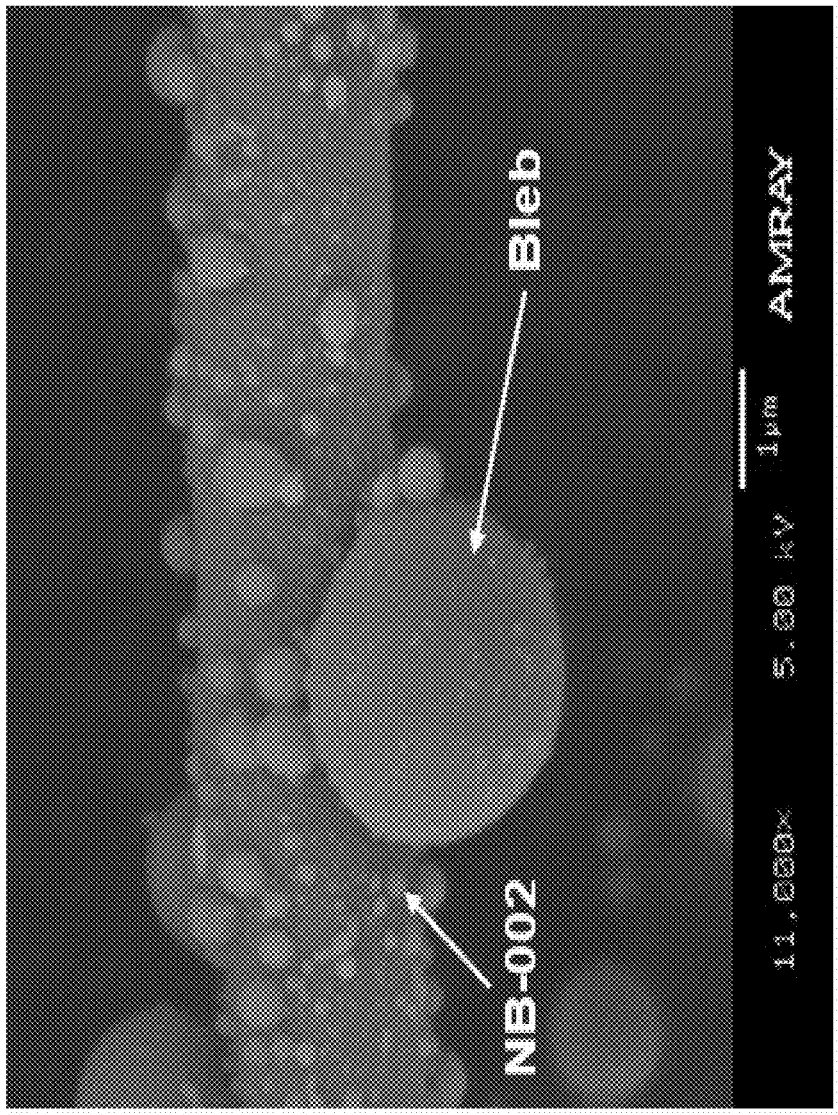

For example, FIG. 11 shows the effect of an exemplary nanoemulsion (NB-002, comprising, an aqueous medium, soybean oil, Tween 20® as a nonionic surfactant, ethanol, cetylpyridinium chloride (CPC) as a cationic surfactant, EDTA, and water) against growing hyphae and spores. FIG. 11A shows hyphae before application of the nanoemulsion, and FIGS. 11B and 12 show hyphae after application of the nanoemulsion. After application of the nanoemulsion, nanoemulsion droplets interact with the hyphae cell surface, causing formation of blebs (protrusions). Similarly, FIG. 11C shows spores before application of the nanoemulsion, and FIG. 11D shows spores after application of the nanoemulsion. FIG. 11D clearly shows that application of a nanoemulsion according to the invention results in lysis and destruction of the spores. Time-kill experiments verify that hyphae or spores treated with nanoemulsion are not viable (FIG. 10).

The nanoemulsions comprise droplets having an average diameter of less than about 1000 nm, and the nanoemulsions comprise an aqueous phase, at least one oil, at least one surfactant or detergent, and at least one organic solvent. In one embodiment of the invention, the surfactant present in the nanoemulsion is a cationic surfactant. More than one surfactant or detergent can be presenting the nanoemulsions of the invention. For example, the nanoemulsions can comprise a cationic surfactant in combination with a non-ionic surfactant. In another embodiment of the invention, the nanoemulsion further comprises a chelating agent. The "topical" application can be to any superficial skin structure, hair, hair shaft, hair follicle, eye, or any combination thereof. The organic solvent and the aqueous phase of the invention can be a non-phosphate based solvent. In some embodiments of the invention, a surfactant, such as a cationic surfactant, is used as a "marker" to measure absorption of the nanoemulsion into the epidermis and dermis (see e.g., FIGS. 13 and 14).

In some embodiments, an active agent, other than the nanoemulsion, such as an antifungal, antiyeast or antimold agent, is also incorporated into the nanoemulsion to achieve improved absorption of the active agent, thereby enhancing the killing effect of the active agent in tissues (FIGS. 15-18).

Figure 1B:
Figure 1A:
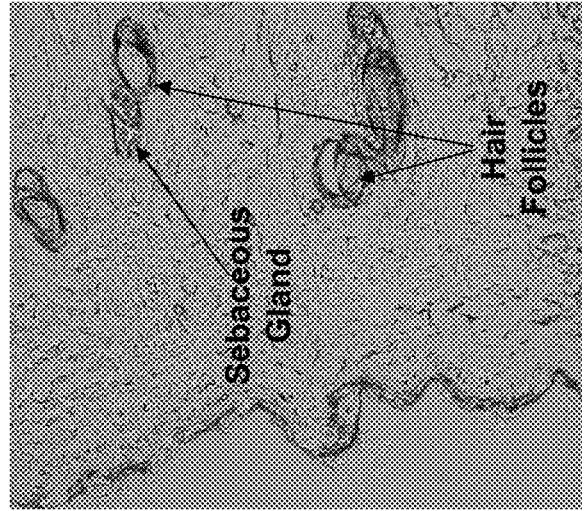
Figure 2C:
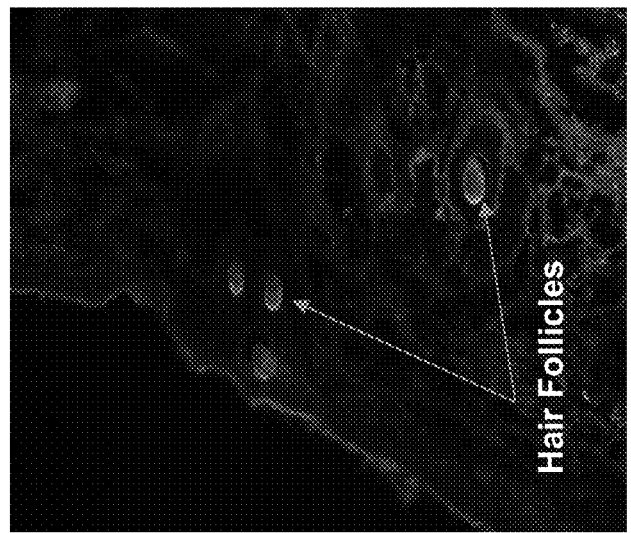
Figure 2B:
Figure 2A:
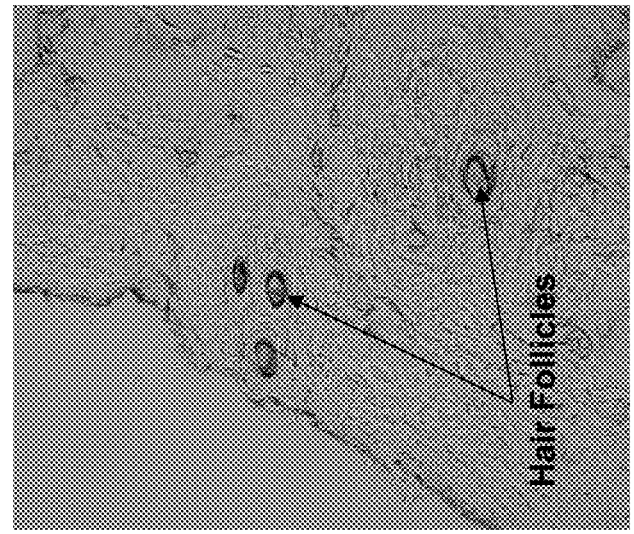

The nanoemulsions comprise high energy nanometer-sized droplets that permeate skin pores and hair follicles to enter the epidermis and dermis where they kill fungi (or virus, bacteria, mold, etc.) on contact. See FIGS. 1-2 and 13. Droplets having a suitable size can permeate skin pores and hair follicles, but can be excluded by tight junctions between epithelial cells and thus do not disrupt tissue matrices or enter blood vessels. This minimizes skin irritation and systemic absorption, but yet provides for a composition which is highly bioavailable in the epidermal and dermal tissues without causing disruption to the normal epithelial matrix. For example, the data described herein confirms that nanoemulsions described herein diffuse through the stratum corneum via the follicular route to accumulate in the epidermal and dermal tissues, without disrupting the normal epithelial matrix. The concentrations of nanoemulsion achieved in the epidermis and dermis were well above the concentrations required for anti-infective activity.

It is theorized that the nanoemulsion droplets kill fungi, virus, mold, yeast etc. via membrane destabilization, where the nanoemulsion droplets interact with outer cell surface, causing lysis. For example, nanoemulsion droplets have been shown to adhere to mycelia of fungus such as *Trichophyton rubrum*, appearing to fuse with the cell surface, forming blebs, resulting in death (FIGS. 10-12). Nanoemulsions as described herein were found to have a dramatic effect on the morphology and viability of hyphae, even after a minimal amount of exposure time. In addition, because the nanoemulsions of the invention were tested under nongrowth conditions (hyphae and microconidia were suspended in water), they do not require replication to be effective. Because nanoemulsions are theorized to have a mechanism of action of "kill on contact" via destabilization of the fungal cell surface, they are unlikely to develop resistance; experiments to show that spontaneous resistance either does not develop or is unstable are exemplified (Example 7).

Furthermore, it has been shown that the nanoemulsions of the invention diffuse laterally (FIGS. 21-25) within tissue planes to the site of infection without skin damage. Specifically, the examples below describe lateral diffusion of a nanoemulsion according to the invention along tissue planes to reach sites of infection up to ~1 cm away from the site of skin application. This enables the treatment of infections present under barriers, such as a human finger or toe nail. This is particularly attractive for treatment of onychomycosis, where dermatophytes infect under the nail plate. Thus the nanoemulsions are not dependent upon permeation across the nail plate to be effective.

Moreover, the examples show that the nanoemulsion comprising an additional active agent diffuses laterally to areas not directly underlying the site of application (Examples 12-14). The suitable active agent includes, but not limited to, any anti-fungal agent, including but not limited to any suitable class of antifungal agent, including but not limited to: (1) a polyene antifungal agent, such as Natamycin, Rimocidin, Filipin, Nystatin, Amphotericin B, and Candicin; (2) Imidazole antifungals, such as Miconazole, Ketoconazole, Clotrimazole, Econazole, Bifonazole, Butoconazole, Fenticonazole, Isoconazole, Oxiconazole, Sertaconazole, Sulconazole, Tioconazole; (3) Triazole antifungals, such as Fluconazole, Itraconazole, Isavuconazole, Ravuconazole, Posaconazole, Voriconazole, Terconazole; (4) Allylamine antifungals, such as Terbinafine, Amorolfine, Naftifine, and Butenafine; (5) Echinocandin antifungals, such as Anidulafungin, Caspofungin, and Micafungin; (6) other antifungals, such as Benzoic acid (has antifungal properties but must be combined with a keratolytic agent such as in Whitfield's Ointment, Ciclopirox, Tolnaftate, Undecylenic acid, Flucytosine (or 5-fluorocytosine), Griseofulvin, and Haloprogin; and (7) alternative agents, such as Allicin (created from crushing garlic), Tea tree oil (ISO 4730, "Oil of Melaleuca, Terpinen-4-ol type"), Citronella oil, Iodine (Lugols Solution), lemon grass, olive leaf, orange oil, palmarosa oil, patchouli, lemon myrtle, Neem Seed Oil, Coconut Oil, Zinc (zinc dietary supplements or natural food sources, including pumpkin seeds and chick peas), and Selenium (selenium dietary supplements or natural food sources, particularly Brazil nuts). This enables the treatment of infections present under barriers, such as a human finger or toe nail. This is particularly attractive for treatment of onychomycosis, where dermatophytes infect under the nail plate. Thus the nanoemulsions are not necessarily dependent upon permeation across the nail plate to be effective.

In another embodiment of the invention, fungal, yeast, and/or mold pathogens do not exhibit resistance development to a nanoemulsion according to the invention (Example 7). Specifically, as described in the examples below, while phenotypic resistance to a nanoemulsion according to the invention was observed, none of the tested isolates was stably resistant to the nanoemulsion. This is consistent with the uniform fungicidal activity of the nanoemulsions of the invention, described herein and within the examples.

Yet another benefit of the present invention is that the nanoemulsions described herein provide broad coverage against all primary pathogens causing onychomycosis, including but not limited to *Trichophyton rubrum*, *Trichophyton mentagrophytes*, and *Epidermophyton* floccosum. See Example 1. Specifically, a comparison between an exemplary nanoemulsion of the invention and conventional antifungal drugs itraconazole, Terbinafine, and ciclopirox) in killing *Trichophyton rubrum*, *Trichophyton mentagrophytes*, and *Epidermophyton floccosum*, demonstrated that the nanoemulsion was as effective or better than conventional antifungal drugs in killing the primary pathogens causing onychomycosis. See Example 1.

Moreover, as described in Example 6, nanoemulsions according to the invention also demonstrate broad effectiveness against all nondermatophyte molds, such as *Aspergillus* spp., *Paecilomyces* spp., *Fusarium* spp., *Acremonium* spp., *Scopulariopsis* spp., *Scedosporium* spp., *Scytalydium* spp., *Alternaria* spp., *Epicoccum nigrum*, *Curvularia* spp., *Phoma* spp., and *Chaetomium* spp. In addition, the nanoemulsion showed activity against less common species of dermatophytes, such as *Trichophyton verrucosum*, and *Trichophyton soundanense*.

In one embodiment of the invention, the surfactant present in the nanoemulsion is a cationic surfactant. More than one surfactant or detergent can be present in the nanoemulsions of the invention. For example, the nanoemulsions can comprise a cationic surfactant in combination with a non-ionic surfactant or in combination with an anionic, and/or zwitterionic, and/or cationic surfactant and/or any combination thereof. In another embodiment of the invention, the nanoemulsion further comprises a chelating agent. The "topical" application can be to any superficial skin structure, hair, hair shaft, hair follicle, or any combination thereof. The organic solvent and the aqueous phase of the invention can be a non-phosphate based solvent.

In another method of the invention, described is a method of killing or preventing a fungal, mold, or yeast agent in a human subject in need thereof comprising topically administering to the human subject a nanoemulsion. The topical application is to skin surrounding a barrier, a fungal, yeast, and/or mold infection exists under the barrier, the skin under the barrier is at risk of a fungal, yeast and/or mold infection or worsening of an infection, and the nanoemulsion diffuses around the barrier, under the barrier, through an imperfection in the barrier, or a combination thereof. The barrier can be a nail, thickened stratum corneum, a hairshaft, a hair follicle, or any combination thereof. The nanoemulsion comprises droplets having an average diameter of less than about 1000 nm, and the nanoemulsion comprises an aqueous phase, at least one oil, at least one surfactant or detergent, and at least one organic solvent.

The nanoemulsion in and of itself has antifungal activity and does not need to be combined with another active agent to obtain therapeutic effectiveness. However, in one embodiment of the invention, the nanoemulsion can further comprise one or more additional active agents useful in treating, healing or palliating an onycomycosis infection, including but not limited to the addition of another antifungal agent.

One of the problems with conventional drugs used for treating onychomycosis, or fungal/yeast/mold infections of the skin and/or nails, is that fungal nail infections are generally located deep under the nail plate and even into the nail matrix, and topically applied conventional treatments have extreme difficulty in penetrating—or are unable to penetrate—the nail bed and matrix in sufficient amounts to produce a therapeutically effective treatment. Orally administered drugs may address this problem present in topically applied therapies, but orally administered drugs act systemically and, therefore, may cause hepatoxicity. Patients are warned of this and may be monitored with liver function tests. Systemic drugs also have limitations in spectrum and do not cover all fungi, yeast, and molds that cause onychomycosis or other *tinea* infections.

Surprisingly, the present invention is directed to the discovery that the nanoemulsions of the invention can be applied around a barrier covering an infection, such as a nail, and following application the nanoemulsion then migrates under (or laterally diffuses under) the barrier to effectively reach and eradicate the infection. Moreover, this result is obtained without systemic absorption, as a measurable quantity of the nanoemulsion is not found within the plasma of a treated subject (determined by measuring if any surfactant or detergent, such as a cationic surfactant present in the nanoemulsion, is absorbed into the bloodstream).

In one embodiment of the invention, the nanoemulsions of the invention provide a mycological cure for the condition to be treated (i.e., for the fungal infection and/or onychomycosis being treated). For example, in a method of the invention, the nanoemulsions described herein can provide a mycological cure, defined as negative results on microscopy and culture, 1 week after stopping treatment, 2 weeks after stopping treatment, 3 weeks after stopping treatment, 4 weeks after stopping treatment, 5 weeks after stopping treatment, 6 weeks after stopping treatment, 7 weeks after stopping treatment, 8 weeks after stopping treatment, 9 weeks after stopping treatment, 10 weeks after stopping treatment, 11 weeks after stopping treatment, 12 weeks after stopping treatment, 1 month after stopping treatment, 2 months after stopping treatment, 3 months after stopping treatment, 4 months after stopping treatment, 5 months after stopping treatment, or 6 months afters stopping treatment. This is in contrast to conventional topical treatments for antifungal infections, such as Penlac®, which provide minimal mycological cures after stopping treatment. In another embodiment of the invention, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% of the patient population treated exhibits a mycological cure for the fungal infection and/or onychomycosis being treated, following treatment with a nanoemulsion of the invention, based on any of the treatment intervals above (i.e., 1 weeks after stopping treatment, 2 weeks after stopping treatment, etc.). In yet another embodiment of the invention, the nanoemulsions of the invention provide an improved rate of mycological cure as compared to that obtained using a conventional, non-nanoemulsion topical antifungal treatment, such as Penlac®. In some embodiments of the invention, the difference between the mycological cure obtained with a nanoemulsion according to the invention as compared to a conventional non-nanoemulsion treatment, such as Penlac®, is 25% greater, 50% greater, 75% greater, 100% greater, 125% greater, 150% greater, 175% greater, 200% greater, 225% greater, 250% greater, 275% greater, 300% greater, 325% greater, 350% greater, 375% greater, 400% greater, 425% greater, 450% greater, 475% greater, or 500% greater.

In one embodiment of the invention, the nanoemulsion comprises: (a) an aqueous phase; (b) about 1% oil to about 80% oil; (c) about 0.1% organic solvent to about 50% organic solvent; (d) about 0.001% surfactant or detergent to about 10% surfactant or detergent; (e) about 0.0005% to about 1.0% of a chelating agent; or (f) any combination thereof. In another embodiment of the invention, the nanoemulsion comprises: (a) about 10% oil to about 80% oil; (b) about 1% organic solvent to about 50% organic solvent; (c) at least one non-ionic surfactant present in an amount of about 0.1% to about 10%; (d) at least one cationic agent present in an amount of about 0.01% to about 2%; (e) about 0.0005% to about 1.0% of a chelating agent; or (f) any combination thereof. The nanoemulsion can further comprises an additional active agent, such as an antifungal agent.

In yet another embodiment of the invention, the nanoemulsion additionally includes at least one suitable or desirable active agent useful in treating onychomycosis. The active agent can be present in a therapeutically effective amount, such as from about 0.1% up to about 99%, about 3% up to about 80%, about 5% up to about 60%, about 10% up to about 50%, or any combination thereof (e.g., about 3% up to about 10%).

The quantities of each components present in the nanoemulsion refer to a therapeutic nanoemulsion, and not to a nanoemulsion to be tested in vitro. This is significant, as nanoemulsions tested in vitro, such as the nanoemulsions described in the examples, generally have lower concentrations of oil, organic solvent, surfactant or detergent, and (if present) chelating agent than that present in a nanoemulsion intended for therapeutic use, e.g., topical use. This is because in vitro studies do not require the nanoemulsion droplets to traverse the skin or other barriers. For topical (or intradermal) use, the concentrations of the components must be higher to result in a therapeutic nanoemulsion. However, the relative quantities of each component used in a nanoemulsion tested in vitro are applicable to a nanoemulsion to be used therapeutically and, therefore, in vitro quantities can be scaled up to prepare a therapeutic composition, and in vitro data may well be predictive of topical application success.

A. Definitions

The present invention is described herein using several definitions, as set forth below and throughout the application.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "buffer" or "buffering agents" refer to materials which when added to a solution, cause the solution to resist changes in pH.

The terms "chelator" or "chelating agent" refer to any materials having more than one atom with a lone pair of electrons that are available to bond to a metal ion.

The term "dilution" refers to dilution of the nanoemulsions of the present invention or those derived from the nanoemulsions of the present invention using, for example, an aqueous system comprised of PBS or water (such as $diH_2O$), or other water soluble components, to the desired final concentration.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described by Meyers, (Meyers, Surfactant Science and Technology, VCH Publishers Inc., New York, pp. 231-245 [1992]), incorporated herein by reference. As used herein, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water which are good solubilizers of water in oils are at the low end of the scale.

The term "nanoemulsion," as used herein, includes dispersions or droplets, as well as other lipid structures that can form as a result of hydrophobic forces that drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The droplets have an average diameter of less than about 1000 nm.

The terms "pharmaceutically acceptable" or "pharmacologically acceptable," as used herein, refer to compositions that do not substantially produce adverse allergic or immunological reactions when administered to a host (e.g., an animal or a human). Such formulations include any pharmaceutically acceptable dosage form. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like.

The term "stable" when referring to a "stable nanoemulsion" means that the nanoemulsion retains its structure as an emulsion. A desired nanoemulsion structure, for example, may be characterized by a desired size range, macroscopic observations of emulsion science (is there one or more layers visible, is there visible precipitate), pH, and a stable concentration of one or more the components.

The term "subject" as used herein refers to organisms to be treated by the compositions of the present invention. Such organisms include animals (domesticated animal species, wild animals), and humans.

The term "surfactant" refers to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group.

As used herein, the term "systemically active drugs" is used broadly to indicate a substance or composition whose administration is not necessarily near the infection source and whose levels can be measured at sites quite distant from the site of administration (e.g., oral drug administration where levels of the drug are found in the bloodstream or in tissues or organs).

As used herein, the term "topically" refers to application of the compositions of the present invention to the surface of the skin or infected tissue and mucosal cells and tissues (e.g., alveolar, buccal, lingual, sublingual, masticatory, or nasal mucosa, and other tissues and cells which line hollow organs or body cavities).

As used herein, the term "topically active agents" refers to compositions of the present invention that are applied to skin or mucosal surfaces. Desired pharmacological results are intended at or near the site of application (contact) to a subject.

B. Properties of the Nanoemulsions of the Invention

The present invention provides a method of killing a fungal, yeast and/or mold agent causing a fungal, yeast and/or mold infection in a human subject in need thereof, wherein the fungal, yeast and/or mold agent is a *Trichophyton* spp., *Epidermophyton* spp., *Candida* spp., *Microsporum* spp., *Aspergillus* spp., *Paecilomyces* spp., *Fusarium* spp., *Acremonium* spp., *Chaetomium* spp., *Phoma* spp., *Scopulariopsis* spp., *Scytalidium* spp., *Alternaria* spp., *Epicoccum* spp., and/or *Curvularia* spp., or a combination thereof. The method comprises topically or intradermally administering a therapeutically effective amount of a nanoemulsion to a the human or animal subject.

Furthermore, the nanoemulsion of the invention, upon topical administration, is capable of penetrating natural barriers that are normally resistant to penetration to other topically applied agents in the human body. The nanoemulsion of the invention effectively treats and/or controls the fungal, yeast, viral, and/or mold infection without being systemically absorbed and/or causing significant irritation to the application site. The nanoemulsion droplets can traverse the skin pores and hair follicles. In addition, the nanoemulsion may be taken up, in part, by damaged or diseased skin, lateral or proximal folds, and/or hyponichium because the natural skin barrier has been breached. Nanoemulsions according to the invention are not solely reliant upon penetration of the nail to reach the site of fungal infection, the nail bed and/or matrix. The nanoemulsion effectively treats the fungal, yeast and/or mold infection by killing or inhibiting the growth of the fungal, yeast, and/or mold agent, causing the fungal, yeast, and/or mold agent to lose pathogenicity, or any combination thereof.

The nanoemulsion of the invention effectively treats and/or controls a fungal, yeast, and/or mold infection without being systemically absorbed or causing significant irritation to the application site.

The nanoemulsion may be fungicidal against the fungal, yeast and/or mold agent, fungistatic, or a combination thereof. In one embodiment of the invention, the nanoemulsion has a narrow distribution of MIC (minimum inhibitory concentration) and MFC (minimum fungicidal concentrations) values. When the nanoemulsion is fungicidal, the MIC and MFC for the nanoemulsion differ by less than or equal to four-fold. When the nanoemulsion is fungistatic, the MIC and MFC for the nanoemulsion differ by greater than four-fold. See FIG. 3. The MFC is sometimes referred to as the MLC (minimum lethal concentration).

For example, FIG. 3 graphically compares the fungicidal effect, expressed as minimum inhibitory concentration (MIC) and minimum fungicidal concentration (MFC) values, of the nanoemulsion of the invention to the effect of other antifungal drugs currently used for the treatment of fungal infection, on fungi isolates of *Trichophyton rubrum*. (A) Nano emulsion ("NB-002"); (B) terbinafine; (C) ciclopirox; and (D) itraconazole. The nanoemulsion is consistently fungicidal (MFC:MIC ratio of $\leq 4$) whereas the other antifungal drugs cause either a fungistatic (MFC:MIC>4) or fungicidal effect on different clinical isolates of *Trichophyton rubrum*. A fungicidal treatment is much more desirable than a fungistatic treatment, as a fungicidal may be much more effective in completely "curing" the infection, as well as preventing infection reoccurrence, and isn't as reliant on a functioning immune system.

In addition, the nanoemulsion may be therapeutically effective against the fungal, yeast, and/or mold agent. Preferably, the nano emulsion is fungicidal or fungi static and is effective against fungal conidia, hyphae and mycelia, yeast haploid and diploid cells, and mold, or any combination thereof. An MIC value of from about 0.25 to about 100 µg cationic agent/ml against *Trichophyton* spp., against *Epidermophyton* spp., *Microsporum* spp. or against *Candida* spp. from about 0.25 to about 32 µg cationic agent/ml indicates that the nanoemulsion is inhibiting the growth of the fungi or yeast or mold. In exemplary embodiments of the invention:

(1) the organism is *Trichophyton* spp. and the MIC ranges from about 0.25 to about 25 µg cationic agent/ml, and/or the MFC ranges from about 0.25 to about 100 µg cationic agent/ml;

(2) the organism is *Epidermophyton* spp. and the MIC ranges from about 0.25 to about 25 µg cationic agent/ml and/or the MFC is about 0.25 to about 100 µg cationic agent/ml;

(3) the organism is *Candida* spp., and the MIC ranges from about 0.25 to about 25 µg cationic agent/ml and/or the MFC is 0.25 to about 100 µg cationic agent/ml;

(4) the organism is *Microsporum* spp. and the MIC ranges from about 0.25 to about 25 µg cationic agent/ml, and/or the MFC ranges from about 0.25 to about 100 µg cationic agent/ml;

(5) the organism is *Aspergillus* spp. and the MIC ranges from about 0.25 to about 25 µg cationic agent/ml, and/or the MFC ranges from about 0.25 to about 100 µg cationic agent/ml;

(6) the organism is *Paecilomyces* spp. and the MIC ranges from about 0.25 to about 25 µg cationic agent/ml, and/or the MFC ranges from about 0.25 to about 100 µg cationic agent/ml;

(7) the organism is *Fusarium* spp. and the MIC ranges from about 0.25 to about 25 µg cationic agent/ml, and/or the MFC ranges from about 0.25 to about 100 µg cationic agent/ml;

(8) the organism is *Acremonium* spp. and the MIC ranges from about 0.25 to about 25 µg cationic agent/ml, and/or the MFC ranges from about 0.25 to about 100 µg cationic agent/ml;

(9) the organism is *Chaetomium* spp. and the MIC ranges from about 0.25 to about 25 µg cationic agent/ml, and/or the MFC ranges from about 0.25 to about 100 µg cationic agent/ml;

(10) the organism is *Phoma* spp. and the MIC ranges from about 0.25 to about 25 µg cationic agent/ml, and/or the MFC ranges from about 0.25 to about 100 µg cationic agent/ml;

(11) the organism is *Scopulariopsis* spp. and the MIC ranges from about 0.25 to about 25 µg cationic agent/ml, and/or the MFC ranges from about 0.25 to about 100 µg cationic agent/ml;

(12) the organism is *Scytalidium* spp. and the MIC ranges from about 0.25 to about 25 µg cationic agent/ml, and/or the MFC ranges from about 0.25 to about 100 µg cationic agent/ml;

(13) the organism is *Alternaria* spp. and the MIC ranges from about 0.25 to about 25 µg cationic agent/ml, and/or the MFC ranges from about 0.25 to about 100 µg cationic agent/ml;

(14) the organism is *Epicoccum* spp. and the MIC ranges from about 0.25 to about 25 µg cationic agent/ml, and/or the MFC ranges from about 0.25 to about 100 µg cationic agent/ml; or

(15) the organism is *Curvularia* spp. and the MIC ranges from about 0.25 to about 25 µg cationic agent/ml, and/or the MFC ranges from about 0.25 to about 100 µg cationic agent/ml.

The nanoemulsions of the invention are safe and can successfully treat and/or completely cure fungal, yeast and/or mold infections without causing significant skin irritation or being systemically absorbed. The nanoemulsions bind to the fungal cell surface, killing or inhibiting growth of the cell and preventing the growth/spread of the infection. Further, the nanoemulsions of the invention kill the resting spores or hyphae of the fungi, thus limiting the potential for disease recurrence.

C. Stability of the Nanoemulsions of the Invention

The nanoemulsions of the invention can be stable at about 40° C. and about 75% relative humidity for a time period of at least up to about 1 month, at least up to about 3 months, at least up to about 6 months, at least up to about 12 months, at least up to about 18 months, at least up to about 2 years, at least up to about 2.5 years, or at least up to about 3 years.

In another embodiment of the invention, the nanoemulsions of the invention can be stable at about 25° C. and about 60% relative humidity for a time period of at least up to about 1 month, at least up to about 3 months, at least up to about 6 months, at least up to about 12 months, at least up to about 18 months, at least up to about 2 years, at least up to about 2.5 years, or at least up to about 3 years, at least up to about 3.5 years, at least up to about 4 years, at least up to about 4.5 years, or at least up to about 5 years.

Further, the nanoemulsions of the invention can be stable at about 4° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

D. Fungal Infections

The fungal, yeast and/or mold infection to be treated, prevented, and/or cured may be a *tinea* infection, dermatophytoses, or a dermatophytoma. Fungal infections, as described herein, include, but are not limited to, infections of the human nail, nail bed, nail matrix, nail plate, paronychia, chronic paronychia, etc. Specific examples of these conditions to be treated, prevented, and/or cured include, but are not limited to, *Tinea pedis, Tinea unguium, Tinea corporis, Tinea cruris, Tinea capitis, Tinea manuum, Tinea barbae, Tinea facilae, Tinea versicolor*, onychomycosis, fungal keratitis, or any combination thereof.

Onychomycosis, as defined herein, is a chronic, persistent fungal infection of the nail bed which causes thickening and discoloration of the nail, sometimes accompanied by pain and disability. Onychomycosis can be caused by, for example, a dermatophyte or a filamentous fungi, such as *Trichophyton* spp., *Epidermophyton* spp., *Fusarium* spp., *Aspergillus* spp., *Paecilomyces* spp., *Acremonium* spp., *Scytalydium* spp., *Scopulariopsis* spp., *Scedosporium* spp., *Alternaria* spp., *Epicoccum* spp., *Curvularia* spp., *Phoma* spp., *Chaetomium* spp., and *Microsporum* spp.

E. Pathogens

The fungal infections contemplated in the present invention are caused by a *Trichophyton* spp., *Epidermophyton* spp., *Candida* spp., *Microsporum* spp., *Aspergillus* spp., *Paecilomyces* spp., *Fusarium* spp., *Acremonium* spp., *Chaetomium* spp., *Phoma* spp., *Scopulariopsis* spp., *Scytalidium* spp., *Alternaria* spp., *Epicoccum* spp., *Curvularia* spp., or a combination thereof. The invention encompasses methods and compositions of treating infection caused by any species of these genera.

In one embodiment of the invention, the fungal, yeast and/ or mold infection to be treated, prevented, and/or cured with the nanoemulsions of the invention is caused by *Trichophyton rubrum, T. tonsurans, T. mentagrophytes, T. soudanense, T. verrucosum, T. ajelloi, T. concentricum, T. equinum, T. erinacei, T. flavescens, T. gloriae, T. interdigitale, T. megnini, T. phaseoliforme, T. schoenleini, T. simii, T. terrestre, T. tonsurans, T. vanbreuseghemii, T. violaceum, T. yaoundei, Epidermophyton floccosum, E. stockdaleae, Candida albicans, Candida parapsiliosis, Candida krusei, Candida tropicalis, Candida glabrata, Candida parapsilosis, Candida lusitaniae, Candida kefyr, Candida guilliermondii, Candida dubliniensis, Microsporum canis, M. gypseum, M. audouini, M. gallinae, M ferrugineum, M. distortum, M. nanum, M. cookie, M. vanbreuseghemii, Epicoccum nigrum, Aspergillus sydowii, Aspergillus terreus, Aspergillus niger, Aspergillus terreus, Aspergillus fumigatus, Aspergillus flavus, Aspergillus clavatus, Aspergillus glaucus* group, *Aspergillus nidulans, Aspergillus oryzae, Aspergillus terreus, Aspergillus ustus, Aspergillus versicolor, Paecilomyces lilacinus, P. variotii, Fusarium oxysporum, F. solani, F. semitectum, Chaetomium atrobrunneum, Chaetomium funicola, Chaetomium globosum, Chaetomium strumarium, Scopulariopsis brevicaulis, Scopulariopsis candida, Scopulariopsis koningii, Scopulariopsis acremonium, Scopulariopsisflava, Scopulariopsis cinerea, Scopulariopsis trigonospora, Scopulariopsis brumptii, Scopulariopsis chartarum, Scopulariopsis fusca, Scopulariopsis asperula, Scytalidium dimidiatum, Scytalidium hyalinum, Scytalidium infestans, Scytalidium japonicum, Scytalidium lignicola, Alternaria alternate, Alternaria chartarum, Alternaria dianthicola, Alternaria geophilia, Alternaria infectoria, Alternaria stemphyloides, Alternaria teunissima, Curvularia brachyspora, Curvularia clavata, Curvularia geniculata, Curvularia lunata, Curvularia pallescens, Curvularia senegalensis, Curvularia verruculosa*, or any combination thereof.

Molds, as defined herein, include, but are not limited to infections caused by the fungi *Acremonium* spp., *Aspergillus* spp. (e.g., *A. sydowii, A. terreus, A. niger*), *Fusarium* spp. (e.g., *F. oxysporum, F. solani, F. semitectum*), *Scopulariopsis* spp. (e.g., *Scopulariopsis brevicaulis*), *Scedosporuim* spp., *Alternaria* spp., *Paecilomyces lilacinus, Epiccocum nigrum, Phoma* spp. *Chaetomium* spp., *Curvularia* spp., and *Scytalidium* spp., (e.g., *S. dimidiatum*).

Yeast, as defined herein, include, but are not limited to, *Candida* species causing yeast infections, including infections of the periungual area and the area underneath the nailbed, onychomycosis, nail dystrophy, onycholysis, and chronic paronychia. In addition, *Candida* infections of the skin can occur between the fingers, toes, around the anus, the penis, under pendulous breasts or in genital skin folds. Examples of *Candida* spp. include, but are not limited to, *C. albicans, C. parapsilosis*, and *C. krusei*.

F. Nanoemulsions

The term "nanoemulsion", as defined herein, refers to a dispersion or droplet or any other lipid structure. Typical lipid structures contemplated in the invention include, but are not limited to, unilamellar, paucilamellar and multilamellar lipid vesicles, micelles and lamellar phases.

The nanoemulsion of the present invention comprises droplets having an average diameter size of less than about 1,000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 ml, or any combination thereof. In one embodiment, the droplets have an average diameter size greater than about 125 nm and less than or equal to about 300 nm. In a different embodiment, the droplets have an average diameter size greater than about 50 nm or greater than about 70 nm, and less than or equal to about 125 nm.

1. Aqueous Phase

The aqueous phase can comprise any type of aqueous phase including, but not limited to, water (e.g., $H_2O$, distilled water, tap water) and solutions (e.g., phosphate-buffered saline (PBS) solution). In certain embodiments, the aqueous phase comprises water at a pH of about 4 to 10, preferably about 6 to 8. The water can be deionized (hereinafter "DiH$_2$O"). In some embodiments the aqueous phase comprises phosphate-buffered saline (PBS). The aqueous phase may further be sterile and pyrogen free.

2. Organic Solvents

Organic solvents in the nanoemulsions of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

3. Oil Phase

The oil in the nanoemulsion of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

4. Surfactants/Detergent

The surfactant or detergent in the nanoemulsion of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thighlycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or disterate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N—N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-114, Triton® X-165, Triton®X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-

Triazine-1,3,5(2H,4H,6H)-triethanol, 1-Decanaminium, N-decyl-N,N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl) phenoxy)ethoxy)ethyl dimethyl benzyl ammonium chloride, Alkyl 1 or 3 benzyl-1-(2-hydroxyethyl)-2-imidazolinium chloride, Alkyl bis(2-hydroxyethyl)benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl didecyl dimethyl ammonium chloride, Alkyl dimethyl benzyl ammonium chloride (C12-16), Alkyl dimethyl benzyl ammonium chloride (C12-18), dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 300% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl(ethylbenzyl) ammonium chloride (C12-18), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris (2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4,1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, minimum 98% (TLC), CHAPS, for electrophoresis, minimum 98% (TLC), CHAPSO, minimum 98%, CHAPSO, CHAPSO, for electrophoresis, 3-(Decyldimethylammonio)propanesulfonate inner salt, 3-Dodecyldimethylammonio)propanesulfonate inner salt, 3-(Dodecyldimethylammonio)propanesulfonate inner salt, 3-(N,N-Dimethylmyristylammonio) propanesulfonate, 3-(N,N-Dimethyloctadecylammonio) propanesulfonate, 3-(N,N-Dimethyloctylammonio) propanesulfonate inner salt, 3-(N,N-Dimethylpalmitylammonio)propanesulfonate, semi-synthetic derivatives thereof, and combinations thereof.

In some embodiments, the nanoemulsion comprises a cationic surfactant, which can be cetylpyridinium chloride. In other embodiments of the invention, the nanoemulsion comprises a cationic surfactant, and the concentration of the cationic surfactant is less than about 5.0% and greater than about 0.001%. In yet another embodiment of the invention, the nanoemulsion comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion is less than about 5.0% and greater than about 0.001%.

In another embodiment of the invention, the nanoemulsion comprises at least one cationic surfactant and at least one non-cationic surfactant. The non-cationic surfactant is a non-ionic surfactant, such as a polysorbate (Tween), such as polysorbate 80 or polysorbate 20. In one embodiment, the non-ionic surfactant is present in a concentration of about 0.05% to about 7.0%, or the non-ionic surfactant is present in a concentration of about 0.3% to about 4%. In yet another embodiment of the invention, the nanoemulsion comprises a cationic surfactant present in a concentration of about 0.01% to about 2%, in combination with a nonionic surfactant.

5. Active Agents

Optionally, a second active agent, other than the nanoemulsion, which provides palliative or therapeutic effects, such as an antifungal, antiyeast or antimold agent, is incorporated into the nanoemulsion to achieve improved absorption of the active agent or to provide additive/synergetic effects or to shorten treatment duration. Any active agent useful in treating, healing or palliating an onycomycosis infection, a fungal infection or onychomycosis can be incorporated into the nanoemulsion, including but not limited to the addition of another antifungal agent.

Exemplary active agents include, but are not limited to, (1) azoles (imidazoles), (2) antimetabolites, (3) allylamines, (4) morpholine, (5) glucan synthesis inhibitors (chemical family: echinocandins), (6) polyenes, (7) benoxaborales, (8) other antifungal/onychomycosis agents, and (9) new classes of antifungal/onychomycosis agents.

Examples of azoles include, but are not limited to, Bifonazole, Clotrimazole, Econazole, Miconazole, Tioconazole, Fluconazole, Itraconazole, Ketoconazole, Pramiconazole, Ravuconazole, Posaconazole, and Voriconazole. An example of an antimetabolite includes, but is not limited to, Flucytosine. Examples of allylamines include, but are not limited to, Terbinafine and Naftidineand amorolfine. Examples of glucan Synthesis Inhibitors include, but are not limited to, Caspoflngin, Micafungin, and Anidulafungin. Examples of polyenes include, but are not limited to, Amphotericin B, Nystatin, and pimaricin. An example of a benoxaborale is AN2690. Other examples of antifungal/onychomycosis agents include, but are not limited to, griseofulvin and ciclopirox. Finally, examples of new classes of antifungal/onychomycosis agents include, but are not limited to, sodarin derivatives and nikkomycins.

6. Additional Ingredients

Additional compounds suitable for use in the nanoemulsions of the invention include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion, or the additional compounds can be added to the original mixture to be emulsified. In certain of these embodiments, one or more additional compounds are admixed into an existing nanoemulsion composition immediately prior to its use.

Suitable preservatives in the nanoemulsions of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic Acid, alpha-tocophernol, ascorbic acid, ascorbyl palmitate, butylated hydroxyanisole, butylated hydroxytoluene, sodium ascorbate, Bis(p-chlorophenyldiguanido) hexane, 3-(-4-chloropheoxy)-propane-1,2-diol, Methyl and methylchloroisothiazolinone, sodium metabisulphite, citric acid, edetic acid, semi-synthetic derivatives thereof, and combinations thereof. Other suitable preservatives include, but are not limited to, benzyl alcohol, chlorhexidine (bis(p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion may further comprise at least one pH adjuster. Suitable pH adjusters in the nanoemulsion of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion can comprise a chelating agent. In one embodiment of the invention, the chelating agent is present in an amount of about 0.0005% to about 1.0%. Examples of chelating agents include, but are not limited to, Phytic Acid, Polyphosphoric acid, Citric acid, Gluconic acid, Acetic acid, Lactic Acid, ethylenediamine, ethylenediaminetetraacetic acid (EDTA), and dimercaprol and combinations thereof. A preferred chelating agent is ethylenediaminetetraacetic acid.

The nanoemulsion can comprise a buffering agent, such as a pharmaceutically acceptable buffering agent. Examples of buffering agents include, but are not limited to, 2-Amino-2-methyl-1,3-propanediol, $\geq 99.5\%$ (NT), 2-Amino-2-methyl-1-propanol, $\geq 99.0\%$ (GC), L-(+)-Tartaric acid, $\geq 99.5\%$ (T), ACES, $\geq 99.5\%$ (T), ADA, $\geq 99.0\%$ (T), Acetic acid, $\geq 99.5\%$ (GC/T), Acetic acid, for luminescence, $\geq 99.5\%$ (GC/T), Ammonium acetate solution, for molecular biology, ~5 M in $H_2O$, Ammonium acetate, for luminescence, $\geq 99.0\%$ (calc. on dry substance, T), Ammonium bicarbonate, $\geq 99.5\%$ (T), Ammonium citrate dibasic, $\geq 99.0\%$ (T), Ammonium formate solution, 10 M in $H_2O$, Ammonium formate, $\geq 99.0\%$ (calc. based on dry substance, NT), Ammonium oxalate monohydrate, $\geq 99.5\%$ (RT), Ammonium phosphate dibasic solution, 2.5 M in $H_2O$, Ammonium phosphate dibasic, $\geq 99.0\%$ (T), Ammonium phosphate monobasic solution, 2.5 M in $H_2O$, Ammonium phosphate monobasic, ≧99.5% (T), Ammonium sodium phosphate dibasic tetrahydrate, ≧99.5% (NT), Ammonium sulfate solution, for molecular biology, 3.2 M in H₂O, Ammonium tartrate dibasic solution, 2 M in H₂O (colorless solution at 20° C.), Ammonium tartrate dibasic, ≧99.5% (T), BES buffered saline, for molecular biology, 2× concentrate, BES, ≧99.5% (T), BES, for molecular biology, ≧99.5% (T), BICINE buffer Solution, for molecular biology, 1 M in H₂O, BICINE, ≧99.5% (T), BIS-TRIS, ≧99.0% (NT), Bicarbonate buffer solution, >0.1 M. Na₂CO₃, >0.2 M NaHCO₃, Boric acid, ≧99.5% (T), Boric acid, for molecular biology, ≧99.5% (T), CAPS, ≧99.0% (TLC), CHES, ≧99.5% (T), Calcium acetate hydrate, ≧99.0% (calc. on dried material, KT), Calcium carbonate, precipitated, ≧99.0% (KT), Calcium citrate tribasic tetrahydrate, ≧98.0% (calc. on dry substance, KT), Citrate Concentrated Solution, for molecular biology, 1 M in H₂O, Citric acid, anhydrous, ≧99.5% (T), Citric acid, for luminescence, anhydrous, ≧99.5% (T), Diethanolamine, ≧99.5% (GC), EPPS, ≧99.0% (T), Ethylenediaminetetraacetic acid disodium salt dihydrate, for molecular biology, ≧99.0% (T), Formic acid solution, 1.0 M in H₂O, Gly-Gly-Gly, ≧99.0% (NT), Gly-Gly, ≧99.5% (NT), Glycine, ≧99.0% (NT), Glycine, for luminescence, ≧99.0% (NT), Glycine, for molecular biology, ≧99.0% (NT), HEPES buffered saline, for molecular biology, 2× concentrate, HEPES, ≧99.5% (T), HEPES, for molecular biology, ≧99.5% (T), Imidazole buffer Solution, 1 M in H₂O, Imidazole, ≧99.5% (GC), Imidazole, for luminescence, ≧99.5% (GC), Imidazole, for molecular biology, ≧99.5% (GC), Lipoprotein Refolding Buffer, Lithium acetate dihydrate, ≧99.0% (NT), Lithium citrate tribasic tetrahydrate, ≧99.5% (NT), MES hydrate, ≧99.5% (T), MES monohydrate, for luminescence, ≧99.5% (T), MES solution, for molecular biology, 0.5 M in H₂O, MOPS, ≧99.5% (T), MOPS, for luminescence, 99.5% (T), MOPS, for molecular biology, ≧99.5% (T), Magnesium acetate solution, for molecular biology, ~1 M in H₂O, Magnesium acetate tetrahydrate, ≧99.0% (KT), Magnesium citrate tribasic nonahydrate, ≧98.0% (calc. based on dry substance, KT), Magnesium formate solution, 0.5 M in H₂O, Magnesium phosphate dibasic trihydrate, ≧98.0% (KT), Neutralization solution for the in-situ hybridization for in-situ hybridization for molecular biology, Oxalic acid dihydrate, ≧99.5% (RT), PIPES, ≧99.5% (T), PIPES, for molecular biology, ≧99.5% (T), Phosphate buffered saline, Phosphate buffered saline solution (autoclaved), Phosphate buffered saline, washing buffer for peroxidase conjugates in Western Blotting, 10× concentrate, piperazine, anhydrous, ≧99.0% (T), Potassium D-tartrate monobasic, ≧99.0% (T), Potassium acetate solution, for molecular biology, Potassium acetate solution, for molecular biology, 5 M in H₂O, Potassium acetate solution, for molecular biology, ~1 M in H₂O, Potassium acetate, ≧99.0% (NT), Potassium acetate, for luminescence, ≧99.0% (NT), Potassium acetate, for molecular biology, ≧99.0% (NT), Potassium bicarbonate, ≧99.5% (T), Potassium carbonate, anhydrous, ≧99.0% (T), Potassium chloride, ≧99.5% (AT), Potassium citrate monobasic, ≧99.0% (dried material, NT), Potassium citrate tribasic solution, 1 M in H₂O, Potassium formate solution, 14 M in H₂O, Potassium formate, ≧99.5% (NT), Potassium oxalate monohydrate, ≧99.0% (RT), Potassium phosphate dibasic, anhydrous, ≧99.0% (T), Potassium phosphate dibasic, for luminescence, anhydrous, ≧99.0% (T), Potassium phosphate dibasic, for molecular biology, anhydrous, ≧99.0% (T), Potassium phosphate monobasic, anhydrous, ≧99.5% (T), Potassium phosphate monobasic, for molecular biology, anhydrous, 99.5% (T), Potassium phosphate tribasic monohydrate, 95% (T), Potassium phthalate monobasic, ≧99.5% (T), Potassium sodium tartrate solution, 1.5 M in H₂O, Potassium sodium tartrate tetrahydrate, ≧99.5% (NT), Potassium tetraborate tetrahydrate, ≧99.0% (T), Potassium tetraoxalate dihydrate, ≧99.5% (RT), Propionic acid solution, 1.0 M in H₂O, STE buffer solution, for molecular biology, pH 7.8, STET buffer solution, for molecular biology, pH 8.0, Sodium 5,5-diethylbarbiturate, ≧99.5% (NT), Sodium acetate solution, for molecular biology, ~3 M in H₂O, Sodium acetate trihydrate, ≧99.5% (NT), Sodium acetate, anhydrous, ≧99.0% (NT), Sodium acetate, for luminescence, anhydrous, ≧99.0% (NT), Sodium acetate, for molecular biology, anhydrous, ≧99.0% (NT), Sodium bicarbonate, ≧99.5% (T), Sodium bitartrate monohydrate, ≧99.0% (T), Sodium carbonate decahydrate, ≧99.5% (T), Sodium carbonate, anhydrous, ≧99.5% (calc. on dry substance, T), Sodium citrate monobasic, anhydrous, ≧99.5% (T), Sodium citrate tribasic dihydrate, ≧99.0% (NT), Sodium citrate tribasic dihydrate, for luminescence, ≧99.0% (NT), Sodium citrate tribasic dihydrate, for molecular biology, ≧99.5% (NT), Sodium formate solution, 8 M in H₂O, Sodium oxalate, ≧99.5% (RT), Sodium phosphate dibasic dihydrate, ≧99.0% (T), Sodium phosphate dibasic dihydrate, for luminescence, ≧99.0% (T), Sodium phosphate dibasic dihydrate, for molecular biology, ≧99.0% (T), Sodium phosphate dibasic dodecahydrate, ≧99.0% (T), Sodium phosphate dibasic solution, 0.5 M in H₂O, Sodium phosphate dibasic, anhydrous, ≧99.5% (T), Sodium phosphate dibasic, for molecular biology, ≧99.5% (T), Sodium phosphate monobasic dihydrate, ≧99.0% (T), Sodium phosphate monobasic dihydrate, for molecular biology, ≧99.0% (T), Sodium phosphate monobasic monohydrate, for molecular biology, ≧99.5% (T), Sodium phosphate monobasic solution, 5 M in H₂O, Sodium pyrophosphate dibasic, ≧99.0% (T), Sodium pyrophosphate tetrabasic decahydrate, ≧99.5% (T), Sodium tartrate dibasic dihydrate, ≧99.0% (NT), Sodium tartrate dibasic solution, 1.5 M in H₂O (colorless solution at 20° C.), Sodium tetraborate decahydrate, ≧99.5% (T), TAPS, ≧99.5% (T), TES, ≧99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate-EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≧99.5% (NT), Triethanolamine, ≧99.5% (GC), Triethylamine, ≧99.5% (GC), Triethylammonium acetate buffer, volatile buffer, ~1.0 M in H₂O, Triethylammonium phosphate solution, volatile buffer, ~1.0 M in H₂O, Trimethylammonium acetate solution, volatile buffer, ~1.0 M in H₂O, Trimethylammonium phosphate solution, volatile buffer, ~1 M in H₂O, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≧99.0% (NT), Trizma® base, ≧99.8% (T), Trizma® base, ≧99.8% (T), Trizma® base, for luminescence, ≧99.8% (T), Trizma® base, for molecular biology, ≧99.8% (T), Trizma® carbonate, ≧98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≧99.0% (AT), Trizma® hydrochloride, for luminescence, ≧99.0% (AT), Trizma® hydrochloride, for molecular biology, ≧99.0% (AT), and Trizma® maleate, ≧99.5% (NT).

The nanoemulsion can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsions that may readily be diluted with water to a desired concentration without impairing their anti-fungal or antiyeast properties.

G. Pharmaceutical Compositions

The nanoemulsions of the invention may be formulated into pharmaceutical compositions that comprise the nanoemulsion in a therapeutically effective amount and suitable, pharmaceutically-acceptable excipients for topical or intradermal administration to a human subject in need thereof. Such excipients are well known in the art.

By the phrase "therapeutically effective amount" it is meant any amount of the nanoemulsion that is effective in treating the fungal, yeast and/or mold infection by killing or inhibiting the growth of the fungal, yeast and/or mold agent, causing the fungal, yeast and/or mold agent to lose pathogenicity, or any combination thereof.

Topical and intradermal administration include administration to toenails, fingernails, the skin or mucosa, including surfaces of the hair, hair follicle, hair shaft, scrotum, mouth, ear, nose and eye.

Pharmaceutically acceptable dosage forms for topical or intradermal administration include, but are not limited to, ointments, creams, liquids, emulsions, lotions, gels, bioadhesive gels, aerosols, shampoos, pastes, foams, sunscreens, capsules, microcapsules, or in the form of an article or carrier, such as a bandage, insert, syringe-like applicator, pessary, powder, talc or other solid, shampoo, cleanser (leave on and wash off product), and agents that favor penetration within the epidermis, the dermis and keratin layers.

Intradermal administration refers to injection of the nanoemulsion according to the invention between layers of skin. Intradermal administration is intended to impart a cutaneous effect, while keeping the pharmacological effects of the nanoemulsion localized to the intracutaneous regions of penetration and deposition. Intradermal absorption occurs with little or no systemic absorption or accumulation.

The pharmaceutical compositions may be formulated for immediate release, sustained release, controlled release, delayed release, or any combinations thereof, into the epidermis or dermis, with no systemic absorption. In some embodiments, the formulations may comprise a penetration-enhancing agent for enhancing penetration of the nanoemulsion through the stratum corneum and into the epidermis or dermis. Suitable penetration-enhancing agents include, but are not limited to, alcohols such as ethanol, triglycerides and aloe compositions. The amount of the penetration-enhancing agent may comprise from about 0.5% to about 40% by weight of the formulation.

In some embodiments, the formulation for intradermal administration comprising a therapeutically effective amount of the nanoemulsion and administration into the area near the fungal or yeast or mold infection.

In some embodiments, the formulation for delivery via a "patch" comprising a therapeutically effective amount of the nanoemulsion is envisioned. As used herein a "patch" comprises at least a topical formulation and a covering layer, such that the patch can be placed over the area to be treated. Preferably, the patch is designed to maximize delivery through the stratum corneum and into the epidermis or dermis, while minimizing absorption into the circulatory system, and little to no skin irritation, reducing lag time, promoting uniform absorption, and reducing mechanical rub-off and dehydration.

Adhesives for use with the drug-in-adhesive type patches are well known in the art. Suitable adhesive include, but are not limited to, polyisobutylenes, silicones, and acrylics. These adhesives can function under a wide range of conditions, such as, high and low humidity, bathing, sweating etc. Preferably the adhesive is a composition based on natural or synthetic rubber; a polyacrylate such as, polybutylacrylate, polymethylacrylate, poly-2-ethylhexyl acrylate; polyvinylacetate; polydimethylsiloxane; or and hydrogels (e.g., high molecular weight polyvinylpyrrolidone and oligomeric polyethylene oxide). The most preferred adhesive is a pressure sensitive acrylic adhesive, for example Durotak® adhesives (e.g., Durotak® 2052, National Starch and Chemicals). The adhesive may contain a thickener, such as a silica thickener (e.g., Aerosil, Degussa, Ridgefield Park, N.J.) or a crosslinker such as aluminumacetylacetonate.

Suitable release liners include but are not limited to occlusive, opaque, or clear polyester films with a thin coating of pressure sensitive release liner (e.g., silicone-fluorsilicone, and perfluorcarbon based polymers).

Backing films may be occlusive or permeable and are derived from synthetic polymers like polyolefin oils polyester, polyethylene, polyvinylidine chloride, and polyurethane or from natural materials like cotton, wool, etc. Occlusive backing films, such as synthetic polyesters, result in hydration of the outer layers of the stratum corneum while nonocclusive backings allow the area to breath (i.e., promote water vapor transmission from the skin surface). More preferably the backing film is an occlusive polyolefin foil (Alevo, Dreieich, Germany). The polyolefin foil is preferably about 0.6 to about 1 mm thick.

The shape of the patch can be flat or three-dimensional, round, oval, square, and have concave or convex outer shapes, or the patch or bandage can also be segmented by the user into corresponding shapes with or without additional auxiliary means.

The nanoemulsions of the invention can be applied and/or delivered utilizing electrophoretic delivery/electrophoresis. Such transdermal methods, which comprise applying an electrical current, are well known in the art.

Lack of systemic absorption may be monitored, for example, by measuring the amount of the surfactant, such as the cationic surfactant, in the plasma of the human subject undergoing treatment. Amounts of surfactant of equal to or less than about 10 ng/ml in the plasma confirms lack of systemic absorption. In another embodiment of the invention, minimal systemic absorption of the nanoemulsion occurs upon topical administration. Such minimal systemic can be determined by the detection of less than 10 ng/mL, less than 8 ng/mL, less than 5 ng/mL, less than 4 ng/mL, less than 3 ng/mL, or less than 2 ng/mL of the one or more surfactants present in the nanoemulsion in the plasma of the subject.

The pharmaceutical compositions for topical or intradermal administration may be applied in a single administration or in multiple administrations. The pharmaceutical compositions are topically or intradermally applied for at least once a week, at least twice a week, at least once a day, at least twice a day, multiple times daily, multiple times weekly, biweekly, at least once a month, or any combination thereof. The pharmaceutical compositions are topically or intradermally applied for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years. Between applications, the application area may be washed to remove any residual nanoemulsion.

Preferably, the pharmaceutical compositions are applied to the skin area in an amount of from about 0.001 mL/cm$^2$ to about 5.0 mL/cm$^2$. An exemplary application amount and area is about 0.2 mL/cm$^2$. Following topical or intradermal administration, the nanoemulsion may be occluded or semi-occluded. Occlusion or semi-occlusion may be performed by overlaying a bandage, polyoleofin film, impermeable barrier, or semi-impermeable barrier to the topical preparation. Preferably, after application, the treated area is covered with a dressing.

H. Exemplary Nanoemulsions

Several exemplary nanoemulsions are described below, although the methods of the invention are not limited to the use of such nanoemulsions. The components and quantity of each can be varied as described herein in the preparation of other nanoemulsions. For the tables, unless otherwise noted, all concentrations are expressed in terms of % w/w.

I. Clearing of Infection

Following a suitable treatment period (e.g., such as 6 weeks, 12 weeks, 24 weeks, or any period equal to or less than 1 year measured in weeks), partial or complete clearing of the infection may be determined by measuring an increase in unaffected linear nail growth or a decrease in affected area and comparing these parameters to the initial baseline.

The progression or regression status of the infection may also be determined by obtaining a fungal, yeast and/or mold culture from a sample taken from the affected area at different time intervals, or by visualization of fungal, mold, or yeast by treatment of a human cell culture sample with 10% KOH and staining with lactophenol cotton blue, Grocott silver stain, hematoxylin or eosin. KOH denatures the proteins in the human cell; such that only the fungal cells remain to be seen under the microscope. (The fungal cells can be stained/visualized utilizing other techniques, which are well known in the art.)

It is noted that the nanoemulsions tested in vitro, such as the nanoemulsions described in the examples, generally have lower concentrations of oil, organic solvent, surfactant, and (if present) chelating agent than that present in a nanoemulsion intended for topical use. This is because in vitro studies do not require the nanoemulsion droplets to traverse the skin. For topical (or intradermal) use, the concentrations of the components must be higher to result in a therapeutic effect.

TABLE 1

Exemplary Therapeutically Effective Nanoemulsions

| Form. (CPC % w/v) | Soybean oil % | Tween 20% | Ethanol % | CPC % (mg/mL) | EDTA % (mM) | H$_2$O % |
|---|---|---|---|---|---|---|
| Formulation #1; (0.50%) | 31.4 | 2.96 | 3.37 | 0.53 (5) | 0.037 (1) | 61.70 |
| Formulation #2; (0.25%) | 15.7 | 1.48 | 1.68 | 0.27 (2.5) | 0.0185 (0.5) | 80.85 |
| Formulation #3; (1.0%) | 62.79 | 5.92 | 6.73 | 1.068 (10) | 0.075 (2) | 23.42 |
| Formulation #4; (0.3%) | 18.84 | 1.78 | 2.02 | 0.320 (3) | 0.0222 (0.6) | 77.03 |
| Formulation #5; (0.1%) | 6.28 | 0.59 | 0.67 | 0.107 (1) | 0.0075 (0.2) | 92.34 |

Several additional exemplary nanoemulsions are described below. All of these nanoemulsions were shown to have antifungal activity in vitro. For therapeutic topical use on a subject, the concentrations of each component would be increased, as described above.

However, the relative quantities of each component used in a nanoemulsion tested in vitro are applicable to a nanoemulsion to be used therapeutically and, therefore, in vitro quantities can be scaled up to prepare a therapeutic composition, and in vitro data is often predictive of topical application success.

TABLE 2

Exemplary Nanoemulsions Having Antifungal Activity In Vitro

| Form. (CPC w/v %) | Soybean oil % | Tween 20% | Ethanol % | CPC % (µg/mL) | EDTA % (uM) | H2O % |
|---|---|---|---|---|---|---|
| Formulation #6; (0.0008%) | 0.050 | 0.00474 | 0.00538 | 0.00085 (8) | $5.96 \times 10^{-5}$ (1.6) | 99.94 |
| Formulation #7; (0.0004%) | 0.025 | 0.00237 | 0.00269 | 0.00043 (4) | $2.98 \times 10^{-5}$ (0.8) | 99.97 |
| Formulation #8; (0.0002%) | 0.013 | 0.00118 | 0.00135 | 0.00021 (2) | $1.49 \times 10^{-5}$ (0.4) | 99.98 |

J. Methods of Manufacture

The nanoemulsions of the invention can be formed using classic emulsion forming techniques. See e.g., U.S. 2004/0043041. See also the method of manufacturing nanoemulsions described in U.S. Pat. Nos. 6,559,189, 6,506,803, 6,635,676, 6,015,832, and U.S. Patent Publication Nos. 20040043041, 20050208083, 20060251684, and 20070036831, and WO 05/030172, all of which are specifically incorporated by reference.

For example, nanoemulsions can be formed by high speed homogenization of an oil, purified water, nonionic detergent, organic solvent and surfactant (such as, for example, a cationic surfactant). In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water. The nanoemulsions of the invention are stable, and do not decompose even after long storage periods. Certain nanoemulsions of the invention are non-toxic and safe when swallowed, inhaled, or applied to the skin of a subject.

The compositions of the invention can be produced in large quantities and are stable for many months at a broad range of temperatures. The nanoemulsion can have textures/consistencies ranging from that of a semi-solid cream to that of a thin lotion and can be applied topically by hand and sprayed onto a surface. As stated above, at least a portion of the emulsion may be in the form of lipid structures including, but not limited to, unilamellar, multilamellar, and paucliamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepare using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in an emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable fungi, yeast and/or mold in vitro to a detectable level. To determine the suitability of a particular candidate nanoemulsion against a desired fungi, yeast and/or mold, the nanoemulsion is exposed to the fungi, yeast and/or mold under standardized conditions to allow the determination of MIC (see M. Ghannoum, et. al. 2006. Interlaboratory study of quality control isolates for a broth microdilution method (modified CLSI M38-A) for testing susceptibilities of dermatophytes to antifungals. J Clin Microbiol. 44:4353-6 or NCCLS. *Reference Method for Broth Dilution Antifungal Susceptibility Testing of Yeasts; Approved Standard-Second Edition*. NCCLS document M27-A2 (ISBN 1-56238-469-4). NCCLS, 940 WestValley Road, Suite 1400, Wayne, Pa. 19087-1898 USA, 2002 or NCCLS. *Reference Method for Broth Dilution Antifungal Susceptibility Testing of Filamentous Fungi; Approved Standard*. NCCLS document M38-A (ISBN 1-56238-470-8). NCCLS, 940 West Valley Road, Suite 1400, Wayne, Pa. 19087-1898 USA, 2002). Alternatively, the fungi yeast or mold can be exposed to the nanoemulsion for one or more time periods in a side-by-side experiment with an appropriate control sample (e.g., a negative control such as water) and determining if, and to what degree, the nanoemulsion kills or disable the fungi, yeast and/or mold.

The nanoemulsion of the invention can be provided in many different types of containers and delivery systems. For example, in some embodiments of the invention, the nanoemulsions are provided in a cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles (e.g., sprayers, pressurized spray bottles).

K. Examples

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

EXAMPLES

Example 1

The Nanoemulsions have Potent Activity Against Fungal, Yeast and/or Mold Infections Nanoemulsions according to the invention were tested in an in vitro fungicidal assay to determine the minimum inhibitory concentration (MIC) and minimum fungicidal concentration (MFC) against laboratory and clinical dermatophyte isolates associated with fungal infections, as well as several *Candida* species. The nanoemulsions ("NB-002") comprised, in an aqueous medium, soybean oil, Tween 20® as a nonionic surfactant, ethanol, cetylpyridinium chloride (CPC) as a cationic surfactant, EDTA, and water.

Nanoemulsions used in this example are oil-in-water (o/w) emulsions with mean droplet diameters of ~200 nm. CPC resides at the interface between the oil and water phases. The hydrophobic tail of the surfactant distributes in the oil core and its polar head group resides in the water phase. The nanoemulsions are produced by mixing a water-immiscible oil phase into an aqueous phase to yield an emulsion. The emulsion is further processed to achieve the desired particle size.

Chemical Structure of Cetylpyridinium Chloride:

TABLE 3

Physical-chemical properties of cetylpyridinium chloride.

| CAS Number | 123-03-5 |
|---|---|
| Molecular Formula | $C_{21}H_{38}NCl$ |
| Molar Mass | 339.986 g/mol |
| Melting Point | 77° C., 350 K, 171° F. |
| CMC (critical micelle concentration) | 0.00124 M |

The nanoemulsion at 10 different concentrations contained varying concentrations of soybean oil, Tween 20®, ethanol, CPC, and EDTA, because serial dilutions were prepared and tested against different yeast or fungi: *C. albicans, C. parapsilosis, C. krusei, T. mentagrophytes, E. floccosum, T. tonsurans, M. canis, M. gypseum* and *T. rubrum*. In general, the standard methodology followed for MIC determination used microtiter broth dilution methodology as specified in a Ghannoum et. al (Ghannoum et. al., "Interlaboratory study of quality control isolates for a broth microdilution method (modified CLSI M38-A; CLSI. Reference Method for Broth Dilution Antifungal Suceptibility Testing of Filamentous Fungi: Approved Standard-Second Edition. CLSI document M38-A2. Wayne, Pa.: Clinical and Laboratory Standards Institute; 2008) for testing susceptibilities of dermatophytes to antifungals," *J. Clin. Microbiol.*, 44:4353-6 (2006)). Briefly, RPMI 1640 medium was used and a hemacytometer count of conidia was done to ensure that the initial inoculum was $1-3\times10^3$ colony-forming units (cfu)/ml. Premade microtiter plates containing each of the drugs at 2× the desired final concentration were serially diluted as described in the Clinical and Laboratory Standards Institute document for testing of filamentous fungi (NCCLS. *Reference Method for Broth Dilution Antifungal Susceptibility Testing of Filamentous Fungi, Approved Standard*. NCCLS document M38-A (ISBN 1-56238-470-8). NCCLS, 940 West Valley Road, Suite 1400, Wayne, Pa. 19087-1898 USA, 2002) were inoculated with 2× the final desired inoculum. The final volume in each well was 200 µl. Plates were incubated at 35° C. for 4 days. Plates were examined visually for 100% growth inhibition endpoints as compared to the control well. The inoculum level was increased from $1-3\times10^3$ cfU/ml to $1-3\times10^4$ cfU/ml to allow for determination of MFCs; MICs were also recorded. Removal of 100-200 µl from each well where there was no growth (at the MIC and concentrations above) afforded a minimum of 10-30 colonies per plate when there was a 3-log kill. Colony counts were determined on Sabourard Dextrose Agar after 4 days at 35° C.

The MIC (minimum inhibitor concentration) and MFC (minimum fungicidal concentration) values for the nanoemulsions were compared to the MIC and MFC values of antifungal drugs currently in use: ciclopirox, terbinafine, itraconazole, econazole, and griseofulvin. See FIG. 3, which graphically compares the minimum inhibitory concentration (MIC) and minimum fungicidal concentration (MFC) values, of the nanoemulsion of the invention to the effect of other antifungal drugs currently used for the treatment of fungal infection, on fungi isolates of *Trichophyton rubrum*. (A) Nanoemulsion ("NB-002"); (B) Terbinafine; (C) Ciclopirox; and (D) Itraconazole. In Table 3, the MIC/MFC range, the $MIC_{50}/MFC_{50}$, and the $MIC_{90}/MFC_{90}$ are shown for the 15 isolates of T rubrum. A $MIC_{50}/MFC_{50}$ or $MIC_{90}/MFC_{90}$ is the lowest concentration of antifungal agent that inhibits the growth of or kills, respectively, 50% or 90% of the fungal, yeast, or mold isolates. The MIC/MFC range lists the lowest and highest concentrations of antifungal agent as inhibitory or lethal for a study.

Ciclopirox olamine (also called Batrafen®, Loprox®, Penlac® and Stieprox®) is a synthetic antifungal agent for topical dermatologic use. Antifungal activity is produced by its chelation of critical trivalent cations resulting in downstream effects. Terbinafine hydrochloride (Lamisil®, Terbisil®, Zabel®) is a synthetic allylamine antifungal that inhibits squalene epoxidase, an enzyme involved in the biosynthesis of ergosterol. It is highly lipophilic in nature and tends to accumulate in skin, nails, and fatty tissues. The drug is mainly effective on the dermatophytes group of fungi. As a 1% cream or powder it is used for superficial skin infections such as *Tinea cruris, Tinea pedis*, and other types of ringworm. Oral 250 mg tablets are often prescribed for the treatment of onychomycosis of the toenail or fingernail due to dermatophytes. Itraconazole (Sporanox®) is an azole antifungal agent that is prescribed to patients with fungal infections and it inhibits lanosterol 14α-demethylase, another enzyme involved in ergosterol biosynthesis. The drug may be given orally or intravenously. Another azole, econazole (Pevaryl®) is an antimycotic topical cream used for the treatment of demmatomycoses. Finally, griseofulvin (also known as Grisovin) is an orally administered antifungal drug used to treat ringworm infections of the skin, nails, and scalp. It binds to microtubular proteins and inhibits cell mitosis. Fungal nail infections are located deep under the nail and even in the nail matrix to which topically applied conventional treatments can be difficult or unable to penetrate in sufficient amounts. Orally administered drugs may cause hepatoxicity, so patients are warned of this and may be monitored with liver function tests.

Table 4 shows the MIC and MFC values for *Trichophyton rubrum*, expressed as µg cetylpyridinium chloride (CPC)/ml. NB-002 is fungicidal, while the majority of other antifungals are fungistatic as judged by their respective $MFC_{90}/MIC_{90}$ ratio values.

TABLE 4

$MIC_{90}$ and $MFC_{90}$ Values (µg CPC/ml) for *Trichophyton rubrum* (n = 15)

| | Values (µg/ml) | | | | | |
|---|---|---|---|---|---|---|
| Active | MIC range | MFC range | $MIC_{50}$ | $MFC_{50}$ | $MIC_{90}$ | $MFC_{90}$ |
| NB-002 | 1-4 | 1-4 | 2 | 2 | 2 | 2 |
| Ciclopirox | 0.5-1 | 0.25-16 | 1 | 1 | 1 | 16 |
| Terbinafine | 0.0625-0.25 | 0.0156->1 | 0.125 | 0.25 | 0.25 | >1 |

TABLE 4-continued

MIC$_{90}$ and MFC$_{90}$ Values (μg CPC/ml) for *Trichophyton rubrum* (n = 15)

| Active | MIC range | MFC range | MIC$_{50}$ | MFC$_{50}$ | MIC$_{90}$ | MFC$_{90}$ |
|---|---|---|---|---|---|---|
| Itraconazole | 0.25-1 | 0.5->16 | 0.5 | 2 | 1 | >16 |
| Econazole | 0.0625-0.25 | 0.0625->16 | 0.125 | 0.5 | 0.25 | 4 |
| Griseofulvin | 0.25-4 | 1-16 | 2 | 2 | 4 | 4 |

Table 5 shows the MIC and MFC values for *Trichophyton mentagrophytes*, expressed as μg cetylpiridinium chloride (CPC)/ml. NB-002 is fungicidal, while the other antifungals are fungistatic as judged by their respective MFC$_{90}$/MIC$_{90}$ ratio values.

TABLE 5

MIC$_{90}$ and MFC$_{90}$ Values (μg CPC/ml) for *Trichophyton mentagrophytes* (n = 14)

| Active | MIC Range | MFC Range | MIC$_{50}$ | MFC$_{50}$ | MIC$_{90}$ | MFC$_{90}$ |
|---|---|---|---|---|---|---|
| NB-002 | 1-4 | 1-4 | 2 | 2 | 4 | 4 |
| Ciclopirox | 0.125-1 | 0.5->32 | 0.5 | 1 | 1 | 16 |
| Terbinafine | 0.0313-0.25 | 0.0156->1 | 0.0313 | 0.25 | 0.125 | >1 |
| Itraconazole | 0.0625-0.5 | 0.25->16 | 0.125 | 8 | 0.5 | >16 |
| Econazole | 0.125-0.25 | 0.125->16 | 0.25 | 8 | 0.25 | >16 |
| Griseofulvin | 0.25-4 | 0.25->16 | 0.5 | 8 | 2 | >16 |

Table 6 shows the MIC and MFC ranges for *Epidermophyton floccosum*, expressed as μg cetylpyridinium chloride (CPC)/ml. NB-002 looks consistently active against *E. floccosum* (MIC/MFC range of 2-41 g/ml or 41 g/ml, respectively) while the ranges of the MFCs for the other antifungals are considerably broader.

TABLE 6

MIC and MFC Ranges (μg CPC/ml) for *Epidermophyton floccosum* (n = 6)

| Active | MIC Range (μg/ml) | MFC Range (μg/ml) |
|---|---|---|
| NB-002 | 2-4 | 4 |
| Ciclopirox | 0.5 | 0.25->32 |
| Terbinafine | 0.0625-0.25 | 0.0313-1 |
| Itraconazole | 0.125-0.5 | 0.5->16 |
| Econazole | 0.0625-0.125 | 0.0625-4 |
| Griseofulvin | 1-2 | 1-16 |

Table 7 shows the MIC and MFC ranges for *T. tonsurans* and *M. canis*, expressed as μg cetylpyridinium chloride (CPC)/ml. NB-002 looks consistently active against both species (MIC/MFC range of 2-4 μg/ml or 4 μg/ml, respectively) while the *T. tonsurans* MFC ranges for griseofulvin are considerably broader.

TABLE 7

MIC and MFC Ranges (μg CPC/ml) for *Trichophyton tonsurans* and *Microsporum canis*

| | Values (μg/ml) | | | |
|---|---|---|---|---|
| | *T. tonsurans* (n = 6) | | *M. canis* (n = 5) | |
| Active | MIC range | MFC range | MIC range | MFC range |
| NB-002 | 2 | 4-8 | 0.5-1 | 1 |
| Terbinafine | 0.008-0.015 | 0.06-0.12 | 0.004-0.03 | 0.06-0.12 |
| Griseofulvin | 0.5-1 | 8->64 | ND | ND |

Table 8 shows that the nanoemulsion NB-002 is fungicidal for *Candida parapsilosis, Candida krusei*, and *Microsporum gypseum*.

TABLE 8

MIC and MFC Values ((μg CPC/ml) for *Candida* spp. and *Microsporum gypseum*

| Species | MIC (μg/ml) | MFC (μg/ml) |
|---|---|---|
| *Candida parapsilosis* | 1 | 1 |
| *Candida krusei* | 1 | 2 |
| *Microsporum gypseum* | 2 | 4 |

Finally, Table 9 shows the MIC and MFC values for *Candida albicans* isolates that are azole-susceptible or azole-resistant, expressed as μg cetylpyridinium chloride (CPC)/ml. NB-002 is fungicidal against *C. albicans* isolates that are azole-susceptible or azole-resistant due to target site mutations and/or multidrug-resistant pumps.

TABLE 9

MIC$_{50}$ and MFC$_{50}$ Values (μg CPC/ml) for *Candida albicans* Isolates

| | Values (μg/ml) | | | |
|---|---|---|---|---|
| | Azole-Susceptible (n = 10) | | Azole-Resistant (n = 24)* | |
| Active | MIC$_{90}$ | MFC$_{90}$ | MIC$_{90}$ | MFC$_{90}$ |
| NB-002 | 2 | 4 | 2 | 8 |
| Fluconazole | 0.5 | >64 | >64 | >64 |
| Ciclopirox | 4 | >32 | 1 | >32 |
| Terbinafine | >1 | >1 | >1 | >1 |
| Itraconazole | 0.5 | >16 | >16 | >16 |
| Amphotericin B | 2 | 2 | 2 | 4 |

*All isolates are azole-resistant; 4 and 6 isolates have up-regulated MDR pumps or ergosterol biosynthetic mutations, respectively The MIC and MFC values of the nanoemulsion against *Trichophyton, Epidermophyton*, and *Candida* species, three major genera that cause various fungal and yeast infections, ranged from 0.5-8 μg/ml compared to antifungal agents that showed minimal or no fungicidal activity. Further, the nanoemulsion (NB-002) has consistent inhibitory and fungicidal activity against *M. canis* and *T. tonsurans*, the two major pathogens in *tinea capitis* (Table 10).

These results clearly demonstrate the nanoemulsions of the invention are consistently more fungicidal, as compared to the fungistatic effect of other antifungal drugs currently in use.

Example 2

The Nanoemulsions Are Not Toxic and Are Not Systemically Absorbed

Twenty subjects with advanced distal subungual onychomycosis of the toenails, including onycholysis of at least 5 toenails, were randomized to be treated with a nanoemulsion comprising a cationic surfactant, with 0.25% (w/v) cetylpyridinium chloride (CPC) or a nanoemulsion comprising 0.5% (w/v) cetylpyridinium chloride (CPC) as the cationic surfactant. The composition of the two emulsions (% w/w), was as follows and is shown is Table 12: Nanoemulsion I: (1) 15.7% soybean oil; (2) 1.48% Tween 20; (3) 1.68% ethanol, (4) 0.27% CPC; (5) 80.85% water; and (6) 0.019% EDTA; and Nanoemulsion 2: (1) 31.4% soybean oil; (2) 2.96% Tween 20; (3) 3.37% ethanol, (4) 0.53% CPC; (5) 61.7% water; and (6) 0.037% EDTA.

TABLE 10

MIC values of NB-002 and comparators against species that cause tinea capitis.

| Tinea capitis species | NB-002 | | | Terbinafine | | | Griseofulvin | | |
|---|---|---|---|---|---|---|---|---|---|
| | Range | MIC$_{50}$ | MIC$_{90}$ | Range | MIC$_{50}$ | MIC$_{90}$ | Range | MIC$_{50}$ | MIC$_{90}$ |
| *T. tonsurans* n = 10 | 0.5-2.0 | 2.0 | 2.0 | 0.008-0.016 | 0.016 | 0.016 | 0.5-1.0 | 0.5 | 1.0 |
| *T. violaceum*$^a$ n = 10 | 0.5-2.0 | 1.0 | 2.0 | 0.008-0.03 | 0.03 | 0.03 | 1.0-8.0 | 4.0 | 4.0 |
| *M. canis* n = 10 | 0.25-2.0 | 1.0 | 1.0 | 0.06 | 0.06 | 0.06 | 0.25-0.5 | 0.25 | 0.5 |
| *M. audouinii*$^a$ n = 10 | 0.5-1.0 | 0.5 | 1.0 | 0.03-0.06 | 0.06 | 0.06 | 0.12-1.0 | 0.25 | 1.0 |

Table 11 shows an exemplary antifungal nanoemulsion tested for each of the four yeast/fungi. Unless otherwise noted, all concentrations are expressed as % w/w.

TABLE 11

Exemplary Nanoemulsions Exhibiting Antifungal/Antiyeast Activity

| | MFC (ug CPC/ mL) | Nanoemul. CPC % w/v | Soybean oil (%) | Tween 20 (%) | Ethanol (%) | CPC % (μg/mL) | EDTA % (μM) | H$_2$O (%) |
|---|---|---|---|---|---|---|---|---|
| *Candida albicans* | 8 | 0.0008% | 0.050 | 0.00474 | 0.00538 | 0.00085 (8) | 5.96 × 10$^{-5}$ (1.6) | 99.94 |
| *T. mentagrophytes* | 4 | 0.0004% | 0.025 | 0.00237 | 0.00269 | 0.00043 (4) | 2.98 × 10$^{-5}$ (0.8) | 99.97 |
| *E. floccosum* | 4 | 0.0004% | 0.025 | 0.00237 | 0.00269 | 0.00043 (4) | 2.98 × 10$^{-5}$ (0.8) | 99.97 |
| *T. rubrum* | 2 | 0.0002% | 0.013 | 0.00118 | 0.00135 | 0.00021 (2) | 1.49 × 10$^{-5}$ (0.4) | 99.98 |

TABLE 12

| Nanoemulsion | Soybean oil % | Tween 20% | Ethanol (%) | CPC % (mg/mL) | EDTA %(mM) | H₂O % |
|---|---|---|---|---|---|---|
| 0.50% (w/v) | 31.4 | 2.96 | 3.37 | 0.53 (5) | 0.0373 (1) | 61.70 |
| 0.25% (w/v) | 15.7 | 1.48 | 1.68 | 0.27 (2.5) | 0.019 (0.5) | 80.85 |

Treatments were applied twice daily to 10 toenails and to 5 mm of adjacent skin for 28 days, with a medium number of applications of 55. FIG. 4 shows a graphical mechanism of action of the nanoemulsion, including route of entry of nanoemulsion.

Safety was evaluated by adverse event reporting and scoring of dermal irritation on a 4-point scale on days 1, 3, 7, 14, 21, 28, and 58. Dermal irritation was assessed at each visit by grading the application site with respect to erythema, dryness/scaling, burning/stinging, and itching; each graded on a standard scoring scale where 0=none, 1=mild, 2=moderate, and 3=severe. Systemic drug absorption of the cationic agent was determined in plasma samples collected at 14 time points during the 28-day treatment period by high performance liquid chromatography (HPLC) using an SB-Phenyl column maintained at 35° C.

Table 13 summarizes the demographic characteristics of the human subjects receiving treatment.

TABLE 13

Subject Demographic Characteristics

| Parameter | Nanoemulsion with 0.25% CPC | Nanoemulsion with 0.5% CPC | Overall (N = 20) |
|---|---|---|---|
| Age (years) Mean (SD) | 52.5 (11.3) | 54.2 (5.5) | 53.3 (9.0) |
| Age (years) Median | 55.5 | 54.5 | 55 |
| Minimum, Maximum Age | 30.5, 64.9 | 43.4, 64.9 | 30.5, 64.9 |
| Male | 5 (50) | 7 (70) | 12 (60) |
| Female | 5 (50) | 3 (30) | 8 (40) |
| Race, n (%) White | 9 (90) | 8 (80) | 17 (85) |
| Race, n (%) Black | 1 (10) | 2 (20) | 3 (15) |

SD = Standard Deviation

Table 14 summarizes the adverse events registered during the study. There were no serious adverse events or discontinuations due to adverse events. All of the reported adverse events were mild to moderate in severity and none was considered treatment-related. The most commonly reported adverse event was common cold symptoms.

TABLE 14

Summary of Adverse Events

| Adverse Events Parameters (AE) | Nanoemulsion with 0.25% CPC | Nanoemulsion with 0.5% CPC |
|---|---|---|
| Number of Subjects with any AE | 2 | 2 |
| Subjects with any Treatment-Related AE | 0 | 0 |

TABLE 14-continued

Summary of Adverse Events

| Adverse Events Parameters (AE) | Nanoemulsion with 0.25% CPC | Nanoemulsion with 0.5% CPC |
|---|---|---|
| Number of AEs | 3 | 2 |
| Common Cold Symptoms | 1 | 1 |
| Head Congestion | 1 | 0 |
| Chest Congestion | 1 | 0 |
| Toenail Partially Torn Off | 0 | 1 |

None of the subjects in the trial reported any skin irritation at any time in the trial, and dermal irritation scoring by the investigators indicating no or minimal skin irritation from the nanoemulsion. At each study visit, the investigator rated the skin on a 4-point scale. In most subjects there were no findings at any time in the study. Five subjects had skin findings on one or more visits that were rated by the investigator to be mild. Four (4) of these subjects had mild findings on one or 2 study days only that resolved by the end of the study. One (10 subject had continued mild findings at all study visits. None of these findings were considered clinically significant by the investigator.

CPC was below the quantifiable limit (1 ng/mL) in the plasma samples for all subjects and at all sampling time points. These results clearly show that the nanoemulsions of the invention are well tolerated and not toxic, and are not systemically absorbed.

Example 3

The Nanoemulsions are Clinically Effective 443 subjects with distal subungual onychomycosis of the toenails involving 25-65% of the toenail area were enrolled in a randomized, double-blind vehicle controlled dose-ranging study and treated with vehicle, a nanoemulsion comprising 0.25% (w/v) cetylpyridinium chloride or a nanoemulsion comprising 0.5 w/v % cetylpyridinium chloride. The composition of the two nanoemulsions (% w/w) is described as follows: Nanoemulsion 1: (1) 15.7% soybean oil; (2) 1.48% Tween 20; (3) 1.68% ethanol, (4) 0.27% cetylpyridinium chloride (CPC); (5) 80.85% water; and (6) 0.019% EDTA; and Nanoemulsion 2: (1) 31.4% soybean oil; (2) 2.96% Tween 20; (3) 3.37% ethanol, (4) 0.53% cetylpyridinium chloride (CPC); (5) 61.7% water; and (6) 0.037% EDTA.

In all subjects, KOH tests and dermatophyte cultures performed on samples from the subjects enrolled in the study were positive, confirming the presence of a dermatophyte pathogen. Treatments were applied once (0.5%) or twice (0.25% and 0.5%) daily to 10 toenails and to 5 mm of adjacent skin for 42 weeks. Linear nail growth and % of affected area were evaluated in 160 human subjects after 24 weeks of treatment.

The results, shown in FIGS. 5-7, clearly demonstrate progression in the linear growth of new unaffected nail and progressive decrease in the area of affected nail associated with nanoemulsion treatment.

Specifically, FIG. 5 graphically illustrates the progression in the linear growth of new unaffected nail as assessed by trained investigators after treatment with (A) vehicle, (B) nanoemulsion comprising 0.25% cetylpyridinium chloride, given twice daily, (C) nanoemulsion comprising 0.5% cetylpyridinium chloride, given once daily, and (D) nanoemulsion comprising 0.5% cetylpyridinium chloride, given twice daily.

FIG. 6 graphically illustrates the progression in the linear growth of a new unaffected nail after treatment as assessed by planimetry with (A) vehicle, (B) nanoemulsion comprising 0.25% cetylpyridinium chloride, given twice daily, (C) nanoemulsion comprising 0.5% cetylpyridinium chloride, given once daily, and (D) nanoemulsion comprising 0.5% cetylpyridinium chloride, given twice daily.

FIG. 7 graphically illustrates the progressive decrease in the area of affected nail as assessed by planimetry after treatment with (A) vehicle, (B) nanoemulsion comprising 0.25% cetylpyridinium chloride, given twice daily, (C) nanoemulsion comprising 0.5% cetylpyridinium chloride, given once daily, and (D) nanoemulsion comprising 0.5% cetylpyridinium chloride, given twice daily.

Finally, the effectiveness of a nanoemulsion according to the invention ("NB-002") in providing a mycological cure was compared to that of Penlac®. Penlac® is the only topical medication approved by the FDA for treatment of mild and moderate nail fungus. It was surprisingly found that after 42 weeks of treatment with a nanoemulsion according to the invention (NB-002), followed by 4-8 weeks (or 1-2 months) of no treatment, a significant percentage of the patent population exhibited a mycological cure. This is in contrast to the results obtained with or Penlac®, where after 42 weeks of treatment, followed by 4-8 weeks (or 1-2 months) of no treatment, a minimal percentage of subjects treated exhibited a mycological cure. See FIG. 8, where it is shown that a nanoemulsion according to the invention provides a mycological cure rate, 8 weeks or more after stopping treatment, of over 25%. This result is unexpected and dramatic given the comparison results of Penlac®, which produced less than a 5% mycological cure 8 weeks or more after stopping treatment.

Example 4

The Nanoemulsions Are Safe for Topical Application at Doses 1000-Fold Higher than the Minimum Fungicidal Concentration In vivo safety studies were performed to confirm safety of the nanoemulsions for human use. The composition of the tested nanoemulsions (% w/w) is shown in Table 15.

TABLE 15

| Nanoemulsion (CPC concentration) | Soybean oil % | Tween 20% | Ethanol % | CPC % (mg/mL) | EDTA % (mM) | $H_2O$ |
|---|---|---|---|---|---|---|
| 10 mg/mL | 62.79 | 5.92 | 6.73 | 1.068 (10) | 0.0745 (2) | 23.42 |
| 5 mg/mL | 31.4 | 2.96 | 3.37 | 0.53 (5) | 0.0373 (1) | 61.70 |
| 3 mg/mL | 18.84 | 1.78 | 2.02 | 0.32 (3) | 0.0224 (0.6) | 77.03 |
| 1 mg/mL | 6.28 | 0.59 | 0.67 | 0.107 (1) | 0.0075 (0.2) | 92.34 |
| 0 mg/mL | 12.56 | 1.18 | 1.35 | 0 | 0.0149 (0.4) | 84.90 |

10 female and 10 male guinea pigs were treated to determine if the nanoemulsions led to dermal-sensitization by administration of 10 mg/ml of the nanoemulsion three times weekly for three consecutive weeks, and then challenged for 6 hrs one week later. Dermal toxicity studies were also performed in groups of 4 female and 4 male minipigs that were subject to administration of 0.1-1.0 mg/cm$^2$ of the nanoemulsion daily for 9 months.

Table 16 summarizes the results of the study.

TABLE 16

Summary of Toxicity Studies

| Study | Species | Route | Dose | Nanoemulsion Concentration | Duration | Group Size | Findings |
|---|---|---|---|---|---|---|---|
| Dermal Sensitization | Guinea Pig | Topical | 0.3 ml/chamber | 10 mg/ml | Induction: 3 times weekly for 6 hours for 3 consecutive weeks; challenge for 6 hours | 10/sex/group | No deaths occurred No contact sensitization occurred |
| Chronic Dermal | Minipig | Topical | 0, 0.1, 0.3, 05 mg/cm$^2$ | 0, 1, 3, 5 mg/ml | 273-274 Days | 4/sex/group | No deaths occurred |

Topical administration at concentrations 1000-fold higher than the MIC/MFC of dermatophytes did not cause dermal sensitization in guinea pigs and showed no toxicity in a 9-month repeat dose dermal study in minipigs. These results clearly demonstrate that the nanoemulsions of the invention are safe for topical application at doses 1000-fold higher than the minimum fungicidal concentration.

Example 5

The Nanoemulsions Are Stable

Nanoemulsions according to the invention were tested for stability according to ICH guidelines. The composition of the tested nanoemulsions (% w/w), was as follows (Table 17):

TABLE 17

| Nanoemulsion (CPC % w/v) | Soybean oil % | Tween 20 % | Ethanol % | CPC % (mg/mL) | EDTA % (mM) | $H_2O$ % |
|---|---|---|---|---|---|---|
| 0.50% | 31.4 | 2.96 | 3.37 | 0.53 (5) | 0.0373 (1) | 61.70 |
| 0.25% | 15.7 | 1.48 | 1.68 | 0.27 (2.5) | 0.019 (0.5) | 80.85 |

The nanoemulsions were stored in glass vials at 40° C./75% relative humidity (RH) for 6 months or at room temperature (25° C./60% RH) for 36 months. The nanoemulsions were assessed by general appearance (white homogenous liquid with no signs of separation), pH (4-6), droplet size (<400 nm), and potency. The cationic surfactant present in the nanoemulsion, cetylpyridinium chloride, was used as the reporter of the potency of the nanoemulsion droplets and was quantitated by HPLC. The nanoemulsion passed all criteria of the stability testing.

Example 6

Activity of the Nanoemulsion Against Rare Fungal Pathogens

The purpose of this example was to test the effectiveness of a nanoemulsion according to the invention against rare fungal pathogens of onychomycosis.

A nanoemulsion was prepared comprising soybean oil, Tween 20® as a nonionic surfactant, ethanol, cetylpyridinium chloride (CPC) as a cationic surfactant, EDTA, and water ("NB-002"). The droplets of the nanoemulsion had an average diameter of ~200 nm. The size and composition allows for selective uptake into hair follicles and pores.

The major pathogens in onychomycosis are the dermatophytes *Trichophyton rubrum* and *Trichophyton mentagrophytes*. As described above, nanoemulsions according to the invention are fungicidal against both of these species. In this experiment, the antifungal activity was determined for a nanoemulsion according to the invention against 12 genera of filamentous fungi and 2 new species of *Trichophyton*.

Methods: All fungi were from patients, many of which had onychomycosis or another *tinea* infection. The minimum inhibitory concentration (MIC) of NB-002 and comparator compounds was determined using methodology described in the Clinical Laboratory Standards Institute M 38-A. Two-fold serial dilutions of NB-002 from 32 µg CPC/ml to 0.125 µg CPC/ml were tested against each fungal isolate. The composition of the range is listed in Table 18.

TABLE 18

The composition of the NB-002 range of concentrations tested in microtiter-based MIC determinations.

| Conc. Nanoemulsion tested (µg CPC/ml)) | Nanoemu. (CPC % w/v) | Soybean oil (%) | Tween 20 (%) | Ethanol (%) | CPC % (µg/mL) | EDTA % (µM) | $H_2O$ (%) |
|---|---|---|---|---|---|---|---|
| 32 | 0.0032000 | 0.200928 | 0.018944 | 0.021536 | 0.003418 | 0.000238 | 99.75 |
| 0.125 | 0.0000125 | 0.0007849 | 0.000074 | $8.41 \times 10^{-5}$ | $1.34 \times 10^{-5}$ | $9.31 \times 10^{-7}$ | 100.00 |

Results: NB-002 was the most consistently active antifungal. This topical nanoemulsion distinguished itself against amphotericin B (AmB), itraconazole (ITR), and terbinafine (TER) because of its potency against *Scopulariopsis* spp. and *Scedosporium* spp. and was superior to ciclopirox (CPX) because of its activity against *Fusarium* spp. and *Paecilomyces* spp. See Table 19 and FIG. 9.

TABLE 19

| Species | Number of Isolates | MIC range (ug/ml) | | | | |
|---|---|---|---|---|---|---|
| | | NB-002 | AmB[a] | ITR | TER | CPX |
| *Aspergillus* spp. | 5 | 0.5-1 | 1-4 | 0.06-1 | 0.03-0.25 | 0.5-2 |
| *Paecilomyces* spp. | 4 | 2-8 | >16 | 1->8 | 0.25-0.5 | 8-16 |
| *Fusarium* spp. | 10 | 0.5-2 | 4->16 | 2->8 | 2->2 | 1-16 |
| *Acremonium* spp. | 5 | 0.5-2 | 0.5->16 | >8 | 0.125-1 | 0.5-4 |
| *Scopulariopsis* spp. | 5 | 0.5-1 | >16 | 4->8 | 1->2 | 0.5-2 |
| *Scedosporium* spp. | 5 | 0.25-1 | >16 | 4->8 | >2 | 0.5-8 |
| *Scytalydium* spp. | 10 | 1-2 | 0.5-1 | 4->8 | 0.125-1 | 0.5-1 |
| *Alternaria* spp. | 3 | 0.06-0.5 | 1 | 0.25-0.5 | 1-2 | 0.25-0.5 |
| *Epicoccum nigrum* | 3 | 0.06-1 | 0.25-1 | 0.25-0.5 | 0.03-0.06 | 0.125-2 |
| *Curvularia* spp. | 3 | 0.5 | 0.125-1 | 0.125-0.25 | 0.03-1 | 0.5-1 |

TABLE 19-continued

| Species | Number of Isolates | MIC range (ug/ml) | | | | |
|---|---|---|---|---|---|---|
| | | NB-002 | AmB[a] | ITR | TER | CPX |
| *Phoma* sp. | 3 | 0.5-1 | 0.5-2 | 0.06-0.5 | 0.03 | 0.5-1 |
| *Chaetomium* spp. | 3 | 0.25 | 0.5-4 | 0.5-1 | 1-2 | 0.25-0.5 |
| *Trichophyton verrucosum* | 3 | ≦0.03-0.06 | 0.125-0.25 | 0.06-0.125 | ≦0.004-0.015 | <=0.06-0.125 |
| *Trichophyton soundanense* | 3 | 0.06 | 0.125-0.25 | 0.125-0.25 | ≦0.004 | 0.125-0.25 |

[a]AmB = amphotericin B;
ITR = itraconazole;
TER = terbinafine;
CPX = ciclopirox Conclusions: These data extend the activity of nanoemulsions according to the invention to rare fungal species that can cause onychomycosis.

Example 7

Pathogens do not Exhibit Resistance Potential to Nanoemulsions

The purpose of this example was to determine if various dermatophytes exhibit resistance potential to nanoemulsions according to the invention.

A nanoemulsion was prepared (NB-002), comprising, in an aqueous medium, soybean oil, Tween 20® as a nonionic surfactant, ethanol, cetylpyridinium chloride (CPC) as a cationic surfactant, EDTA, and water. (The range of nanoemulsion compositions for this study are listed in Table 20). Spontaneous resistance to 2×, 4×, and 8× the MIC was determined.) Spontaneous resistance to the nanoemulsion and comparator compounds in major pathogens causing onychomycosis was determined.

Methods: An inoculum ($5 \times 10^3$ conidia/spot) from clinical isolates of *Trichophyton rubrum, Trichophyton mentagrophytes* and *Epidermophyton floccosum* grown on potato dextrose agar was used to determine agar-based MICs of the nanoemulsion ("NB-002"), ciclopirox (C), terbinafine (T) and itraconazole (I). Resistance development to compounds was determined by plating $10^7$ conidia onto RPMI 1640 agar plates containing 2×, 4× or 8× the MIC. Phenotypically resistant isolates were tested for MICs and compared to parental MICs.

Results: Only 1-5 isolates were recovered from any drug plate. No isolate had more than a two-fold increase in MIC from its parent.

TABLE 20

The composition of the NB-002 range of concentrations tested in resistance development experiments.

| Conc. Nanoemulsion tested (µg CPC/ml)) | Nanoemu. (CPC % w/v) | Soybean oil (%) | Tween 20 (%) | Ethanol (%) | CPC % (µg/mL) | EDTA % (µM) | H₂O (%) |
|---|---|---|---|---|---|---|---|
| 32 | 0.0032000 | 0.200928 | 0.018944 | 0.021536 | 0.003418 | 0.000238 | 99.75 |
| 0.0625 | 0.00000625 | 0.0003925 | 0.000037 | $4.21 \times 10^{-5}$ | $0.67 \times 10^{-5}$ | $4.66 \text{ c } 10^{-7}$ | 100.00 |

TABLE 21

| | | Drug plate | | | Final MIC (µg/ml) | | | |
|---|---|---|---|---|---|---|---|---|
| Species[a] | Isolate # | Selecting Compound | (µg/ml) | # CFU recovered | NB-002 | T[b] | I[b] | C[b] |
| *E. floc.* | NBD006-a | NB-002 | 32 | 1 | 4.0 | 0.016 | 0.25 | 4 |
| *T. ment.* | NBD012-a | NB-002 | 8 | 2 | 4.0 | 0.031 | 0.0625 | 4 |
| *T. ment.* | NBD012-b | NB-002 | 16 | 1 | 4.0 | 0.031 | 0.0625 | 4 |
| *T. ment.* | NBD012-c | NB-002 | 32 | 1 | 4.0 | 0.016 | 0.0625 | 4 |
| *T. ment.* | NBD012-d | T | 0.0625 | 2 | 4.0 | 0.031 | 0.0625 | 4 |
| *T. ment.* | NBD013-a | I | 0.25 | 1 | 8.0 | 0.016 | 0.125 | 4 |
| *T. ment.* | NBD014-a | NB-002 | 32 | 5 | 4.0 | 0.016 | 0.0625 | 4 |
| *T. rubrum* | NBD031-a | NB-002 | 16 | 1 | 2.0 | 0.016 | 0.0625 | 4 |

TABLE 21-continued

| | | | Drug plate | | Final MIC (μg/ml) | | | |
|---|---|---|---|---|---|---|---|---|
| Species[a] | Isolate # | Selecting Compound | (μg/ml) | # CFU recovered | NB-002 | T[b] | I[b] | C[b] |
| T. rubrum | NBD031-b | I | 0.125 | 2 | 4.0 | 0.016 | 0.0625 | 4 |
| T. rubrum | NBD031-c | T | 0.125 | 1 | 4.0 | 0.016 | 0.0313 | 4 |

[a]E. floc. = Epidermophyton floccosum; T. ment. = Trichophyton mentagrophytes; T. rubrum = Trichophyton rubrum;
[b]T = terbinafine; I = itraconazole; C = ciclopirox.

Conclusions: Phenotypic resistance to the tested nanoemulsion (NB-002), ciclopirox (C), terbinafine (T) and itraconazole (I) appeared at $1\text{-}5 \times 10^{-7}$, but none of the isolates were stably resistant. Thus, it appears that no pre-existing subpopulation of cells inherently resistant to the tested nanoemulsion was present, consistent with the uniform fungicidal activity observed in other studies.

Example 8

The Cidal Activity of Nanoemulsions Against Dermatophyte Hyphae and Microconidia The purpose of this example was to determine a possible mechanism of action for the nanoemulsions of the invention against fungal and yeast agents responsible for onychomycosis. In this experiment, the effects of a nanoemulsion according to the invention on the viability and morphology of Trichophyton rubrum were evaluated.

A nanoemulsion was prepared comprising, an aqueous medium, soybean oil, Tween 20® as a nonionic surfactant, ethanol, cetylpyridinium chloride (CPC) as a cationic surfactant, EDTA, and water ("NB-002"). The droplets of the nanoemulsion had an average diameter of ~200 nm. The size and composition allows for selective uptake into hair follicles and pores. The compositions of the nanoemulsion tested in this experiment are shown in Table 22.

TABLE 22

Compositions of NB-002 tested.

| Conc. Nanoemulsion tested (μg CPC/ml)) | Nanoemu. (CPC % w/v) | Soybean oil (%) | Tween 20 (%) | Ethanol (%) | CPC % (ug/mL) | EDTA % (uM) | $H_2O$ (%) |
|---|---|---|---|---|---|---|---|
| 100 | 0.01 | 0.6279 | 0.0592 | 0.0673 | 0.01068 | 0.000745 | 99.23 |
| 16 | 0.0016 | 0.100464 | 0.00947 | 0.01077 | 0.0017088 | 0.000119168 | 100.00 |

Methods

Time-kill experiments. For time-kill experiments and electron micrographs of mechanism of action, microconidia were harvested from 7 day-old cultures of T. rubrum growing on potato dextrose agar using sterile distilled water and adjusted to a concentration of $10^6$ conidia/ml. Part of the conidial suspension was pelleted and resuspended in RPMI 1640 medium and grown for 16-18 hours overnight at room temperature to allow germination of microconidia. After germination, the hyphae were collected by centrifugation and resuspended in distilled water. After mixing with different concentrations of NB-002 or a comparator compound, the rate of killing of microconidia and mycelia was followed for up to 24 hours by plating 0.1 ml of $10^{-1}$, $10^{-2}$ and $10^{-3}$ dilutions onto SDA. Colony-forming units were counted after four days of incubation at 35° C. Control experiments determined that samples containing NB-002 had to be diluted 1:100 to remove residual activity (data not shown).

Scanning electron microscopy: Fungal hyphae and spores were harvested from 7 day-old cultures of T. rubrum growing on potato dextrose agar using sterile distilled water and the fungal stock was adjusted to a concentration of $10^6$ conidia/ml. Samples (450 μl or 450 μl of a $10^{-1}$-dilution) from different time points during a NB-002 time-kill study where 50× (100 μg CPC/ml) and 250×MIC (500 μg CPC/ml) were mixed with 113 μl of fixative (10% aqueous solution of glutaraldehyde in Sorenson's buffer, pH 7.4). Mixtures were vortexed and placed at 4° C. for at least 18 hours. The procedure for fixing and staining the samples for scanning electron microscopy comprised: (1) fixing the samples in 2.5% Glutaraldehyde in Sorenson's buffer, pH 7.4; (2) the samples were rinsed twice for 15 minutes each in 0.1 M. Sorensen's buffer; (3) the samples were fixed in 1.0% $OsO_4$ in Sorenson's buffer; (4) the samples were rinsed twice for 5 minutes each in 0.1 M. Sorensen's buffer; (5) samples were dehydrated for 15 minutes each in each of the following: 30% EtOH, 50% EtOH, 70% EtOH, 90% EtOH, 100% EtOH, 100% EtOH; (6) samples were immersed in four, 15 minute changes of hexamethyldisilazane (HMDS); (7) samples were removed following the fourth change of HMDS and replaced with just enough HMDS to cover tissue. (8) samples were mounted on SEM stubs, using the mixture of Colloidal graphite and duco cement; (9) samples were placed in a vacuum desiccator overnight; (10) samples were sputter-coated with gold using "Polaron" sputter coater; and (11) samples were examined on an "Amray 1910 FE" Scanning Electron Microscope and digitally imaged using Xstream imaging software.

Results

Both the hyphal and microconidial spore forms are rapidly killed by NB-002 (FIGS. 10-12). The kinetics of fungicidal activity of NB-002 and comparator compounds were evaluated against microconidia and mycelia from three isolates of T. rubrum. FIG. 10 shows the reduction in colony counts of representative isolate NBDO31 over 24 hours for either mycelia or microconidia suspended in water (nongrowth conditions) containing either 4×MIC (16 μg/ml) of NB-002 or 16×MIC of itraconazole (16 μg/ml), terbinafine (4 μg/ml) or ciclopirox (16 μg/ml). In two hours, NB-002 reduced colony counts by ≧3 logs in both mycelia and microconidia for NBDO31 and NBDO30; one isolate (NBDO32) required incubation for 4 hours with NB-002 for a 3-log reduction in colony counts (data not shown). None of the other compounds significantly reduced colony counts for either dermatophyte form (hyphae or microconidia spore) at any time point; an exception was a 3-log reduction by ciclopirox (16×MIC or 8 µg/ml) after 8 hours against nongrowing mycelia, but not microconidia, from *T. rubrum* NBDO32 (data not shown).

The mechanism of action of NB-002 on the morphology of *T. rubrum* hyphae and microconidia was assessed by scanning electron microscopy. FIG. 11A shows a scanning electron micrograph of *T. rubrum* NBDO30 mycelia (hyphae) without NB-002 treatment, and FIG. 11B shows scanning electron microscopy after NB-002 treatment (100 µg/ml) for 1 hour at room temperature (2,000× magnification). Note the bleb formations along the hyphal cell wall; FIG. 12 shows a higher magnification of the bleb formation after NB-002 treatment. FIGS. 11C and 11D are microconidia spores (arrows) before and after NB-002 treatment, respectively. The spores appear to be broken, empty shells after 1 hour of NB-002 treatment. Thus, despite the differences in cell wall structure, NB-002 effectively kills both microconidia spores and mycelia.

Nanoemulsions according to the invention are rapidly fungicidal to both conidia spores and mycelia of *T. rubrum*. NB-002 does not require the fungi to be actively growing and appears to "kill on contact" by interacting with the fungal cell surface, morphologically causing blebs and loss of viability. This mechanism of action is contrasted with that for conventional small molecule drugs used to treat onychomycosis, such as terbinafine and itraconazole. These drugs have no activity on either type of fungal preparation (FIG. 10). Their mechanism of action is to interfere with sterol biosynthesis and likely require growing cells to inhibit growth. Ciclopirox, whose mechanism appears mixed, had no activity against the conidial form.

Example 9

Delivery of Nanoemulsion into Epidermis and Dermis

The purpose of this example was to compare the delivery of a nanoemulsion according to the invention into the dermis and epidermis, and compare the delivery with a control composition comprising the cationic surfactant present in the tested nanoemulsion.

A NB-002 nanoemulsion (% w/w) was prepared comprising 19.2% soybean oil, 1.5% Tween 20® as a nonionic surfactant, 2.4% ethanol, 0.3% cetylpyridinium chloride (CPC) as a cationic surfactant, 0.0024% EDTA, and 76.6% water ("NB-002"). A control composition comprised 0.3% w/v aqueous cetylpyridinium chloride (CPC).

The nanoemulsion (NB-002) and the control CPC composition were both topically applied to human cadaver skin. After 24 hours, the quantity of CPC present in the epidermis and dermis was measured for the control CPC composition and the NB-002 composition.

Figure 13A:
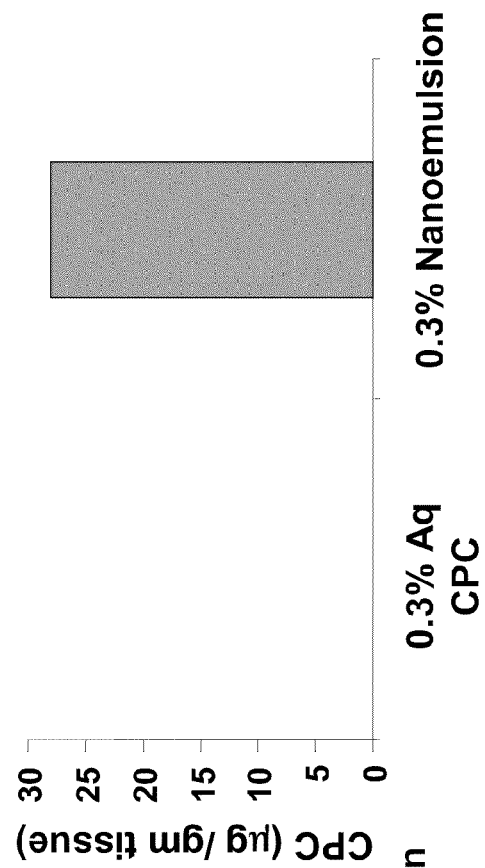
Figure 13B:
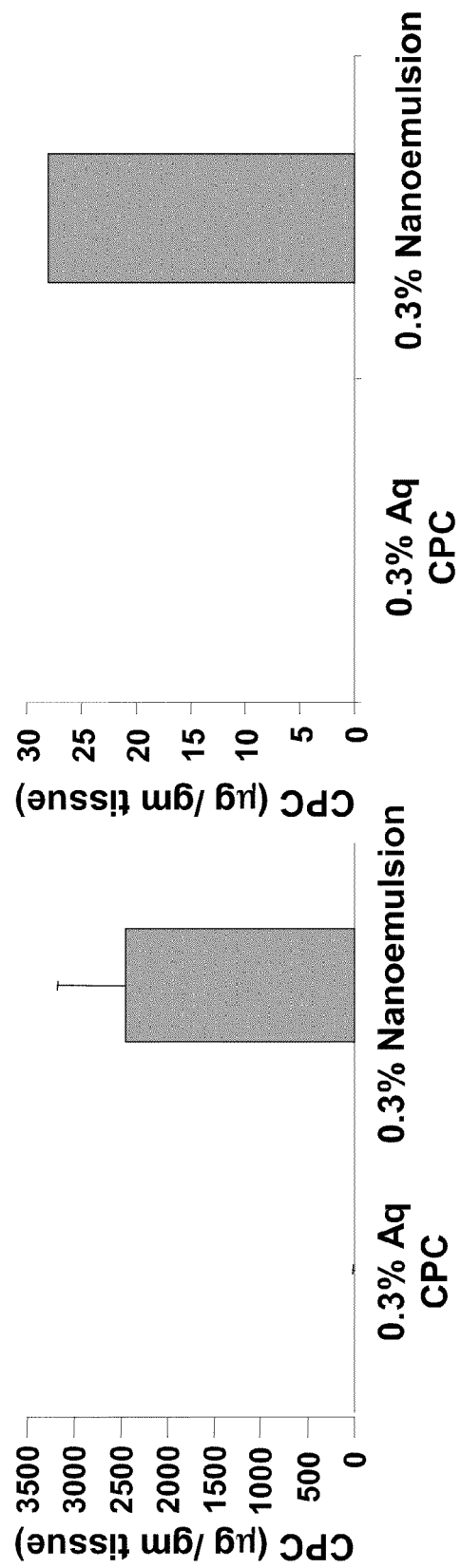

The results, as shown in FIGS. 13A and 13B, demonstrate that the control CPC composition had virtually no absorption into the epidermis (FIG. 13A) or dermis (FIG. 13B). In contrast, the nanoemulsion exhibited excellent absorption into the epidermis (FIG. 13A) and dermis (FIG. 13B), with about 2500 µg/gm tissue of CPC measured in the epidermis, and about 29 µg/mg tissue CPC measured in the dermis 24 hours after application. These results demonstrate that the nanoemulsion structure is critical for effective absorption in the dermis and epidermis.

Example 10

Delivery of Different Nanoemulsion Concentrations in Pig Epidermis and Dermis

The purpose of this example was to evaluate the absorption into the epidermis and dermis of nanoemulsions having different concentrations of a cationic surfactant. Five different nanoemulsions were prepared. All of the nanoemulsions comprised, soybean oil, Tween 20® as a nonionic surfactant, ethanol, cetylpyridinium chloride (CPC) as a cationic surfactant, EDTA, and water ("NB-002"). The compositions (% w/w) are summarized in the table below.

TABLE 23

| Composition | Water % | Soybean oil % | Tween 20% | Ethanol % | CPC % | EDTA % |
|---|---|---|---|---|---|---|
| 0.1% | 92.2 | 6.4 | 0.5 | 0.8 | 0.107 | 0.0075 |
| 0.2% | 84.4 | 12.8 | 1 | 1.6 | 0.214 | 0.0016 |
| 0.3% | 76.6 | 19.2 | 1.5 | 2.4 | 0.32 | 0.0022 |
| 0.4% | 68.8 | 25.6 | 2 | 3.2 | 0.428 | 0.032 |
| 0.5% | 61 | 32 | 2.5 | 4 | 0.534 | 0.0373 |

Absorption into the epidermis (FIG. 14A) and dermis (FIG. 14B) were measured after a single application and after three applications onto pig skin. The results, as shown in FIG. 14A, demonstrate that all of the nanoemulsions exhibited absorption into the epidermis after a single application. Similarly, the results, as shown in FIG. 14B, demonstrate that all of the nanoemulsions exhibited absorption into the dermis after a single application. Moreover, all of the formulations exhibited absorption into the epidermis following three applications (FIG. 14B). However, after three applications, the formulation comprising 0.1% w/v CPC did not exhibit absorption into the dermis.

Example 11

The Delivery of Terbinafine into Pig Epidermis and Dermis Using Nanoemulsions

The purpose of this example was to evaluate the in vitro absorption into the epidermis and dermis of nanoemulsions according to the invention further comprising the active agent terbinafine hydrochloride (TBHC) as compared to that of the conventional TBHC formulation represented by Lamisil® cream. Pig skin was used as an animal model.

11.1: In Vitro Skin Model

The in vitro skin model has proven to be a valuable tool for the study of percutaneous absorption of topically applied compounds (Franz, T J, "Percutaneous absorption: on the relevance of in vitro data," *J. Invest. Dermatol.*, 64:190-195 (1975)). The model uses excised skin mounted in specially designed diffusion chambers that allow the skin to be maintained at a temperature and humidity that match typical in vivo conditions. A finite dose of formulation is applied to the epidermis, outer surface of the skin and compound absorption is measured by monitoring its rate of appearance in the receptor solution bathing the dermal surface of the skin. The method has historic precedent for accurately predicting in vivo percutaneous absorption kinetics (Franz T J, "The finite dose technique as a valid in vitro model for the study of percutaneous absorption in man," *Skin: Drug Application and Evaluation of Environmental Hazards, Current Problems in Dermatology*, vol. 7, pp 58-68, Simon et al. (Eds) (Basel, Switzerland, S. Karger, 1978)).

11.2: Terbinafine Hydrochloride

Terbinafine hydrochloride is a white, fine crystalline, powder that is freely soluble in methanol and dichloromethane, soluble in ethanol, and slightly soluble in water. Oral tablets containing 250 mg TBHC are often prescribed for the treatment of onychomycosis of the toenail or fingernail due to the dermatophyte *Tinea unguium*. As a 1% cream or powder it is used for superficial skin infections such as jock itch (*Tinea cruris*), athlete's foot (*Tinea pedis*) and other types of ringworm (*Tinea coporis*). The chemical structure and physical chemical properties are given below.

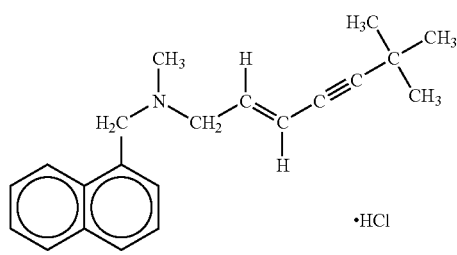

11.3 Nanoemulsions Used in the Study

Two different nanoemulsions were prepared and their respective compositions are shown in Table 24. The ability of these formulations to deliver terbinafine (TBHC) to the epidermis and dermis was compared to Lamisil® cream comprised of 1% TBHC. Nanoemulsions used in this study are oil-in-water (o/w) emulsions with mean droplet diameters of ~200 nm. Cetylpyridinium chloride (CPC), a cationic surfactant in the nanoemulsion, was used as an additional marker agent of delivery. CPC resides at the interface between the oil and water phases. The hydrophobic tail of the surfactant distributes in the oil core and its polar head group resides in the water phase.

TABLE 24

Compositions of the Nanoemulsions.
The percentages are wt/wt, unless otherwise noted.

| Formulation | Soybean oil % | Tween 20 % | Ethanol % | CPC % | TBHC % (wt/v) | EDTA % | Water % |
|---|---|---|---|---|---|---|---|
| 1% TBHC/0.3% nanoemulsion a | 18.837 | 1.776 | 12.037 | 0.320 | 1.0 | 0.022 | 66.01 |
| 1% TBHC/0.3% nanoemulsion b | 18.837 | 1.776 | 22.037 | 0.320 | 1.0 | 0.022 | 56.01 |

11.4 Pig Skin

Full thickness, back skin (~1000 μm thickness) from 2 month old male swine was used in permeation studies and obtained from Sinclair Research Center, Inc, Auxvasse, Mo. The subcutaneous fat was removed using a scalpel and the skin was stored in aluminum foil pouches at −70° C. until use. At time of use, the skin was thawed by placing the sealed pouch in 30° C. water for approximately five minutes. Thawed skin was removed from the pouch and cut into circular discs (30 mm diameter) to fit between the donor and receiver sides of the permeation chambers.

11.5 Franz Diffusion Cell Methodology: Conditions, Parameters, Procedure

Percutaneous absorption was measured using the in vitro cadaver skin finite dose technique. The receptor compartment was filled with distilled water, pH 7 and the donor compartment was left open to ambient laboratory conditions. The receptor volume of each cell was 7.7 ml per apparatus with a magnetic stirring bar. The receptor compartment was maintained at 37° C. with the water bath and magnetic stirring. The surface temperature of the skin was appropriately 32° C. as determined by an IR surface temperature probe.

The skin was equilibrated for a period of 30 minutes before applying the 113 μL dose. The nanoemulsion formulations were applied onto the epidermal surface of the donor chamber of the diffusion cells using a positive displacement pipette. The exposed dosing epidermal surface area was 1.13 cm$^2$. A second dose was applied 8 hours later. The Lamisil $^{AT}$Cream was also applied using a positive displacement pipette and then rubbed into the skin for 10 seconds. The cream was also applied 8 hours later. Twenty four hours after application of the first dose, the surface of the skin was rinsed with 1 ml of 70% ethanol/water solution and then cleaned with a 70% ethanol soaked cotton swab, four times. Following alcohol swabbing, the donor cap was removed and the skin was removed from the apparatus. The epidermis was removed from the dermis via a scraping method and placed in a tarred scintillation vial. A punch biopsy was taken through the dermis and placed in a tarred scintillation vial. Weights of dermis and epidermis were recorded. The excess skin portion was placed in scintillation vial with the surface swabs.

11.6 Sampling (Receptor Sampling, Epidermis, Dermis, Surface Swabs/Extra Skin)

Twenty-four hours after application of the first dose, the surface of the dosing area was rinsed with 1 mL of 70% ethanol/water solution and swabbed independently several times with cotton swabs soaked 70% ethanol/water solution to remove all residual formulation from the skin surface. All the surface swabs were assayed for CPC content.

Two mL of the receptor solution was also sampled at 24 hours from the receptor of each cell and filtered through a 0.45 μm PTFE (25 mm) membrane syringe filter and assayed independently for TBHC and CPC.

Skin samples were collected as described above; weights of the epidermal and dermal tissue were recorded. The epidermal and dermal tissues were extracted with 3 mL of 200 proof, absolute ethanol, sonicated for 30 minutes, filtered through a 25 mm, 0.45 µm PTFE membrane syringe filter and assayed for TBHC and CPC independently. Lamisil samples were also assayed for CPC.

11.7 Epidermal and Dermal Calculations

A standard concentration of TBHC or CPC was generated and used to determine the concentration of TBHC or CPC in the dosing area. The levels of CPC or TBHC in each skin area are represented as: 1) amount per wet tissue weight (µg/grams)±the standard deviation; 2) amount per surface area (µg/cm$^2$)±the standard deviation; 3) the % of the applied dose±the standard deviation.

11.8 CPC Levels following Topical Administration of 1% TBHC/0.3% Nanoemulsion Formulations The results of CPC permeation studies for 1% TBHC/0.3% nanoemulsion formulations are shown in Table 25.

TABLE 25

Percutaneous absorption of CPC formulations into pig skin over 24 hours from BID dosing. Epidermal and dermal summary (amount CPC (µg) per surface area (cm$^2$): mean of replicates ± SD; amount CPC (µg) per weight tissue (g): mean of replicates ± SD); % of the total applied dose).

| | 1% TBHC/0.3% nanoemulsion a | | | 1% TBHC/0.3% nanoemulsion b | | |
|---|---|---|---|---|---|---|
| | µg/cm$^2$ | µg/gram tissue | % applied dose | µg/cm$^2$ | µg/g | % applied dose |
| Epidermis | 48.8 ± 16.3 | 941.2 ± 437.3 | 8.14 ± 2.70 | 58.8 ± 12.9 | 1236.8 ± 242.7 | 9.80 ± 2.15 |
| Dermis | 9.1 ± 4.3 | 37.1 ± 17.1 | 1.52 ± 0.71 | 17.3 ± 5.7 | 70.6 ± 23.5 | 2.88 ± 0.95 |
| Receptor | 0 | 0 | 0 | 0 | 0 | 0 |
| Mass Balance | | 97.29 ± 2.22% | | | 98.86 ± 1.14% | |

The delivery of the CPC marker into the epidermis with the 1% TBHC/0.3% nanoemulsion a and 0.3% nanoemulsion b were comparable. Ethanol concentration in the nanoemulsion formulation appears to enhance delivery of CPC into dermal tissues. 1% TBHC/0.3% nanoemulsion b formulation had 2 fold higher levels of CPC (37.1 µg/gram compared to 70.6 µg/gram) than the 1% TBHC/0.3% nanoemulsion a formulation. This finding is consistent with that seen with TBHC levels in the dermis.

The amount of CPC found in the receptor compartment at 24 hours was below the level of detection (5 ng/ml) for all the formulations.

11.9 TBHC Absorption Results

The results of TBHC permeation studies for Lamisil$^{AT}$, 1% TBHC/0.3% nanoemulsion a and 1% TBHC/0.3% nanoemulsion b are shown in Table 26 and FIGS. 15 and 16.

TABLE 26

Percutaneous absorption of TBHC formulations into pig skin over 24 hours from BID dosing. Epidermal and dermal pig skin summary (amount TBHC (µg) per surface area (cm$^2$): mean of replicates ± SD; amount TBHC (µg) per weight tissue (g): mean of replicates ± SD); % of the total applied dose).

| | Lamisil$^{AT}$ Cream | | | 1% TBHC/0.3% Nanoemulsion a | | | 1% TBHC/0.3% Nanoemulsion b | | |
|---|---|---|---|---|---|---|---|---|---|
| | µg/cm$^2$ | µg/gram tissue | % applied dose | µg/cm$^2$ | µg/gram tissue | % applied dose | µg/cm$^2$ | µg/g | % applied dose |
| Epidermis | 4.3 ± 1.0 | 108.8 ± 37.9 | 0.21 ± 0.05 | 104.6 ± 36.0 | 2028.2 ± 919.6 | 5.23 ± 1.80 | 78.9 ± 31.2 | 1631.3 ± 596.9 | 3.94 ± 1.56 |
| Dermis | 2.0 ± 0.9 | 9.3 ± 3.5 | 0.10 ± 0.04 | 24.9 ± 7.1 | 102.6 ± 29.1 | 1.24 ± 0.36 | 47.2 ± 5.8 | 192.1 ± 16.7 | 2.36 ± 0.29 |
| Receptor | 0 | 0 | 0 | 0 | 0 | 0 | 0 | 0 | 0 |

Lamisil® cream delivered ~12× times more TBHC into the epidermis as compared to the dermis. 1% TBHC/0.3% nanoemulsion a delivered ~20× times more TBHC into the epidermis as compared to the dermis. 1% TBHC/0.3% nanoemulsion b delivered ~8.5× times more TBHC into the epidermis as compared to the dermis.

The levels of TBHC in the epidermis were 18.6 and 15.1 times higher for 1% TBHC/0.3% nanoemulsion a and 1% TBHC/0.3% nanoemulsion b, respectively, as compared to the Lamisil$^{AT}$ Cream formulation. The levels of TBHC in the dermis were 10.9 and 20 times higher for 1% TBHC/0.3% nanoemulsion a and 1% TBHC/0.3% nanoemulsion b, respectively, as compared to the Lamisil$^{AT}$. Cream formulation. This indicates that superior delivery of TBHC into the skin was achieved after a topical application of the novel nanoemulsions containing TBHC. Thus, the nanoemulsions significantly enhanced the TBHC delivery into the epidermis and dermis.

Example 12

In Vitro Permeation Studies for Nanoemulsion Formulations Comprising Miconazole and Lotrimin® Spray Solution Containing Miconazole Nitrate The purpose of this example was to investigate the potential of nanoemulsion formulations to deliver miconazole (MCZ) into swine skin. Commercially available Lotrimin AF® Spray Solution was used as a control. Cetylpyridinium chloride (CPC), a cationic surfactant in the nanoemulsion, was used as an additional marker agent of delivery for the nanoemulsion.

Miconazole is an imidazole antifungal agent commonly applied topically to the skin or mucus membranes to cure fungal infections. It works by inhibiting the synthesis of ergosterol, a critical component of fungal cell membranes. It can also be used against certain species of *Leishmania* protozoa, which are a type of unicellular parasite, as these also contain ergosterol in their cell membranes. In addition to its antifungal and antiparasitic actions, it also has some limited antibacterial properties. Miconazole is mainly used externally for the treatment of athlete's foot, ringworm and jock itch. Internal application is used for oral or vaginal thrush (yeast infection). In addition the oral gel may also be used for the lip disorder angular cheilitis. The chemical structure and physical chemical properties are given below.

Chemical Structure of Miconazole:

TABLE 27

Physical-chemical properties of miconazole.

| | |
|---|---|
| CAS Number | 22916-47-8 |
| Molecular Formula | $C_{18}H_{14}Cl_4N_2O$ |
| Molar Mass | 416.13 g/mol |
| Melting Point | 170.5° C. |
| Log P/pKa | 6.1/6.67 |
| Water Solubility | 0.03% |
| Soybean Solubility | 74 mg/ml |
| Ethanol Solubility | 94 mg/ml |

Experimental 12.1. Test Formulations

Preparation of 2% Miconazole/0.3% Nanoemulsion

The nanoemulsion test formulations comprised a final concentration of 0.3% (0.3% CPC or 3 mg CPC/ml) and 2% miconazole. Miconazole was incorporated into a 1% nanoemulsion (comprising 1% CPC) by first dissolving the miconazole in ethanol until completely solubilized and then mixing with the water. This solution was slowly added, with gentle mixing, to the 1% nanoemulsion to obtain a final product containing 0.3% nanoemulsion with 2% miconazole. No evidence of miconazole precipitation was observed after mixing with the nanoemulsion by visual inspection and microscopy. Miconazole can also be solubilized in the oil phase prior to emulsion formulation. The composition of the miconazole nanoemulsion is listed in Table 28.

TABLE 28

Composition of the Nanoemulsion (MCZ/NB-00X). The percentages are wt/wt, unless otherwise noted.

| Formulation | Lot # | Soybean oil % | Tween 20% | Ethanol % | CPC % | MCZ % (wt/v) | EDTA % | Water % |
|---|---|---|---|---|---|---|---|---|
| 2% MCZ/0.3% NB-00X | 89-59-03 | 18.837 | 1.776 | 12.037 | 0.320 | 2.0 | 0.022 | 66.01 |

Lotrimin AF® Spray Solution contained 2% miconazole nitrate. Inactive ingredients in Lotrimin AF® Spray Solution include denatured alcohol (13% v/v), cocamide DEA, isobutene, propylene glycol and tocopherol (vitamin E).

12.2. Epidermal and Dermal Calculations

The amount of MCZ that permeated into the epidermis, dermis and the receptor compartment (at 24 hours after first dose) was determined by HPLC MS/MS. A standard concentration of MCZ was generated and used to determine the concentration of MCZ in the dosing area. The levels of CPC or MCZ in each skin area are represented as: (1) amount per surface area ($\mu g/cm^2$)±the standard deviation; (2) amount per wet tissue weight ($\mu g/grams$)±the standard deviation; (3) the % of the applied dose±the standard deviation.

Results and Conclusions

The results of MCZ permeation studies for Lotrimin®$_{AF}$ Spray Solution and 2% MCZ/0.3% nanoemulsion are shown in Table 29 and FIGS. 17 and 18.

TABLE 29

Percutaneous absorption of MCZ formulations into swine skin over 24 hours from BID dosing. Epidermal and dermal pig skin summary (amount MCZ ($\mu g$) per surface area ($cm^2$): mean of replicates ± SD; amount MCZ ($\mu g$) per weight tissue (g): mean of replicates ± SD); % of the total applied dose).

| | Lotrimin ®$_{AF}$ Spray Solution | | | 2% MCZ/0.3% NB-00X | | |
|---|---|---|---|---|---|---|
| | MCZ $\mu g/cm^2$ | MCZ $\mu g/gram$ tissue | % applied dose | MCZ $\mu g/cm^2$ | MCZ $\mu g/gram$ tissue | % applied dose |
| Epidermis | 6.54 ± 2.29 | 118.4 ± 16.2 | 0.16 ± 0.05 | 153.8 ± 43.1 | 3543.5 ± 1213.2 | 3.84 ± 1.08 |
| Dermis | 4.6 ± 0.8 | 21.2 ± 4.0 | 0.11 ± 0.02 | 41.6 ± 10.2 | 190.9 ± 43.5 | 1.04 ± 0.25 |
| Receptor | 0 | 0 | 0 | 0 | 0 | 0 |

Commercially available Lotrimin®$_{AF}$ Spray Solution delivered ~5.6× times more MCZ into the epidermis as compared to the dermis. Surprisingly, the nanoemulsion formulation comprising 2% MCZ/0.3% NB-00X delivered ~18.6× times more MCZ into the epidermis as compared to the dermis. Thus, there was a significant increase in the delivery of the MCZ into the epidermis and dermis with the 2% MCZ/0.3% nanoemulsion formulation as compared to the Lotrimin AF®Spray Solution. The levels of MCZ found in the epidermis and dermis after 24 hours were lower for the Lotrimin Spray formulation compared to the 2% MCZ/0.3% nanoemulsion formulation. The levels of MCZ in the epidermis were 30 times higher for 2% MCZ/0.3% nanoemulsion as compared to the Lotrimin AF®Spray Solution. The levels of MCZ in the dermis were 9 times higher for 2% MCZ/0.3% nanoemulsion as compared to the Lotrimin AF® Spray Solution. Thus, there is increased delivery of MCZ into epidermal and dermal tissues using the nanoemulsion formulation as compared to the Lotrimin AF® Spray Solution. The amount of MCZ found in the receptor compartment at 24 hours was below the level of detection (50 ng/ml) for all formulations tested.

Example 13

The Nanoemulsions Diffuse Laterally to Sites of Infection

The purpose of this example was to test whether nanoemulsion droplets can diffuse laterally to areas in the skin not directly underlying the site of application.

In vitro studies were carried out using excised human cadaver skin in a modified Franz diffusion apparatus. The nanoemulsions used in this study were oil-in-water (o/w) emulsions with mean droplet diameters of ~200 nm. The cetylpyridinium chloride (CPC), which is used as a marker for delivery, resides at the interface between the oil and water phases. Part of the surfactant is distributed in the oil core and part resides in the water phase.

The nanoemulsion test formulations comprised either 0.25% NB-002 or 0.5% NB-002. The emulsions were produced by mixing a water-immiscible oil phase with an aqueous phase followed by high energy emulsification to obtain the desired particle size of ~200 nm. The aqueous CPC solution was prepared by simple weighing of the CPC and addition the water until the CPC was dissolved in the water phase. The composition of the nanoemulsions, expressed as w/w % unless otherwise noted, used in this study is given in Table 30 below.

TABLE 30

Compositions of the Nanoemulsions (NB-002) and the aqueous CPC solution (AQ). The percentages are wt/wt, unless otherwise noted.

| Formulation | Soybean oil % | Tween 20 % | Ethanol % | CPC % | EDTA % (mM) | Water % |
|---|---|---|---|---|---|---|
| 0.50% NB002 | 31.4 | 2.96 | 3.37 | 0.53 | 0.037 (1) | 61.70 |
| 0.25% NB002 | 15.7 | 1.48 | 1.68 | 0.27 | 0.0185 (0.5) | 80.85 |
| 0.5% w/v AQ | 0 | 0 | 0 | 0.53 | 0 | 99.5 |

As described in more detail below, 100 $\mu l/cm^2$ of NB-002 nanoemulsions were applied to a 5.27 $cm^2$ concentric surface area of skin enclosed by two concentric glass cylinders. See FIGS. 19 and 20. Due to apparatus design, the only way CPC could be detected in the middle or inner tissues is through permeation of nanoemulsion into the skin underlying the dosing area traversing laterally into the non-dosing areas.

Epidermal and dermal concentrations of CPC in the non-dosing area were 700 and 150 $\mu g/gram$, respectively in the middle area and 200 and 100 $\mu g/gram$ tissue, respectively, in the inner area. See FIGS. 21-25. These data indicate the nanoemulsion traversed laterally up to 11 mm from the dosing area. The levels of nanoemulsion in the middle and inner area tissues were substantially higher than the previously determined concentrations of nanoemulsion that kills fungi in vitro (4 $\mu g/gram$).

13.1 Experimental

Modified Diffusion Cell Methodology

Percutaneous absorption was measured using the in vitro cadaver skin finite dose technique. Cryopreserved, dermatomed (~700 μm) human cadaver abdominal skin was used and stored in aluminum foil pouches at −70° C. until the time of use. At the time of use, the skin was thawed by placing the sealed pouch in 37° C. water for approximately five minutes. The skin was removed from the pouch and then cut into sections to fit on 38 mm permeation well cells. The receptor compartment was filled with distilled water, pH 7 and the donor compartment was left open to ambient laboratory conditions. All cells were mounted in a diffusion apparatus in which the receptor solution maintained at 37° C. by circulating water bath on the outside of the wells. The parameters for the diffusion study are listed in Table 31 and FIG. 19.

TABLE 31

Experimental Parameters

| | |
|---|---|
| Apparatus: | Permeation diffusion wells |
| Number of Cells: | 3-4 for 24 hours |
| Membrane: | Human Cadaver Abdominal Skin |
| Thickness: | ~700 μm |
| Duration: | 24 hours |
| Dosing Surface Area: | Outer dosing area, 5.27 cm$^2$ |
| Non-Dosing Area: | Inner non-dosing area, 0.5 cm$^2$ |
| | Middle non-dosing area, 3.3 cm$^2$ |
| Dose per surface area: | 100 μl/cm$^2$ |
| Concentration: | 0.5% w/v CPC in Aqueous solution |
| | 0.25% NB-002 |
| | 0.5% NB-002 |
| Receptor Solution: | Distilled water, pH 7.0 |
| Receptor Sampling: | 24 hours |
| Assay Method: | HPLC assay for CPC |
| Samples collected: | Surface swabs, Epidermis, Dermis, Receptor Samples |

Two circular glass chambers were glued using cyanoacrylate adhesive (e.g. super glue) was used to attach the chambers onto the skin surface as shown in FIG. 20. FIG. 19 illustrates the dimensions of the surface areas involved in the study. The test formulations were applied to the outer dosing area. The middle and inner areas did not receive a topical application of the test formulations.

The test formulations were applied to the epidermal surface of the donor chamber of the diffusion cells once a day and/or twice a day using a positive displacement pipette.

At 24 hours after the first application, the outer dosing area was swabbed several times with 70% ethanol solution to remove all residual formulation from the skin surface. The surface area of the middle and inner areas were also swabbed. All the surface swabs were assayed for CPC content. The chambers were than removed and the outer dosing area was processed. Briefly, the epidermis was removed from the dermis in the outer dosing area via a scraping technique, placed in a tared vial and weighed. The dermis was than removed from the dosing area be using a scalpel and placed in a tared glass vial and weighed. The middle and inner areas were processed in the same fashion. The epidermal and dermal tissues from the outer, middle and inner areas were extracted with 70% ethanol solution, sonicated for 30 minutes, filtered through a 25 mm, 0.45 μm PTFE membrane syringe filter and assayed.

Results and Conclusions

The results of permeation studies for NB-002 are shown in FIGS. 21-25 and Tables 32 and 33. The levels of CPC found in the various compartments (epidermis, dermis and receptor) were significantly different for the aqueous CPC solution and the NB-002 formulations. The levels of CPC found in the epidermis and dermis after 24 hour duration were lower for the 0.5% w/v aqueous CPC solution as compared to the 0.25% and 0.5% NB-002. The amount of CPC found in the receptor compartment at 24 hours was below the level of detection (5 ng/ml) for all the formulations. More CPC was found in the epidermis and dermis from the 0.25% NB-002 formulation after twice daily application (applied t=0 and 8 hours later) as compared to the 0.5% NB-002 applied once.

TABLE 32

Epidermal Human cadaver skin summary (amount CPC (μg) per weight tissue (g): mean of replicates ± SD). Percutaneous absorption of CPC formulations through human cadaver skin over 24 hours from a single or two dose topical applications.

| Parameter | 0.5% w/v Aqueous CPC, QD (μg/g) | 0.5% NB-001, QD (μg/g) | 0.25% NB-002, BID (μg/g) |
|---|---|---|---|
| Outer Dosing Area | 82.2 ± 58.6 | 690.5 ± 321.0 | 1148.0 ± 317 |
| Middle Area | 12.3 ± 10.6 | 85.4 ± 29.0 | 693 ± 11 |
| Inner Area | 0 | 8.32 ± 9.3 | 196 ± 68 |
| Receptor | 0 | 0 | 0 |
| Total Absorption (Epidermis, Dermis) | 94 | 784 | 2037 |

TABLE 33

Dermal Human cadaver skin summary (amount CPC (μg) per weight tissue (g): mean of replicates ± SD). Percutaneous absorption of CPC formulations through human cadaver skin at 24 hours from a single topical or two topical applications.

| Parameter | 0.5% w/v Aqueous CPC, QD (μg/g) | 0.5% NB-001, QD (μg/g) | 0.25% NB-002, BID (μg/g) |
|---|---|---|---|
| Outer Dosing Area | 4.5 ± 1.1 | 26.1 ± 14 | 140 ± 110 |
| Middle Area | 1.7 ± 1.2 | 10 ± 7.4 | 121 ± 74 |
| Inner Area | 0 | 1.1 ± 0.3 | 107 ± 78 |
| Receptor Compartment | 0 | 0 | 0 |
| Total Absorption (Epidermis, Dermis) | 6.2 | 37 | 368 |

These results confirm that the nanoemulsion diffuses laterally under the stratum corneum to tissues over a centimeter away from the site of application. This suggests that NB-002 can diffuse under human nails from adjacent skin sites to kill the fungus that causes onychomycosis.

Example 14

Lateral Diffusion of Terbinafine in Human Cadaver Skin

The purpose of this example was to determine whether an active agent incorporated into a nanoemulsion formulation, such as terbinafine hydrochloride (TBHC), can diffuse laterally into human cadaver skin.

1% TBHC was incorporated into the nanoemulsion formulation. The oil-in-water nanoemulsions used in this study have a mean droplet diameters of approximately ~200 nm.

CPC resides at the interface between the oil and water phases. Lamisil® cream containing 1% TBHC was used as a control.

In vitro studies were carried out using excised human cadaver skin in a modified Franz diffusion apparatus. 1% TBHC/0.3% CPC NB-00Xb at 100 µL/cm² was applied to a 5.27 cm² concentric surface area of skin enclosed by two concentric glass cylinders. Twenty-four hours post application, residual nanoemulsion was removed by swabbing the dosing area. The epidermis and dermis of the dosing area was separated, weighed and assayed for CPC and TBHC. An 8 mm punch biopsy of the inner non-dosing area (inner area) and middle non-dosing area (middle area) were processed in similar fashion. Quantification of CPC and TBHC was performed by high pressure liquid chromatography (HPLC) with independent methods. The only way CPC or TBHC could be detected in the middle or inner tissues is through permeation of nanoemulsion into the skin underlying the dosing area followed by lateral diffusion into the non-dosing areas.

14.1 Experimental

Test Formulations
Preparation of 1% TBHC/0.3% NB-00Xb
The nanoemulsion formulation of this study comprised: 0.3% CPC (0.3% NB-001 or 3 mg CPC/ml) and 1% TBHC. TBHC was incorporated into 1% NB-00Xb (containing 1% CPC) by first dissolving the TBHC in ethanol and then mixing with water. This solution was slowly added, with gentle mixing, to the 1% nanoemulsion to obtain a final product comprising 0.3% nanoemulsion with 1% TBHC. The final formulation comprised 22% ethanol and 57% water. The compositions of the TBHC nanoemulsion is shown in Table 34.

TABLE 34

Composition of the nanoemulsion. The percentages are wt/wt, unless otherwise noted.

| Formulation | Lot # | Soybean oil (%) | Tween 20 (%) | Ethanol (%) | CPC (% w/v) | TBHC (% w/v) | EDTA (%) | Water (%) |
|---|---|---|---|---|---|---|---|---|
| 1% TBHC/0.3% NB-00Xb | 89-59-02 | 18.837 | 1.776 | 22.037 | 0.320 | 1.0 | 0.022 | 56.01 |

Lamisil® is commercially available and contains 1% TBHC. The test formulations were applied to the epidermal surface of the donor chamber of the diffusion cells using a positive displacement pipette. For single dosing, 527 µL was applied (e.g. QD). For multiple dosing (e.g. BID), 527 µL was applied 8 hours after the initial dosing. The exposed dosing epidermal surface area was 5.27 cm².

Human Cadaver Skin

Human cadaver back abdominal from a 75-year-old Caucasian male donor obtained from Life Legacy tissue bank was used in this study. The skin was cut into circular discs having 38 mm in diameter and the weights of the epidermis and dermis were recorded for each cell and from each dosing area and each non-dosing area before tissue extraction. The 1% TBHC/0.3% NB-00Xb formulation and Lamisil® were applied twice at 0 and 8 hours after the start of the study.

Modified Diffusion Apparatus

This experimental design was similar to that presented in Example 13.

The parameters for the diffusion study are listed in Table 35.

TABLE 35

Parameters for the Lateral Diffusion Methodology.

| Apparatus | Modified diffusion cell apparatus |
|---|---|
| Membrane | Human Cadaver Skin (75 yr old Male), Abdominal Skin: Lot 08-01034) |
| Duration | 24 hours |
| Dosing Surface Area | Outer dosing area, 5.27 cm² |
| Non-dosing Surface Area | Inner non-dosing area, 0.5 cm² Middle non-dosing area, 3.3 cm² |
| Dose | 113 µL |
| Dose per Surface Area | 100 µL/cm² |
| Concentration | Lamisil ® (Lot# 10047765) 1% TBHC/0.3% NB-00Xb (Lot #89-59-02) |
| Dosing Frequency | QD: Once (0 hr); BID: Twice (0 and 8 hr) |
| Receptor Sampling | 24 hours |
| Surface Wash | 1 ml of 70% Ethanol solution and 4 surface swabs in 70% ethanol solution 3-5 times with cotton swabs dipped in ethanol |
| Assay Method | HPLC |

Epidermal and Dermal Calculations

The amount of TBHC and CPC that permeated into the epidermis, dermis and the receptor compartment (at 24 hours after first dose) was determined by HPLC. A standard concentration of TBHC or CPC was generated and used to determine the concentration of TBHC or CPC in the dosing area. The levels of CPC or TBHC in each skin area are represented as: 1) amount per wet tissue weight (µg/grams)±the standard deviation; 2) amount per surface area (µg/cm²)±the standard deviation.

14.2 Results

TBHC Levels following Topical Administration

The results of permeation studies of Lamisil® and 1% TBHC/0.3% NB-00b for epidermal human cadaver skin and for dermal human cadaver skin are shown in Tables 36 and 37, respectively. The levels of TBHC delivered from 1% TBHC/0.3% NB-00Xb found in the various compartments (epidermis and dermis) were significantly different from levels of TBHC delivered from Lamisil® cream. The levels of TBHC found in the epidermis and dermis after 24 hour duration were lower for the Lamisil® cream as compared to the 1% TBHC/0.3% NB-00Xb formulation.

The levels of TBHC found in the outer, middle and inner epidermis of the samples treated by the NB-00Xb formulations containing TBHC were 14, 35 and 293 times higher (µg/g tissue levels), respectively, relative to the same areas (outer, middle inner) of the samples treated by the Lamisil® cream. The levels of TBHC found in the outer, middle and inner dermis of the samples treated by the 1% TBHC/0.3% NB-00Xb formulation were 27, 28 and 115 times higher (µg/g tissue levels), respectively, relative to the same areas (outer, middle, inner) of the samples treated by the Lamisil® cream.

Also, the amount of TBHC found in the surface swabs of the middle and inner surface areas at 24 hours was below detection level of 5 µg/ml for all the formulations, indicating no leakage of the test article from the dosing area to non-dosing areas.

TABLE 36

Epidermal human cadaver skin summary: percutaneous absorption of TBHC formulations through human cadaver skin over 24 hours from BID topical dosing (0 and 8 hrs).

| Parameter | Lamisil ® Cream, BID | | 1% TBHC/0.3% CPC NB-00Xb, BID | |
|---|---|---|---|---|
| | TBHC (µg/cm$^2$) | TBHC µg/g wet tissue | TBHC (µg/cm$^2$) | TBHC (µg/g wet tissue) |
| Outer Dosing Area | 2.05 ± 0.92 | 193.8 ± 77.0 | 35.23 ± 15.4 | 2788.0 ± 810.7 |
| Middle Area | 0.21 ± 0.23 | 48.2 ± 49.8 | 9.87 ± 5.69 | 1686.3 ± 1175.9 |
| Inner Area | 0.013 ± 0.023 | 2.12 ± 3.73 | 4.30 ± 2.10 | 621.0 ± 330.3 |
| Number of Replica | 3 | 3 | 4 | 4 |

TABLE 37

Dermal human cadaver skin summary: percutaneous absorption of TBHC formulations through human cadaver skin over 24 hours from BID topical dosing (0 and 8 hrs).

| Parameter | Lamisil ® Cream, BID | | 0.3% CPC/1% TBHC in NB-00Xb, BID | |
|---|---|---|---|---|
| | TBHC µg/cm$^2$) | TBHC µg/g wet tissue | TBHC (µg/cm$^2$) | TBHC (µg/g wet tissue) |
| Outer Dosing Area | 0.59 ± 0.35 | 6.8 ± 6.1 | 18.9 ± 4.1 | 182.1 ± 46.0 |
| Middle Area | 0.16 ± 0.14 | 3.59 ± 3.93 | 6.95 ± 6.59 | 96.8 ± 53.8 |
| Inner Area | 0.01 ± 0.02 | 2.15 ± 3.73 | 2.22 ± 1.81 | 248.3 ± 242.2 |
| Number of Replica | 3 | 3 | 4 | 4 |

14.3 Conclusions

The lateral diffusion data of nanoemulsions comprising terbinafine hydrochloride indicate that delivery of TBHC by incorporation into the nanoemulsion resulted in lateral diffusion of the second active agent to distances up to 11 mm away from the dosing area. Therefore, the nanoemulsion compositions comprising an additional active agent capable of diffusing under human nails from adjacent skin sites can be delivered to adjacent sites (e.g., under the nail plate) and used to kill fungi that causes onychomycosis.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. A method of killing a fungal, yeast, or mold agent to treat a fungal, yeast, or mold infection, or a combination thereof, in a human subject in need thereof comprising administering topically or intradermally to the human subject a nanoemulsion, wherein:
   (a) the nanoemulsion comprises droplets have an average diameter of less than about 400 nm;
   (b) the nanoemulsion droplets comprise:
       (i) an aqueous phase,
       (ii) soybean oil in an amount of about 1% to about 60%,
       (iii) at least one surfactant in an amount of about 0.001% to about 10%, wherein the surfactant is a polysorbate, cetylpyridinium chloride (CPC), or a combination thereof, and
   (iv) ethanol in an amount of about 0.1% to about 10%, organic solvent is an alcohol; and
   (c) the fungal, yeast, or mold agent is selected from the group consisting of (i) *Trichophyton* species selected from the group consisting of *T. ajelloi, T. concentricum, T. equinum, T. erinacei, T. flavescens, T. gloriae, T. interdigitale, T. megnini, T. phaseoliforme, T. schoenleini, T. simii, T. soudanense, T. terrestre, T. tonsurans, T. vanbreuseghemii, T. verrucosum, T. violaceum,* and *T. yaoundei*, (ii) *Candida* species selected from the group consisting of *C. parapsiliosis, C. krusei, C. tropicalis, C. glabrata, C. parapsilosis, C. lusitaniae, C. kefvr, C. guilliermondii,* and *C. dubliniensis*, (iii) *Microsporum* species selected from the group consisting of *M. audouini, M. gallinae, M. ferrugineum, M. distortum, M nanum, M. cookie,* and *M. vanbreuseghemii*, (iv) *Epicoccum nigrum*, (v) *Aspergillus* species selected from the group consisting of *A. sydowii, A. terreus, A. niger, A. fumigatus, A. flavus, A. clavatus, A. glaucus* group, *A. nidulans, A. oryzae, A. ustus,* and *A. versicolor*, (vi) *Paecilomyces* species selected from the group consisting of *P. lilacinus* and *P. variotii*, (vii) *Fusarium* species selected from the group consisting of *F. oxysporum, F. solani,* and *F. semitectum*, (viii) *Acremonium* species, (ix) *Chaetomium* species selected from the group consisting of *C. atrobrunneum C. funicola C. globosum* and *C. strumarium* (x) *Phoma* species, (xi) *Scopulariopsis* species selected from the group consisting of *S. brevicaulis, S. candida, S. koningii, S. acremonium, S. flava, S. cinerea, S. trigonospora, S. brumptii, S. chartarum, S. fusca,* and *S. asperula*, (xii) *Scytalidium* species selected from the group consisting of *S. dimidiatum, S. hyalinum, S. infestans, S, japonicum,* and *S. lignicola*, (xiii) *Alternaria* species selected from the group consisting of *A. alternate, A. chartarum, A. dianthicola, A. geophilia, A. infectoria, A. stemphyloides,* and *A. teunissima*, (xiv) *Epicoccum* species, (xv) *Curvularia* species selected from the group consisting of *C. brachyspora, C. clavata,*

*C. geniculata, C. lunata, C. pallescens, C. senegalensis*, and *C. verruculosa*, and (xvi) *Tinea* species selected from *Tinea pedis, Tinea unguium, Tinea corporis, Tinea cruris, Tinea capitis, Tinea manuum, Tinea faciale, Tinea versicolor*, and *Tinea barbae*.

2. The method of claim 1, wherein:
  (a) the fungal, yeast, or mold infection is selected from the group consisting of a *tinea* infection, dermatophytoses, and dermatophytoma;
  (b) the fungal, yeast, or mold infection is selected from the group consisting of *Tinea pedis, Tinea unguium, Tinea corporis, Tinea cruris, Tinea capitis, Tinea manuum, Tinea faciale, Tinea versicolor*, and *Tinea barbae*; or
  (c) any combination thereof.

3. The method of claim 1, wherein the nanoemulsion droplets:
  (a) have an average diameter selected from the group consisting of less than about 350 nm, less than about 300 nm, less than about 250 nm, less than about 200 nm, less than about 150 nm, less than about 100 nm, greater than about 50 nm, greater than about 70 nm, greater than about 125 nm, and any combination thereof;
  (b) permeate into the epidermis and dermis via the follicular route using skin pores and hair follicles;
  (c) diffuse through the skin, skin pores, nail, scalp, hair follicles, damaged skin, diseased skin, lateral or proximal folds, nail, hyponichium, or any combination thereof;
  (d) enter the epidermis, dermis, or a combination thereof;
  (e) bind to the fungal cell surface resulting in death, growth inhibition, a loss of pathogenicity, or any combination thereof;
  (f) kill or inhibit the growth of conidia, hyphae, haploid yeast, diploid yeast, or any combination thereof; or
  (g) any combination thereof.

4. The method of claim 1, wherein the topical application is to any superficial skin structure, hair, hair shaft, hair follicle, eye, or any combination thereof.

5. The method of claim 1, wherein the nanoemulsion droplets comprise:
  (a) an aqueous phase;
  (b) about 1% to about 60% soybean oil;
  (c) about 0.1% to about 10% ethanol;
  (d) a polysorbate present in an amount of about 0.1% to about 10%;
  (e) cetylpyridinium chloride present in an amount of about 0.01% to about 2%; and
  (f) about 0.0005% to about 1.0% of a chelating agent which is EDTA.

6. The method of claim 1, wherein the nanoemulsion:
  (a) is fungistatic against the fungal, yeast, or mold agent;
  (b) is fungicidal against the fungal, yeast, or mold agent;
  (c) is therapeutically effective against the fungal, yeast, or mold agent;
  (d) is fungicidal or fungistatic and is effective against fungal conidia and hyphae or mycelia or yeast haploid or diploid cells;
  (e) provides a mycological remedy for the condition to be treated;
  (f) provides an improved rate of mycological remedy as compared to that provided by a conventional non-nanoemulsion topical antifungal treatment;
  (g) is not systemically toxic to the human subject; or
  (h) any combination thereof.

7. The method of claim 1, wherein:
  (a) the nanoemulsion has a narrow distribution of MIC (minimum inhibitory concentration) and MFC (minimum fungicidal concentrations) values;
  (b) the MIC and MFC for the nanoemulsion differ by less than or equal to four-fold, meaning that the nanoemulsion is fungicidal;
  (c) the MIC and MFC for the nanoemulsion differ by greater than four-fold, meaning that the nanoemulsion is fungistatic; or
  (d) any combination thereof.

8. The method of claim 1, wherein the fungal, yeast, or mold agent:
  (a) is *Trichophyton* spp, and the MIC ranges from about 0.25 to about 25 ps CPC/ml;
  (b) is *Trichophyton* spp, and the MFC ranges from about 0.25 to about 100 μg CPC/ml;
  (c) is *Candida* spp., and the MIC ranges from about 0.25 to about 32 μg CPC/ml;
  (d) is *Candida* spp, and the MFC is 0.25 to about 128 μg CPC/ml;
  (e) is *Aspergillus* spp, and the MIC ranges from about 0.25 to about 25 μg CPC/ml;
  (f) is *Aspergillus* spp, and the MFC ranges from about 0.25 to about 100 μg CPC/ml;
  (g) is *Paecilomyces* spp, and the MIC ranges from about 0.25 to about 25 μg CPC/ml;
  (h) is *Paecilomyces* spp, and the MFC ranges from about 0.25 to about 100 μg CPC/ml;
  (i) is *Acremonium* spp, and the MIC ranges from about 0.25 to about 25 μg CPC/ml;
  (j) is *Acremonium* spp, and the MFC ranges from about 0.25 to about 100 μg CPC/ml;
  (k) is *Chaetomium* spp, and the MIC ranges from about 0.25 to about 25 μg CPC/ml;
  (l) is *Chaetomium* spp, and the MFC ranges from about 0.25 to about 100 μg CPC/ml;
  (m) is *Phoma* spp, and the MIC ranges from about 0.25 to about 25 μg CPC/ml;
  (n) is *Phoma* spp, and the MFC ranges from about 0.25 to about 100 μg CPC/ml;
  (o) is *Scopulariopsis* spp, and the MIC ranges from about 0.25 to about 25 μg CPC/ml;
  (p) is *Scopulariopsis* spp, and the MFC ranges from about 0.25 to about 100 μg CPC/ml;
  (q) is *Fusarium* spp, and the MIC ranges from about 0.25 to about 25 μg CPC/ml;
  (r) is *Fusarium* spp, and the MFC ranges from about 0.25 to about 100 μg CPC/ml;
  (s) is *Scytalidium* spp, and the MIC ranges from about 0.25 to about 25 μg CPC/ml;
  (t) is *Scytalidium* spp, and the MFC ranges from about 0.25 to about 100 μg CPC/ml;
  (u) is *Alternaria* spp, and the MIC ranges from about 0.25 to about 25 μg CPC/ml;
  (v) is *Alternaria* spp, and the MFC ranges from about 0.25 to about 100 μg CPC/ml;
  (w) is *Epicoccum* spp, and the MIC ranges from about 0.25 to about 25 μg CPC/ml;
  (x) is *Epicoccum* spp, and the MFC ranges from about 0.25 to about 100 μg CPC/ml;
  (y) is *Curvularia* spp, and the MIC ranges from about 0.25 to about 25 μg CPC/ml;
  (z) is *Curvularia* spp, and the MFC ranges from about 0.25 to about 100 μg CPC/ml; or
  (aa) any combination thereof.

9. The method of claim 1, wherein:
(a) the nanoemulsion is stable at about 40° C. and about 75% relative humidity for a time period selected from the group consisting of up to about 1 month, up to about 3 months, up to about 6 months, up to about 12 months, up to about 18 months, up to about 2 years, up to about 2.5 years, and up to about 3 years;
(b) the nanoemulsion is stable at about 25° C. and about 60% relative humidity for a time period selected from the group consisting of up to about 1 month, up to about 3 months, up to about 6 months, up to about 12 months, up to about 18 months, up to about 2 years, up to about 2.5 years, up to about 3 years, up to about 3.5 years, up to about 4 years, up to about 4.5 years, and up to about 5 years;
(c) the nanoemulsion is stable at about 4° C. for a time period selected from the group consisting of up to about 1 month, up to about 3 months, up to about 6 months, up to about 12 months, up to about 18 months, up to about 2 years, up to about 2.5 years, up to about 3 years, up to about 3.5 years, up to about 4 years, up to about 4.5 years, up to about 5 years, up to about 5.5 years, up to about 6 years, up to about 6.5 years, and up to about 7 years; or
(d) any combination thereof.

10. The method of claim 1, wherein the nanoemulsion further comprises:
(a) at least one preservative;
(b) at least one pH adjuster;
(c) at least one buffer;
or
(d) any combination thereof.

11. The method of claim 10, wherein:
(a) the preservative is selected from the group consisting of cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, Bis (p-chlorophenyldiguanido) hexane, 3-(-4-chloropheoxy)-propane-1,2-diol, Methyl and methylchloroisothiazolinone, sodium metabisulphite, citric acid, edetic acid, semi-synthetic derivatives thereof, and combinations thereof; chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens);
(b) the pH adjuster is selected from the group consisting of diethanolamine, lactic acid, monoethanolamine, triethylanolamine, sodium hydroxide, sodium phosphate, semi-synthetic derivatives thereof, and combinations thereof;
(c) the buffer is selected from the group consisting of 2-Amino-2-methyl-1,3-propanediol, 2-Amino-2-methyl-1-propanol, L-(+)-Tartaric acid, ACES, ADA, Acetic acid, Ammonium acetate solution, Ammonium bicarbonate, Ammonium citrate dibasic, Ammonium formate, Ammonium oxalate monohydrate, Ammonium phosphate dibasic, Ammonium phosphate monobasic, Ammonium sodium phosphate dibasic tetrahydrate, Ammonium sulfate solution, Ammonium tartrate dibasic, BES buffered saline, BES, BICINE, BIS-TRIS, Bicarbonate buffer solution, Boric acid, CAPS, CHES, Calcium acetate hydrate, Calcium carbonate, Calcium citrate tribasic tetrahydrate, Citrate Concentrated Solution, Citric acid, hydrous, Diethanolamine, EPPS, Ethylenediaminetetraacetic acid disodium salt dihydrate, Formic acid solution, Gly-Gly-Gly, Gly-Gly, Glycine, HEPES, Imidazole, Lipoprotein Refolding Buffer, Lithium acetate dihydrate, Lithium citrate tribasic tetrahydrate, MES hydrate, MES monohydrate, MES solution, MOPS, Magnesium acetate solution, Magnesium acetate tetrahydrate, Magnesium citrate tribasic nonahydrate, Magnesium formate solution, Magnesium phosphate dibasic trihydrate, Oxalic acid dihydrate, PIPES, Phosphate buffered saline, piperazine, Potassium D-tartrate monobasic, Potassium acetate, Potassium bicarbonate, Potassium carbonate, Potassium chloride, Potassium citrate monobasic, Potassium citrate tribasic solution, Potassium formate, Potassium oxalate monohydrate, Potassium phosphate dibasic, Potassium phosphate dibasic, for molecular biology, anhydrous, Potassium phosphate monobasic, Potassium phosphate monobasic, Potassium phosphate tribasic monohydrate, Potassium phthalate monobasic, Potassium sodium tartrate, Potassium sodium tartrate tetrahydrate, Potassium tetraborate tetrahydrate, Potassium tetraoxalate dihydrate, Propionic acid, STE buffer, STET buffer, Sodium 5,5-diethylbarbiturate, Sodium acetate, Sodium acetate trihydrate, Sodium bicarbonate, Sodium bitartrate monohydrate, Sodium carbonate decahydrate, Sodium carbonate, Sodium citrate monobasic, Sodium citrate tribasic dihydrate, Sodium formate solution, Sodium oxalate, Sodium phosphate dibasic dihydrate, Sodium phosphate dibasic dodecahydrate, Sodium phosphate dibasic solution, Sodium phosphate monobasic dihydrate, Sodium phosphate monobasic monohydrate, Sodium phosphate monobasic solution, Sodium pyrophosphate dibasic, Sodium pyrophosphate tetrabasic decahydrate, Sodium tartrate dibasic dihydrate, Sodium tartrate dibasic solution, Sodium tetraborate decahydrate, TAPS, TES, TM buffer solution, TNT buffer solution, TRIS Glycine buffer, TRIS acetate—EDTA buffer solution, TRIS buffered saline, TRIS glycine SDS buffer solution, TRIS phosphate—EDTA buffer solution, Tricine, Triethanolamine, Triethylamine, Triethylammonium acetate buffer, Triethylammonium phosphate solution, Trimethylammonium acetate solution, Trimethylammonium phosphate solution, Tris-EDTA buffer solution, Trizma® acetate, Trizma® base, Trizma® carbonate, Trizma® hydrochloride, Trizma® maleate, or any combination thereof.

12. The method of claim 1,
wherein the concentration of the cationic CPC is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%.

13. The method of claim 1, wherein the aqueous phase is present in Phosphate Buffered Saline (PBS).

14. The method of claim 1, wherein:
   (a) the nanoemulsion is topically or intradermally applied in a single administration;
   (b) the nanoemulsion is topically or intradermally applied for at least once a week, at least twice a week, at least once a day, at least twice a day, multiple times daily, multiple times weekly, biweekly, at least once a month, or any combination thereof;
   (c) the nanoemulsion is topically or intradermally applied for a period of time selected from the group consisting of about one week, about two weeks, about three weeks, about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years;
   (d) the nanoemulsion is topically applied, followed by washing the application area to remove any residual nanoemulsion; or
   (e) any combination thereof.

15. The method of claim 1, wherein the nanoemulsion is not absorbed systemically in the human subject, or very little of the nanoemulsion is absorbed systemically in the human subject, wherein the lack of such absorption, or the presence of minimal absorption, is determined by the detection of less than 10 ng/mL polysorbate or CPC present in the nanoemulsion in the plasma of the subject.

16. The method of claim 15, wherein:
   (a) less than 5 ng/mL of polysorbate or CPC present in the nanoemulsion is detected in the plasma of the subject;
   (b) less than 3 ng/mL of the polysorbate or CPC present in the nanoemulsion is detected in the plasma of the subject;
   (c) less than 2 ng/mL of the polysorbate or CPC present in the nanoemulsion is detected in the plasma of the subject; or
   (d) a measurable quantity of the one or more surfactants polysorbate or CPC present in the nanoemulsion is below the analytical limit of detection in the plasma of the subject.

17. The method of claim 1, wherein following treatment,
   (a) a negative fungal, yeast, and/or mold culture is obtained;
   (b) a negative potassium hydroxide (KOH) test is obtained; or
   (c) a combination thereof.

18. The method of claim 1, wherein:
   (a) following topical application of the nanoemulsion the nanoemulsion is occluded or semi-occluded;
   (b) following topical application of the nanoemulsion the nanoemulsion is occluded or semi-occluded and occlusion or semi-occlusion is performed by overlaying a bandage, polyolefin film, article of clothing, impermeable barrier, or semi-impermeable barrier to the topical preparation;
   (c) the nanoemulsion is topically applied in the form of an article or carrier such as a bandage, insert, syringe-like applicator, pessary, powder, talc or other solid, solution, liquid, spray, aerosol, ointment, foam, cream, gel, paste, lotion, microcapsules, bioadhesive gel, shampoo, cleanser (leave on and wash off product), sprayer, or combination thereof;
   (d) the nanoemulsion is a controlled release formulation, sustained release formulation, immediate release formulation, or any combination thereof; or
   (e) any combination thereof.

19. The method of claim 1, wherein:
   (a) the infection is of a human nail, nail bed, nail matrix, nail plate, or a combination thereof;
   (b) the infection of the tissue surrounding the nail is paronychia;
   (c) the infection of the tissue surrounding the nail is chronic paronychia; or
   (d) any combination thereof.

20. The method of claim 19, wherein following treatment, partial or complete nail clearing of the infection is observed.

21. The method claim 20, wherein:
   (a) following six weeks of treatment, a subject shows an increase in unaffected linear nail growth, as compared to a baseline;
   (b) following 12 weeks of treatment, a subject shows an increase in unaffected linear nail growth, as compared to a baseline;
   (c) following 18 weeks of treatment, a subject shows an increase in unaffected linear nail growth, as compared to a baseline;
   (d) following 24 weeks of treatment, a subject shows an increase in unaffected linear nail growth, as compared to a baseline;
   (e) following six weeks of treatment, a subject shows a decrease in affected area, as compared to a baseline;
   (f) following 12 weeks of treatment, a subject shows a decrease in affected area, as compared to a baseline;
   (g) following 18 weeks of treatment, a subject shows a decrease in affected area, as compared to a baseline;
   (h) following 24 weeks of treatment, a subject shows a decrease in affected area, as compared to a baseline; or
   (i) any combination thereof.

22. The method of claim 1, wherein the nanoemulsion droplets comprise:
   (a) an aqueous phase;
   (b) about 1% to about 60% soybean oil;
   (c) about 0.1% to about 10% ethanol;
   (d) about 0.1% to about 1% cetylpyridinium chloride;
   (e) about 0.001% to about 10% Tween 20; and
   (f) about 0.0005% to about 1.0% of EDTA.

23. The method of claim 22, wherein the nanoemulsion comprises droplets having an average diameter of less than about 200 nm.

24. The method of claim 1, wherein the fungal, yeast, or mold agent is selected from the group consisting of *Trichophyton tonsurans*, *Trichophyton verrucosum*, *Trichophyton violaceum*, *Candida parapsiliosis*, *Candida krusei*, *Microsporum audouini*, *and Epicoccum nigrum*.

25. The method of claim 1, wherein the nanoemulsion further comprises a chelating agent.

26. The method of claim 25, wherein the chelating agent is present in an amount of about 0.0005% to about 1.0%.

27. The method of claim 25, wherein the chelating agent is selected from the group consisting of ethylenediamine, ethylenediaminetetraacetic acid, and dimercaprol.

28. The method of claim 1, wherein the nanoemulsion further comprises an antifungal agent.

29. The method of claim 28, wherein the antifungal agent, in addition to the nanoemulsion, is selected from the group consisting of (1) azoles (imidazoles), (2) antimetabolites, (3) allylamines, (4) morpholine, (5) glucan Synthesis Inhibitors (chemical family: echinocandins), (6) polyenes, (7) benoxaaborale; (8) other antifungal/onychomycosis agents, and (9) new classes of antifungal/onychomycosis agents.

30. The method of claim 28, wherein the antifungal agent, in addition to the nanoemulsion, is selected from the group consisting of Bifonazole, Clotrimazole, Econazole, Miconazole, Tioconazole, Fluconazole, Itraconazole, Ketoconazole, Pramiconazole, Ravuconazole, Posaconazole, Voriconazole, Flucytosine, Terbinafine, Naftidine, Morpholine, Caspofungin, Micafungin, Anidulafungin, Amphotericin B, Nystatin, pimaricin, griseofulvin, ciclopirox, AN2690, sodarin derivatives and nikkomycins.

31. The method of claim 1, wherein the nanoemulsion droplets have an average diameter greater than about 125 nm and less than about 300 nm.

* * * * *